US007785792B2

(12) United States Patent
Wolffe et al.

(10) Patent No.: US 7,785,792 B2
(45) Date of Patent: Aug. 31, 2010

(54) TARGETED MODIFICATION OF CHROMATIN STRUCTURE

(75) Inventors: Alan P. Wolffe, Orinda, CA (US); Elizabeth J. Wolffe, legal representative, Orinda, CA (US); Trevor Collingwood, Novato, CA (US); Philip D. Gregory, Orinda, CA (US); Andrew Snowden, San Francisco, CA (US); Fyodor Urnov, Point Richmond, CA (US)

(73) Assignee: Sangamo Biosciences, Inc., Richmond, CA (US)

( * ) Notice: Subject to any disclaimer, the term of this patent is extended or adjusted under 35 U.S.C. 154(b) by 15 days.

(21) Appl. No.: 12/217,953

(22) Filed: Jul. 10, 2008

(65) Prior Publication Data

US 2009/0023153 A1 Jan. 22, 2009

Related U.S. Application Data

(60) Continuation of application No. 11/357,615, filed on Feb. 16, 2006, now abandoned, which is a division of application No. 09/844,508, filed on Apr. 27, 2001, now Pat. No. 7,001,768.

(60) Provisional application No. 60/200,590, filed on Apr. 28, 2000, provisional application No. 60/228,523, filed on Aug. 28, 2000.

(51) Int. Cl.
*C12Q 1/68* (2006.01)
*C12Q 1/66* (2006.01)
*C12Q 1/34* (2006.01)
*C12N 15/00* (2006.01)

(52) U.S. Cl. .................. 435/6; 435/8; 435/18; 435/455

(58) Field of Classification Search ........................ None
See application file for complete search history.

(56) References Cited

U.S. PATENT DOCUMENTS

| 5,972,608 | A | 10/1999 | Peterson et al. |
| 6,015,709 | A | 1/2000 | Natesan |
| 6,153,383 | A | 11/2000 | Verdine et al. |
| 6,183,965 | B1 | 2/2001 | Verdine et al. |
| 6,534,261 | B1 | 3/2003 | Cox et al. |
| 6,607,882 | B1 | 8/2003 | Cox et al. |
| 2002/0045158 | A1 | 4/2002 | Case |
| 2002/0173006 | A1 | 11/2002 | Kim |
| 2002/0188103 | A1 | 12/2002 | Bestor |

FOREIGN PATENT DOCUMENTS

| WO | WO 95/09233 | 4/1995 |
| WO | WO 97/11972 | 4/1997 |
| WO | WO 00/23464 | 4/2000 |
| WO | WO 00/41566 | 7/2000 |
| WO | WO 00/42219 | 7/2000 |
| WO | WO 01/52620 | 7/2001 |
| WO | WO 01/59094 | 8/2001 |
| WO | WO 01/68807 | 9/2001 |

OTHER PUBLICATIONS

Ahringer, "NuRD and SIN 3 Histone Deacetylase Complexes in Development," Trends in Genetics 16:351-356 (2000).
Anderson, "Human gene therapy," Nature 392:25-30 (1998).
Armstrong et al., "A SWI/SNF-Related Chromatin Remodeling Complex, E-RC1, Is Required for Tissue-Specific Transcriptional Regulation by EKLF in Vitro," Cell 95:93-104 (1998).
Ayyanathan et al., "Regulated Recruitment of HP1 to a Euchromatic Gene Induces Mitotically Heritable, Epigenetic Gene Silencing: a Mammalian Cell Culture Model of Gene Variegation," Genes & Development 17:1855-1869 (2003).
Bergel et al., "Structural and Functional Definition of the Human Chitinase Chitin-binding Domain," Journal of Biological Chemistry 275(1):514-520 (2000).
Bird et al., "Methylation-Induced Repression-Belts, Braces, and Chromatin," Cell 99:451-454 (1999).
Bochar et al., "A Family of Chromatin Remodeling Factors Related Williams Syndrome Transcription Factor," Proc. Natl. Acad. Sci. U.S.A. 97:1038-1043 (2000).
Boyes et al., "Regulation of Activity of the Transcription Factor GATA-1 by Acetylation," Nature 396:594-598 (1998).
Cai et al., "A Mutant Deubiquitinating Enzyme (Ubp-M) Associates with Mitotic Chromosomes and Blocks Cell Division," Proc. Natl. Acad. Sci. USA 96(6):2828-2833 (1999).
Cairns et al., "Two Functionally Distinct Forms of the RSC Nucleosome-Remodeling Complex, Containing Essential AT Hook, BAH, and Bromodomains," Molecular Cell 4:715-723 (1999).
Cairns, B.R., "Chromatin Remodeling Machines: Similar Motors, Ulterior Motives," Trends Biochem. Sci. 23:20-25 (1998).
Cardoso et al., "Specific interaction between the XNP/ATR-X gene product and the SET domain of the human EZH2 protein," Human Molecular Genetics 7(4):679-684 (1998).
Check, E., "Cancer fears cast doubts on future of gene therapy," Nature 421:678 (2003).
Chen et al., "Regulation of Transcription by a Protein Methyltransferase," Science 284:2174-2177 (1999).
de La Sema et al., "Mammalian SWI-SNF Complexes Contribute to Activation of the hsp 70 Gene," Mol. Cell Biol. 20:2839-2851 (2000).
Devine et al., "After Chromatin is SWItched-on Can it be RUSHed?," Molecular and Cellular Endocrinology 151(1-2):49-56 (1999).
Deuring et al., "The ISWI Chromatin-Remodeling Protein is Required for Gene Expression and the Maintenance of Higher Order Chromatin Structure In Vivo," Mol. Cell 5:355-365 (2000).
Felsenfeld et al., "Controlling the Double Helix," Nature 421:448-453 (2003).
Fryer et al., "Chromatin Remodelling by the Glucocorticoid Receptor Requires the BRG 1 Complex," Nature 393:88-91 (1998).

(Continued)

*Primary Examiner*—Deborah Crouch
(74) *Attorney, Agent, or Firm*—Dahna S. Pasternak; Robins & Pasternak LLP

(57) ABSTRACT

Methods and compositions for targeted modification of chromatin structure, within a region of interest in cellular chromatin, are provided. Such methods and compositions are useful for facilitating processes such as, for example, transcription and recombination, that require access of exogenous molecules to chromosomal DNA sequences.

5 Claims, 7 Drawing Sheets

OTHER PUBLICATIONS

Geng, et al., "Essential Roles of Snf5p in Snf-Swi Chromatin Remodeling In Vivo," Mol Cell Biol. 21:4311-4320 (2001).
Goffeau et al., "Life with 6000 Genes," Science 274:546-547 (1996).
Grant, P., "A Tale of Histone Modifications," Genome Biology 2(4):1-6 (2001).
Grunstein, M., "Histone Acetylation in Chromatin Structure and Transcription," Nature 389:349-352 (1997).
Gu et al., "Activation of p53 Sequence-Specific DNA Binding by Acetylation of the p53-C-Terminal Domain," Cell 90:595-606 (1997).
Guschin et al., "ATP-Dependent Histone Octamer Mobilization and Histone Deacetylation Mediated by the Mi-2 Chromatin Remodeling Complex," Biochemistry 39:5238-5245 (2000).
Hartzog et al., "Nucleosomes and Transcription: Recent Lessons from Genetics," Curr. Opin. Genet. Devel. 7:192-198 (1997).
Herrera et al., "Specific Acetylation of Chromosomal Protein HMG-17 by PCAF Alters Its Interaction with Nucleosomes," Molecular and Cellular Biology 19(5):3466-3473 (1999).
Holstege et al., "Dissecting the Regulatory Circuitry of a Eukaryotic Genome," Cell 95:717-728 (1998).
Hsieh, C.L., "Dependence of transcriptional repression on CpG methylation density," Mol Cell Biol 14(8):5487-5494 (1994).
Imhof et al., "Acetylation of General Transcription Factors by Histone Acetyltransferases," Current Biology 7:689-692 (1997).
Jacobson et al., "Structure and Function of a Human TAF☐.250 Double Bromodomain Module," Science 288:1422-1425 (2000).
Juengst, E.T., "What next for human gene therapy?" BMJ 326:1410-1411 (2003).
Kadam et al., "Functional Selectivity of Recombinant Mammalian SWI/SNF Subunits," Genes & Development 14:2441-2451 (2000).
Kadonaga, J.T., "Eukaryotic Transcription: An Interlaced Network of Transcription Factors and Chromatin-Modifying Machines," Cell 92:307-313 (1998).
Kaiser et al., "A Human Ubiquitin-Conjugating Enzyme Homologous to Yeast UBC8," J. Biol. Chem. 269:8797-8802 (1994).
Kehle et al., "dMi-2, Hunchback-Interacting Protein that Functions in Polycomb Repression," Science 282:1897-1900 (1998).
Kim et al., "Hybrid Restriction Enzymes: Zinc Finger Fusions to Fok I Cleavage Domain," PNAS 93(3):1156-1160 (1996).
Kingston et al., "ATP-Dependent Remodeling and Acetylation as Regulators of Chromatin Fluidity," Genes & Development 13:2339-2352 (1999).
Klug, A., "Zinc Finger Peptides for the Regulation of Gene Expression," J. Mol. Biol. 293:215-218 (1999).
Knoepfler et al., "Sin Meets NuRD and Other Tails of Repression," Cell 99:447-450 (1999).
Kornberg et al., "Twenty-Five Years of the Nucleosome, Fundamental Particle of the Eukaryote Chromosome," Cell 98:285-294 (1999).
Kouzarides, T., "Histone Acetylases and Deacetylases in Cell Proliferation," Current Opin. Genet. Devel. 9:40-48 (1999).
Kuo et al., "Roles of Histone Acetyltransferases and Deacetylases in Gene Regulation," BioEssays 20:615-626 (1998).
Laurent et al., "Functional Interdependence of the Yeast SNF2, SNF5, and SNF6 Proteins in Transcriptional Activation," PNAS 88:2687-2691 (1991).
Laurent, et al., "Yeast SNF2/SWI2, SNF5, and SNF6 proteins function coordinately with the gene-specific transcriptional activators GAL4 and Bicoid," Genes Dev. 6:1707-1715 (1992).
LeRoy et al., "Requirement of RSF and FACT for Transcription of Chromatin Templates in Vitro," Science 282:1900-1904 (1998).
Lo et al., "Snfl -a Histone Kinase That Works in Concert with the Histone Acetyltransferase Gcn5 to Regulate Transcription," Science 293(5532):1142-1146 (2001).
McDowell et al., "Localization of a Putative Transcriptional Regulator (ATRX) at Pericentromeric Heterochromatin and the Short Arms of Acrocentric Chromosomes," PNAS 96:13983-13988 (1999).
Melendy et al., "Chromatin remodeling and initiation of DNA replication," Front Biosci 6:1048-1053 (2001).

Miller et al., "Repetitve Zinc-Binding Domains in the Protein Transcription Factor IIIA From Xenopus Oocytes," EMBO J. 4:1609-1614 (1985).
Mizzen et al., "Linking Histone Acetylation to Transcriptional Regulation," Cellular and Molecular Life Sciences 54:6-20 (1998).
Morales et al., "Chromatin structure and dynamics: functional implications," Biochimie 83:1029-1039 (2001).
Munshi et al., "Acetylation of HMG I(Y) by CBP Turns Off IFN β Expression by Disrupting the Enhanceosome," Molecular Cell 2:457-467 (1998.
Muchardt et al., "A Human Homologue of *Saccharomyces cerevisiae* SNF2/SW12 and Drosophila brm Genes Potentiates Transcriptional Activation by the Glucocoticoid Receptor," EMBO Journal 12:4279-4290 (1993).
Muchardt et al., "ATP-Dependent Chromatin Remodelling: SWI/SNF and Co. are on the Job," Journal of Molecular Biology 293:187-198 (1999).
Murphy et al., "Human SWI-SNF Component BRGI Represses Transcription of the c-fos Gene," Molecular and Cellular Biology 19(4):2724-2733 (1999).
Näär et al., "Composite Co-Activator ARC Mediates Chromatin-Directed Transcriptional Activation," Nature 398:828-832 (1999).
Neely et al., "Activation Domain-Mediated Trargeting of the SWI/SNF Complex to Promoters Stimulates Transcription from Nucleosome Arrays," Molecular Cell 4:649-655 (1999).
Nielsen et al., "Rb Targets Histone H3 Methylation and HP1 to Promoters," Nature 412:561-565 (2001).
Ng et al., "Histone Deacetylases: Silencers for Hire," Trends Biochem. Sci. 25:121-126 (2000).
Omichinski et al., "The solution structure of a specific GAGA factor-DNA complex reveals a modular binding mode," Nature Structural Biology 4:122-129 (1997).
Pazin et al., "ATP-Dependent Nucleosome Reconfiguration and Transcriptional Activation from Preassembled Chromatin Templates," Science 266:2007-2011 (1994).
Peterson, C.L., "Multiple SWItches to turn on chromatin?" Curr Opin Genet Dev 6:171-175 (1996).
Peterson et al., "Promoter Targeting and Chromatin Remodeling by the SWI/SNF Complex," Current Opinions in Genetics & Development 10:187-192 (2000).
Peterson et al., "Recruitment of Chromatin Remodeling Machines," Journal of Cellular Biochemistry 78:179-185 (2000).
Picketts et al., "ATRX Encodes a Novel Member of the SNF2 Family of Proteins: Mutations Point to a Common Mechanism Underlying the ATR-X Syndrome," Human Molecular Genetics 5(12):1899-1907 (1996).
Pham et al., "Ubiquitin-Activating/Conjugating Activity of $TAF_{11}250$, a Mediator of Activation of Gene Expression in Drosohila," Science 289:2357-2360 (2000).
Rachez et al., "Ligand-Dependent Transcription Activation by Nuclear Receptors Requires the DRIP Complex," Nature 398:824-828 (1999).
Rea et al., Regulation of Chromatin Structure by Site-Specific Histone H3 Methyltransferases, Nature 406:593-599 (2000).
Rhodes et al., "Zinc Fingers," Scientific American 268(2):56-65 (1993).
Roth et al, "Histone Acetylation and Chromatin Assembly: A Single Escort, Multiple Dances?," Cell 87:5-8 (1996).
Rutter et al., "A single nucleotide polymorphism in the matrix metalloproteinase-1 promoter creates an Ets binding site and augments transcription," Cancer Res 58:5321-5325 (1998).
Sassone-Corsi et al., "Requirement of Rsk-2 for Epidermal Growth Factor-Activated Phosphorylation of Histone H3," Science 285:886-891 (1999).
Schultz et al., "Targeting Histone Deacetylase Complexes Via KRAB-Zinc Finger Proteins: The PHD and Bromodomains of KAP-1 Form a Cooperative Unit That Recruits a Novel Isoform of the Mi-2α Subunit of NuRD," Genes & Development 15:428-443 (2001).
Sterner et al., "Studies of Acetylation and Deacetylation in High Mobility Group Proteins," The Journal of Biological Chemistry 256(17):8892-8895 (1981).

Sterner et al., "Acetylation of Histones and Transcription-Related Factors," Microbiology and Molecular Biology Review 64(2):435-459 (2000).

Strahl et al., "The Language of Covalent Histone Modifications," Nature 403:41-45 (2000).

Struhl, "Histone Acetylation and Transcriptional Regulatory Mechanisms," Genes Dev. 12:599-606 (1998).

Sudarsanam et al., "Whole-Genome Expression Analysis of snf/swi Mutants of *Saccaromyces cerevisiae*," Proc. Natl. Acad. Sci. U.S.A. 97:3364-3369 (2000).

Sudarsanam et al., "The Swi/Snf Family Nucleosome-Remodeling Complexes and Transcriptional Control," Trends in Genetics 16:345-351 (2000).

Tsukiyama et al., "Purification and Properties of an ATP-Dependent Nucleosome Remodeling Factor," Cell 83:1011-1020 (1995).

Tsukiyama et al., "Characterization of the Imitation Switch Subfamily of ATP-Dependent Chromatin-Remodeling Factors in *Saccharomyces cerevisiae*," Genes Dev. 13:686-697 (1999).

Tyler et al., "The "Dark Side" of Chromatin Remodeling: Repressive Effects on Transcription," Cell 99:443-446 (1999).

Urnov et al., "Designed transcription factors as structural, functional and therapeutic probes of chromatin in vivo," EMBO Reports 3:610-615 (2002).

Usui et al., "Three Distinct Forms of Type 2A Protein Phosphatase in Human Erythrocyte Cytosol," J. Biol. Chem. 263:3752-3761 (1988).

Utley, et al., "Transcriptional Activators Direct Histone Acetyltransferase Complexes to Nucleosomes," Nature 394:498-502 (1998).

Van Steensel et al., "Identification of in Vivo DNA Targets of Chromatin Proteins Using Tethered Dam Methyltransferase," Nature Biotechnology 18:424-428 (2000).

Varga Weisz et al., "Energy-Dependent Chromatin Accessiblity and Nucleosome Mobility in a Cell-Free System," EMBO J. 14(10):2209-2216 (1995).

Varga Weisz et al., "Chromatin-Remodelling Factor CHRAC Contains the ATPases ISWI and Topoisomerase II," Nature 388:598-602 (1997).

Wade et al., "Histone Acetylation: Chromatin in Action," Trends Biochem Sci 22:128-132 (1997).

White et al., "Ligand-Independent Activation of the Oestrogen Receptor by Mutation of a Conserved Tyrosine," EMBO Journal 16(6):1427-1435 (1997).

Wallberg et al., "Recruitment of the SWI-SNF Chromatin Remodeling Complex as a Mechanism of Gene Activation by the Glucocorticoid Receptor tl Activation Domain," Molecular and Cellular Biology 20(6):2004-2013 (2000).

Wang, W., "The SWI/SNF Family of ATP-dependent Chromatin-Remodelers: Similar Mechanisms for Diverse Functions," Current Topics in Microbiology and Immunology 274:143-169 (2003).

Wolffe et al., "Review: Chromatin Structural Features and Targets That Regulate Transcription," Journal of Structural Biology 129:102-122 (2000).

Wolffe et al., "Co-Repressor Complexes and Remodeling Chromatin for Repression," Biochemical Society Transactions 28(4):379-386 (2000).

Wolffe et al., "Targeting Chromatin Disruption Transcription Regulators That Acetylate Histones," Cell 84:817-819 (1996).

Wong et al., "Determinants of Chromatin Disruption and Transcriptional Regulation Instigated by the Thyroid Hormone Receptor: Hormone-Regulated Chromatin Disruption is Not Sufficient for Transcriptional Activation," EMBO Journal 16(11):3158-3171 (1997).

Workman et al., "Alteration of Nucleosome Structure as a Mechanism of Transcriptional Regulation," Ann. Rev. Biochem. 67:545-579 (1998).

Xu et al., "Cytosine Methylation Targetted to Pre-Determined Sequences," Nature Genetics 17:376-378 (1997).

Yoshinaga et al., "Roles of SWI1, SWI2, and SWI3 Proteins for Transcriptional Enhancement by Steroid Receptors," Science 258:1598-1604 (1992).

Zhao et al., "Comparison of the Enzymatic Activities of Native and Recombinant Protein Phosphatase-1 Toward Histone," Biochim Mol. Biol. Int. 34(5)1027-1033 (1994).

pSRC1b-EPO2c

FIGURE 6

ZFP-MBD2b  [NLS] [ZFP-DBD] [MBD2b(262aa)] [Flag]

ZFP-MBD3  [NLS] [ZFP-DBD] [MBD3(285aa)] [Flag]

ZFP-DNMT1  [NLS] [ZFP-DBD] [DNMT1(1617aa)] [Flag]

ZFP-DNMT3a  [NLS] [ZFP-DBD] [DNMT3a(908aa)] [Flag]

ZFP-DNMT3b  [NLS] [ZFP-DBD] [DNMT3a(859aa)] [Flag]

TARGETED MODIFICATION OF CHROMATIN STRUCTURE

CROSS-REFERENCE TO RELATED APPLICATIONS

This application is a continuation of U.S. patent application Ser. No. 11/357,615, filed Feb. 16, 2006, now abandoned which is a divisional of U.S. patent application Ser. No. 09/844,508 filed Apr. 27, 2001 now U.S. Pat. No. 7,001,768 which claims priority under the provisions of 35 U.S.C. §119 to U.S. Provisional Patent Application Ser. No. 60/200,590, filed Apr. 28, 2000 and U.S. Provisional Patent Application Ser. No. 60/228,523, filed Aug. 28, 2000; the disclosures of which are hereby incorporated by reference in their entireties.

TECHNICAL FIELD

The present disclosure is in the fields of chromatin structure and genetic regulation, in particular, the modification of chromatin structure to facilitate interaction of molecules with a region of interest in cellular chromatin.

BACKGROUND

Regulation of gene expression in a cell is generally mediated by sequence-specific binding of gene regulatory molecules, often proteins, to chromosomal DNA. Regulatory proteins can effect either positive or negative regulation of gene expression. Generally, a regulatory protein will exhibit preference for binding to a particular binding sequence, or target site. Target sites for many regulatory proteins (and other molecules) are known or can be determined by one of skill in the art.

Despite advances in the selection and design of sequence-specific DNA binding gene regulatory proteins, their application to the regulation of an endogenous cellular gene can, in some cases, be limited if their access to the target site is restricted in the cell. Possible sources of restricted access could be related to one or more aspects of the chromatin structure of the gene. Access can be influenced by the structure of the gene per se (e.g., nucleotide methylation) or by the structure of the chromosomal domain in which the gene resides.

Cellular DNA, including the cellular genome, generally exists in the form of chromatin, a complex comprising nucleic acid and protein. Indeed, most cellular RNAs also exist in the form of nucleoprotein complexes. The nucleoprotein structure of chromatin has been the subject of extensive research, as is known to those of skill in the art. In general, chromosomal DNA is packaged into nucleosomes; A nucleosome comprises a core and a linker. The nucleosome core comprises an octamer of core histones (two each of H2A, H2B, H3 and H4) around which is wrapped approximately 150 base pairs of chromosomal DNA. In addition, a linker DNA segment of approximately 50 base pairs is associated with linker histone H1 (or a related linker histone in certain specialized cells). Nucleosomes are organized into a higher-order chromatin fiber (sometimes denoted a "solenoid" or a 30 nm fiber) and chromatin fibers are organized into chromosomes. See, for example, Wolffe "Chromatin: Structure and Function" 3$^{rd}$ Ed., Academic Press, San Diego, 1998 and Kornberg et al. (1999) *Cell* 98:285-294.

Chromatin structure is not static, but is subject to modification by processes collectively known as chromatin remodeling. Chromatin remodeling can serve, for example, to remove nucleosomes from a region of DNA, move nucleosomes from one region of DNA to another, change the spacing between nucleosomes or add nucleosomes to a region of DNA in the chromosome. Chromatin remodeling can also result in changes in higher order structure, thereby influencing the balance between transcriptionally active chromatin (open chromatin or euchromatin) and transcriptionally inactive chromatin (closed chromatin or heterochromatin).

Chromosomal proteins are subject to numerous types of chemical modification, some or all of which influence chromatin structure. For example, histones are subject to acetylation by histone acetyltransferases, deacetylation by histone deacetylases, methylation by histone methyltransferases (and therefore presumably to demethylation by histone demethylases), ubiquitination by ubiquitin ligases, de-ubiquitination by ubiquitin hydrolases, phosphorylation by histone kinases, dephosphorylation by histone phosphatases, and reversible ADP-ribosylation by poly-ADP ribose polymerase (PARP, also known as TFIIC). Strahl et al. (2000) *Nature* 403:41-45. Regulation of chromatin structure by methylation of histone H3 has been described. Rea et al. (2000) *Nature* 406:593-599. Modifications of non-histone chromosomal proteins include, for example, acetylation of HMG-1 (Munshi et al. (1998) *Mol. Cell.* 2:457-467); HMGs 14 and 17 (Sterner et al. (1981) *J. Biol. Chem.* 256:8892-8895; Herrera et al. (1999) *Mol. Cell. Biol.* 19:3466-3473; Bergel et al. (2000) *J. Biol. Chem.* 275:11,514-11,520) and chromatin-resident transcriptional regulators such as, for example, TFIIE (Imhof et al. (1997) *Curr. Biol.* 7:689-692), p53 (Gu et al. (1997) *Cell* 90:595-606) and GATA-1 (Boyes et al. (1998) *Nature* 396:594-598). Chemical modification of histone and/or non-histone proteins is often a step in the chromatin remodeling process, and can have either positive or negative effects on gene expression. Generally, histone acetylation is correlated with gene activation; while deacetylation of histones is correlated with gene repression.

A number of enzymes capable of chemical modification of histones have been described and partially characterized. For example, histone acetyl transferases include Gcn5p, p300/CBP-associated factor (P/CAF), p300, CREB-binding protein (CBP), HAT1, TFIID-associated factor 250 (TAF$_{II}$250), and steroid receptor coactivator-1 (SRC-1). Wade et al. (1997) *Trends Biochem. Sci.* 22:128-132; Kouzarides (1999) *Curr. Opin. Genet. Devel.* 9:40-48; Sterner et al. (2000) *Microbiol. Mol. Biol. Rev.* 64:435-459. The HDAC family of proteins have been identified as histone deacetylases and include homologues to the budding yeast histone deacetylase RPD3 (e.g., HDAC1, HDAC2, HDAC3 and HDAC8) and homologues to the budding yeast histone deacetylase HDA1 (e.g., HDAC4, HDAC5, HDAC6 and HDAC7). Ng et al. (2000) *Trends Biochem. Sci.* 25:121-126. The Rsk-2 (RKS90) kinase has been identified as a histone kinase. Sassone-Corsi et al. (1999) *Science* 285:886-891. A histone methyltransferase (CARM-1) has also been identified. Chen et al. (1999) *Science* 284:2174-2177.

Effects of alterations in chromatin structure upon gene expression have been reported or inferred. Fryer et al. (1998) *Nature* 393:88-91; and Kehle et al. (1998) *Science* 282:1897-1900.

Because of the dynamic structure of cellular chromatin, the ability of a regulatory molecule to bind its target site in a chromosome may be limited, in certain circumstances, by chromatin structure. For example, if a target site is present in "open" chromatin (generally thought of as nucleosome-free or having an altered nucleosomal conformation compared to bulk chromatin) structural barriers to the binding of a regulatory molecule to its target site are unlikely. By contrast, if a target site is present in "closed" chromatin (i.e. having extensive higher-order structure and/or close nucleosome spacing), steric barriers to binding are likely to exist. Thus, the ability of a regulatory molecule to bind to a target site in cellular chromatin will depend on the structure of the chromatin surrounding that particular target site. The chromatin structure of a particular gene can vary depending on, for example, cell type and/or developmental stage. For this reason, the regulation of a given gene in a particular cell can be influenced not only by the presence or absence of gene regulatory factors, but also by the chromatin structure of the gene.

Remodeling of chromatin can lead to activation of gene expression in vitro. For example, the NURF chromatin remodeling complex stimulates the transcriptional activation activity of the GAGA transcription factor. Tsukiyama et al. (1995) *Cell* 83:1011-1020. Transcriptional activation by a GAL4-VP16 fusion requires the RSF chromatin remodeling complex. LeRoy et al; (1998) *Science* 282:1900-1904. The SWI/SNF chromatin remodeling complex potentiates transcriptional activation by the VP16 activation domain and by ligand-bound glucocorticoid receptor. Neely et al. (1999) *Mol. Cell.* 4:649-655; Wallberg et al. (2000) *Mol. Cell. Biol.* 20:2004-2013.

There are also several examples of a requirement for the activity of chromatin remodeling complexes for gene activation in vivo. The human SWI/SNF chromatin remodeling complex is required for the activity of the glucocorticoid receptor. Fryer et al. (1998) *Nature* 393:88-91. The mammalian SWI/SNF chromatin remodeling complex is required for activation of the hsp70 gene. de La Serna et al. (2000) *Mol. Cell. Biol.* 20:2839-2851. Mutations in the *Drosophila* ISWI protein adversely affect expression of the engrailed and Ultrabithorax genes. Deuring et al. (2000) *Mol. Cell.* 5:355-365. Finally, mutations in the yeast SWI/SNF gene result in a decrease in expression of one group of genes and an increase in expression of another group of genes, showing that chromatin remodeling can have both positive and negative effects on gene expression. Holsteege et al. (1998) *Cell* 95:717-728; Sudarsanam et al. (2000) *Proc. Natl. Acad. Sci. USA* 97:3364-3369.

Despite this knowledge of the effects of chromatin remodeling on gene expression in vitro and in vivo, methods for directed manipulation of chromatin structure are not available. Accordingly, for situations in which a regulatory molecule is prevented, by chromatin structure, from interacting with its target site, methods for targeted modification of chromatin structure are needed. Such methods would be useful, for example, to facilitate binding of regulatory molecules to cellular chromatin and/or to facilitate access of DNA-binding molecules to cellular DNA sequences. This, in turn, would facilitate regulation of gene expression, either positively or negatively, by endogenous and exogenous molecules, and provide additional methods for binding these molecules to binding sites within regions of interest in cellular chromatin.

SUMMARY

Disclosed herein are compositions and methods useful for targeted modification of chromatin. These compositions and methods are useful for facilitating processes that depend upon access of cellular DNA sequences to DNA-binding molecules, for example, transcription, replication, recombination, repair and integration.

In one embodiment, targeted modification of chromatin facilitates regulation of gene expression by endogenous or exogenous molecules, by providing access to cellular DNA sequences. Modification is any change in chromatin structure, compared to the normal state of the chromatin in the cell in which it resides.

Accordingly, in one embodiment, a method for modifying a region of interest in cellular chromatin is provided, wherein the method comprises contacting cellular chromatin with a fusion molecule that binds to a binding site in the region of interest. The fusion molecule comprises a DNA-binding domain and a component of a chromatin remodeling complex or a functional fragment thereof. In a preferred embodiment, the fusion molecule is a polypeptide. Cellular chromatin can be present in any type of cell, including prokaryotic, eucaryotic or archaeal. Eucaryotic cells include microorganisms, fungal cells, plants and animals, including vertebrate, mammalian and human cells.

In certain embodiments, the DNA-binding domain of a fusion molecule comprises a triplex-forming nucleic acid, an intercalator, an antibiotic, or a minor groove binder. In a preferred embodiment, the DNA-binding domain comprises a zinc finger DNA-binding domain. In a more preferred embodiment, a fusion molecule is a fusion polypeptide comprising a zinc finger DNA-binding domain. Other polypeptide DNA-binding domains are also useful.

The other portion of the fusion molecule is a component of a chromatin remodeling complex. Numerous chromatin remodeling complexes are known to those of skill in the art. Chromatin remodeling complexes generally contain an enzymatic component, which is often an ATPase, a histone acetyl transferase or a histone deacetylase. ATPase components include, but are not limited to, the following polypeptides: SWI2/SNF2, Mi-2, ISWI, BRM, BRG/BAF, Chd-1, Chd-2, Chd-3, Chd-4 and Mot-1. Additional non-enzymatic components, involved in positioning the enzymatic component with respect to its substrate and/or for interaction with other proteins, are also present in chromatin remodeling complexes and can be used as a portion of a fusion molecule. Many components of chromatin remodeling complexes have been identified by sequence homology. Accordingly, additional chromatin remodeling complexes and their components are likely to be discovered and their use is contemplated by the present disclosure.

Modification of chromatin structure will facilitate many processes that require access to cellular DNA. In one embodiment, chromatin modification facilitates modulation of expression of a gene of interest. Modulation of expression comprises activation or repression of a gene of interest. In a separate embodiment, chromatin modification facilitates recombination between an exogenous nucleic acid and cellular chromatin. In this way, targeted integration of transgenes is accomplished more efficiently.

As noted, a fusion molecule can be a polypeptide. Accordingly, in one embodiment, chromatin modification is accomplished by contacting a cell with a polynucleotide encoding a fusion polypeptide, such that the polynucleotide is introduced into the cell and the fusion polypeptide is expressed in the cell. In this regard, fusion polypeptides comprising a fusion between a DNA-binding domain and a component of a chromatin remodeling complex (or functional fragment thereof), as well as polynucleotides encoding them, are provided. Also provided are cells comprising these fusion polypeptides and cells comprising polynucleotides encoding these fusion polypeptides. Preferred are fusion polypeptides comprising a zinc finger DNA binding domain and polynucleotides encoding them.

In one embodiment, a region of interest in cellular chromatin, which is to be modified, comprises a gene. Exemplary genes whose chromatin structure can be modified through the use of the compositions and methods disclosed herein include, but are not limited to, vascular endothelial growth factor (VEGF), erythropoietin (EPO), androgen receptor, PPAR-γ2, p16, p53, Rb, dystrophin and e-cadherin. Accordingly, in certain embodiments, the DNA binding domain of the fusion molecule is selected to bind to a sequence (i.e., a target site) in one of the aforementioned genes.

In certain embodiments, modification of chromatin structure, using a fusion molecule as disclosed herein, is accompanied by an additional step of contacting cellular chromatin with a second molecule. Often, the modification of chromatin structure effected by the binding of the fusion molecule facilitates the binding of the second molecule. The second molecule can be a transcription regulatory molecule, either an endogenous factor or one that is exogenously supplied to a cell. In certain embodiments, the second molecule is also a fusion molecule, preferably a fusion polypeptide. In a preferred embodiment, the second molecule comprises a zinc finger DNA-binding domain. The second molecule can also comprise, for example, a transcriptional activation domain or a transcriptional repression domain. Thus, in one embodiment, modification of chromatin structure, in a region of interest, by a fusion molecule as disclosed herein provides access for the binding of a second molecule which can regulate the transcription of a gene in or near the region of interest.

In another embodiment, a second molecule is a fusion comprising a DNA binding domain and an enzyme (or functional fragment thereof) that covalently modifies histones, for example, a histone acetyl transferase or a histone deacetylase. In this way, a first fusion molecule facilitates remodeling of chromatin, making it a substrate for the activity of a second fusion molecule that facilitates covalent modification of the remodeled chromatin. Alternatively, a second molecule can comprise a fusion between a DNA binding domain and a component of a chromatin remodeling complex that is different from the one present in the first molecule. In this way, it is possible to recruit multiple chromatin remodeling complexes to a region of interest in cellular chromatin.

In yet another embodiment, cellular chromatin is contacted with three molecules. The first comprises a fusion between a DNA binding domain and a component of a chromatin remodeling complex or a functional fragment thereof. The second molecule can comprise, for example, a transcriptional regulatory molecule (endogenous or exogenous), a fusion between a DNA binding domain and a component of a chromatin remodeling complex or a fusion between a DNA binding domain and an enzyme that covalently modifies histones. The third molecule can be an endogenous or exogenous transcriptional regulatory molecule, or a fusion molecule. A fusion molecule can be a fusion polypeptide and can comprise a DNA binding domain (e.g., a zinc finger DNA binding domain) and a transcriptional regulatory domain, such as, for example, an activation domain or a repression domain. Thus, several combinations of molecules are possible. For example, the first and second molecules can be involved in modifying chromatin structure in a region of interest to allow access to that region by a third molecule which can be, for example, a molecule with transcriptional regulatory function. Alternatively, the first molecule can be involved in the modification of chromatin structure to allow access by the second and third molecules (both of which can be, for example, transcriptional regulatory molecules) in a region of interest in cellular chromatin. In another embodiment, the first molecule can facilitate chromatin remodeling in the region of interest, the second molecule can be involved in covalent modification of histones in the region of interest, and the third molecule can bind in the region of interest and possess transcriptional regulatory function. In similar fashion, fourth, fifth, etc. molecules can also be contacted with cellular chromatin to modify its structure in a region of interest and effect regulation of a gene in that region.

In one embodiment, methods for modulating expression of a gene comprise the steps of contacting cellular chromatin with a first fusion molecule that binds to a binding site in cellular chromatin, wherein the binding site is in the gene, and wherein the first fusion molecule comprises a DNA-binding domain and a component of a chromatin remodeling complex or a functional fragment thereof, and further contacting the cellular chromatin with a second molecule that binds to a target site in the gene and modulates expression of the gene. In a preferred embodiment, the DNA-binding domain of the first fusion molecule is a zinc finger DNA-binding domain.

The second molecule can be, for example, a small molecule therapeutic, a minor groove binder, a peptide, a polyamide, a DNA molecule, a triplex-forming oligonucleotide, an RNA molecule, or a polypeptide. Exemplary polypeptides include, but are not limited to, transcription factors, recombinases, integrases, helicases, and DNA or RNA polymerases. Any of the aforementioned molecules can be either exogenous or endogenous. Alternatively, the second molecule can be a second fusion molecule, for example, a fusion polypeptide. In a preferred embodiment, the second molecule is a fusion polypeptide comprising a zinc finger DNA binding domain. The second fusion molecule can also comprise a transcriptional activation domain or a transcriptional repression domain.

In certain embodiments of methods for modulating expression of a gene, a plurality of first fusion molecules, each having a distinct binding site in the gene, are contacted with cellular chromatin. Similarly, a plurality of second molecules, each having a distinct target site in the gene, can be contacted with cellular chromatin in the practice of methods to modulate expression of a gene. Thus, the disclosed methods for modulating expression of a gene can include the use of a single first fusion molecule and a single second molecule, a single first fusion molecule and a plurality of second molecules, a plurality of first fusion molecules and a single second molecule, and a plurality of first fusion molecules and a plurality of second molecules.

In additional embodiments, expression of a plurality of genes is modulated according to the disclosed methods. This can be accomplished in several ways. In one embodiment, a plurality of first fusion molecules, each binding to a distinct binding site, wherein each distinct binding site is in a distinct gene, are contacted with cellular chromatin. One or more of the first fusion molecules can be a zinc finger fusion polypeptide comprising a zinc-finger DNA-binding domain. In certain embodiments, a first fusion molecule can bind to a shared binding site in two or more of the plurality of genes. In one embodiment of a method for modulating the expression of a plurality of genes, a single first fusion molecule binds to a shared binding site in all of the plurality of genes whose expression is modulated.

Additional methods for modulating the expression of a plurality of genes involve contacting a plurality of second molecules with cellular chromatin, in combination with the contact of one or more first fusion molecules with cellular chromatin. Each of the plurality of second molecules can bind to a distinct target site, wherein each distinct target site is in a distinct gene. Alternatively, a single second molecule can bind to a shared target site in two or more different genes. In one embodiment, a single second molecule binds to a shared target site in all of the plurality of genes whose expression is modulated.

In certain embodiments, to facilitate the binding of the fusion molecule to the cellular chromatin, one or more accessible regions within the region of interest are identified and one or more target sites for the DNA-binding portion of the fusion molecule are identified within the accessible region. In separate embodiments, the DNA-binding domain is capable of binding to nucleosomal DNA sequences and identification of an accessible region is not necessary. In the latter case, chromatin modification, as disclosed herein, often results in the generation of an accessible region in cellular chromatin in the region of interest, which can facilitate the binding of other molecules, either exogenous or endogenous. Exogenous molecules whose binding can be facilitated by the generation of an accessible region through chromatin modification include, but are not limited to, minor groove binders, major groove binders, intercalators, small molecule therapeutics, nucleic acids, and polypeptides, including fusion polypeptides, preferably comprising a zinc finger DNA-binding domain.

Polynucleotides encoding fusions between a DNA-binding domain and a component of a chromatin remodeling complex, and methods for their construction, are also provided.

Fusion polypeptides, comprising a DNA-binding domain and a component of a chromatin remodeling complex, and methods for producing such fusion polypeptides, are also provided. In one embodiment, such fusion polypeptides are produced by expressing a polynucleotide as described in the preceding paragraph in a suitable host cell.

Methods for binding an exogenous molecule to cellular chromatin, wherein the methods comprise targeted modification of chromatin structure as disclosed herein, are also provided.

BRIEF DESCRIPTION OF THE DRAWINGS

FIG. 2A shows EMSA analysis. Unbound probe is at the bottom of the gel and shifted probe (bound to Veg1) is indicated by the arrow to the right of the gel photo. Concentration of Veg1 is given at the top. MBP-VEGF1 indicates a binding reaction in which 15 nM of the Veg1-maltose binding protein fusion was used.

FIG. 2B is a graph depicting Kd.

FIG. 6 is a schematic diagram depicting the structure of a set of fusion molecules described in Example 13. NLS refers to a nuclear localization sequence, ZFP-DBD refers to the VEGF3a/1 zinc finger DNA-binding domain, MBD refers to a portion of a methyl binding domain protein, DNMT refers to a portion of a DNA N-methyl transferase protein, and Flag refers to a FLAG epitope.

DETAILED DESCRIPTION

Figure 1:
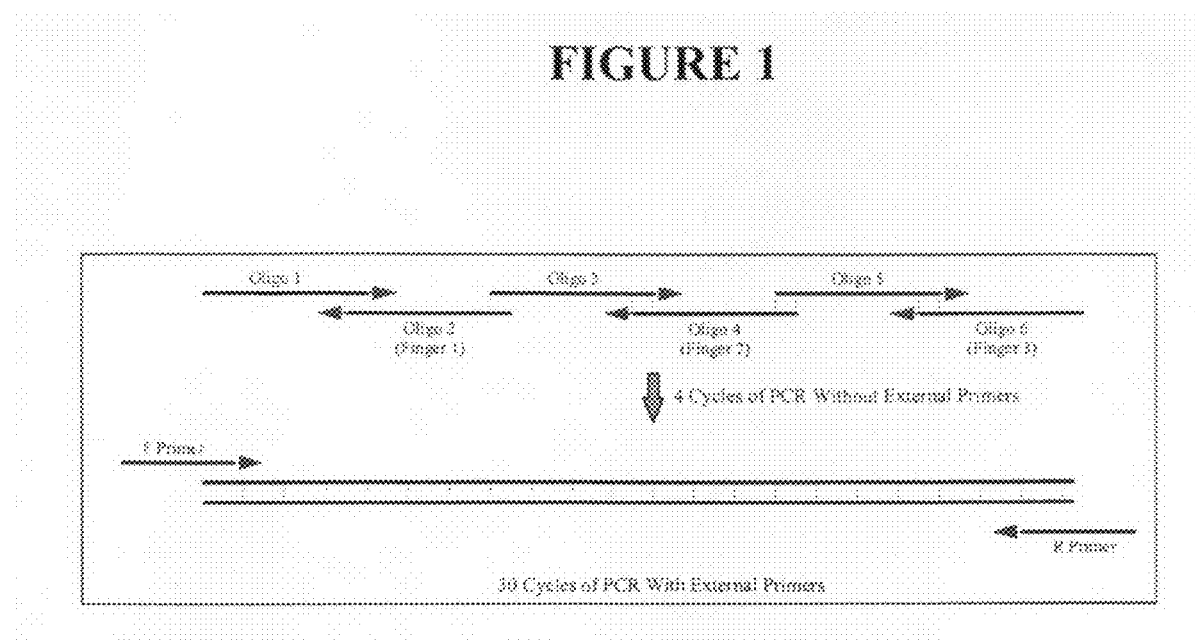
FIG. 1 shows the PCR amplification scheme for production of constructs encoding the Veg1 and Veg3a DNA-binding domains.

Disclosed herein are compositions and methods useful for modifying chromatin structure in a predetermined region of interest in cellular chromatin. Modification of chromatin structure facilitates many processes involving nucleotide sequence-specific interaction of molecules with cellular chromatin. In certain embodiments, modification of chromatin structure is a prerequisite for binding of a regulatory molecule to its target site in cellular chromatin. Such binding can be useful in the regulation of an endogenous cellular gene by one or more endogenous and/or exogenous molecules.

Regulation of gene expression often involves recruitment of a chromatin remodeling complex to a region of cellular chromatin (e.g., the promoter of a gene). Recruitment can occur, for example, by protein-protein interactions between a sequence-specific DNA-binding transcriptional regulatory protein bound at a promoter and a component of the remodeling complex. See, for example, Peterson et al. (2000) *Curr. Opin. Genet. Devel.* 10: 187-192. Alterations in chromatin structure in the vicinity of the promoter, mediated by the recruited remodeling complex, facilitate subsequent interactions that result in transcriptional activation or repression. However, the region to which a remodeling complex can be localized is limited by the sequence specificity of the DNA-binding transcriptional regulatory protein, since most, if not all, protein components of chromatin remodeling complexes do not possess sequence-specific DNA-binding activity. Thus, it is not easy to target chromatin remodeling to a particular region of interest in cellular chromatin unless one possesses a protein that is: (1) capable of binding to chromatin in or near the region of interest, and (2) capable of interacting with at least one component of a multi-subunit chromatin remodeling complex.

The methods and compositions disclosed herein allow targeted modification of any region of interest in cellular chromatin, by employing a fusion molecule comprising a DNA-binding domain and a component of a chromatin remodeling complex or functional fragment thereof. The DNA-binding domain is selected or designed to bind to a target site within or near the region of interest. Any DNA-binding entity having the requisite specificity is suitable. In a preferred embodiment, the DNA-binding domain is a zinc finger DNA-binding domain. Binding of the DNA-binding portion of the fusion molecule localizes the portion of the fusion molecule comprising a component of a chromatin remodeling complex to the region of binding, where it interacts with other components to reconstitute a functional chromatin remodeling complex in the vicinity of the target site. Chromatin remodeling ensues in the vicinity of the target site, which renders the region of binding (e.g., a gene promoter) susceptible to the action of endogenous regulatory factors, and/or to the regulatory activities of exogenous molecules.

It will be apparent to one of skill in the art that targeted remodeling of chromatin will facilitate the regulation of many processes involving access of molecules to DNA in cellular chromatin including, but not limited to, replication, recombination, repair, transcription, telomere function and maintenance, sister chromatid cohesion, and mitotic chromosome segregation. For example, targeted integration of exogenous DNA into cellular chromatin will be enhanced by chromatin remodeling in the region of the desired integration site.

General

The practice of the disclosure employs, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

Chromatin is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

Chromatin modification, or chromatin remodeling, refers to any process by which the structure of chromatin or its constituents is altered. Remodeling can include, for example, removal or repositioning of nucleosomes, addition of nucleosomes, changes in nucleosome density, changes in the path of DNA along the histone octamer, and/or changes in higher-order chromatin structure such as, for example, unwinding of the chromatin solenoid. Chromatin modification can also include modifications to histones or nucleic acid which might not necessarily change the structure of chromatin as assayable by current methods. For example, acetylation or deacetylation of histones, as well as methylation or demethylation of nucleic acid, are instances of chromatin modification.

A chromosome, as is known to one of skill in the art, is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An episome is a replicating nucleic acid, nucleoprotein complex or other structure comprising a nucleic acid that is not part of the chromosomal karyotype of a cell. Examples of episomes include plasmids and certain viral genomes.

A target site is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease. Although binding of a molecule to its target site will generally occur in a naked nucleic acid molecule, a binding molecule may be incapable of binding to its target site in cellular chromatin, as a result of some aspect of the structure of the chromatin in which the target site is located which makes the target site inaccessible to the binding molecule. In other cases, factors in addition to a target site may be required for binding of a molecule to a nucleic acid at the target site. For instance, binding of a molecule to a polynucleotide comprising a target site may require both a particular nucleotide sequence and a particular protein composition adjacent to, or in the vicinity of, the target site. Conditions such as, for example, temperature, pH, and ionic strength can also affect binding of a molecule to its target site.

Target sites for various transcription factors are known. See, for example, Wingender et al. (1997) *Nucleic Acids Res.* 25:265-268 and the TRANSFAC Transcription Factor database, accessed on Apr. 13, 2000. In general, target sites for newly-discovered transcription factors, as well as other types of exogenous molecule, can be determined by methods that are well-known to those of skill in the art such as, for example, electrophoretic mobility shift assay, exonuclease protection, DNase footprinting, chemical footprinting and/or direct nucleotide sequence determination of a binding site. See, for example, Ausubel et al., supra, Chapter 12.

A binding site in cellular chromatin is a region at which a particular molecule, for example a protein, will bind to a target site in the chromatin. A binding site will generally comprise a target site, but not every target site will constitute a binding site in cellular chromatin. For example, a target site may be occluded by one or more chromosomal components, such as histones or nonhistone proteins, or might be rendered inaccessible to its binding molecule because of nucleosomal or higher-order chromatin structure. On the other hand, the presence of one or more chromosomal proteins may be required, in addition to a target site, to define a binding site.

An accessible region is a site in a chromosome, episome or other cellular structure comprising a nucleic acid, in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

An exogenous molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotien, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., protein or nucleic acid, providing it has a sequence that is different from an endogenous molecule. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an endogenous molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and components of chromatin remodeling complexes.

A fusion molecule is a molecule in which two or more subunit molecules are linked, preferably covalently. The subunit molecules can be the same chemical type of molecule, or can be different chemical types of molecules. Examples of the first type of fusion molecule include, but are not limited to, fusion polypeptides (for example, a fusion between a ZFP DNA-binding domain and a transcriptional activation domain) and fusion nucleic acids (for example, a nucleic acid encoding the fusion polypeptide described supra). Examples of the second type of fusion molecule include, but are not limited to, a fusion between a triplex-forming nucleic acid and a polypeptide, and a fusion between a minor groove binder and a nucleic acid. In a preferred embodiment, a fusion molecule is a nucleic acid which encodes a ZFP DNA-binding domain in operative linkage with a component of a chromatin remodeling complex or functional fragment thereof.

A gene, for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

Gene expression refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

Modulation of gene expression refers to a change in the activity of a gene. Modulation of expression can include, but is not limited to, gene activation and gene repression.

Gene activation is any process which results in an increase in production of a gene product. A gene product can be either RNA (including, but not limited to, mRNA, rRNA, tRNA, and structural RNA) or protein. Accordingly, gene activation includes those processes which increase transcription of a gene and/or translation of a mRNA. Examples of gene activation processes which increase transcription include, but are not limited to, those which facilitate formation of a transcription initiation complex, those which increase transcription initiation rate, those which increase transcription elongation rate, those which increase processivity of transcription and those which relieve transcriptional repression (by, for example, blocking the binding of a transcriptional repressor). Gene activation can constitute, for example, inhibition of repression as well as stimulation of expression above an existing level. Examples of gene activation processes which increase translation include those which increase translational initiation, those which increase translational elongation and those which increase mRNA stability. In general, gene activation comprises any detectable increase in the production of a gene product, preferably an increase in production of a gene product by about 2-fold, more preferably from about 2- to about 5-fold or any integer therebetween, more preferably between about 5- and about 10-fold or any integer therebetween, more preferably between about 10- and about 20-fold or any integer therebetween, still more preferably between about 20- and about 50-fold or any integer therebetween, more preferably between about 50- and about 100-fold or any integer therebetween, more preferably 100-fold or more.

Gene repression is any process which results in a decrease in production of a gene product. A gene product can be either RNA (including, but not limited to, mRNA, rRNA, tRNA, and structural RNA) or protein. Accordingly, gene repression includes those processes which decrease transcription of a gene and/or translation of a mRNA. Examples of gene repression processes which decrease transcription include, but are not limited to, those which inhibit formation of a transcription initiation complex, those which decrease transcription initiation rate, those which decrease transcription elongation rate, those which decrease processivity of transcription and those which antagonize transcriptional activation (by, for example, blocking the binding of a transcriptional activator). Gene repression can constitute, for example, prevention of activation as well as inhibition of expression below an existing level. Examples of gene repression processes which decrease translation include those which decrease translational initiation, those which decrease translational elongation and those which decrease mRNA stability. Transcriptional repression includes both reversible and irreversible inactivation of gene transcription. In general, gene repression comprises any detectable decrease in the production of a gene product, preferably a decrease in production of a gene product by about 2-fold, more preferably from about 2- to about 5-fold or any integer therebetween, more preferably between about 5- and about 10-fold or any integer therebetween, more preferably between about 10- and about 20-fold or any integer therebetween, still more preferably between about 20- and about 50-fold or any integer therebetween, more preferably between about 50- and about 100-fold or any integer therebetween, more preferably 100-fold or more. Most preferably, gene repression results in complete inhibition of gene expression, such that no gene product is detectable.

Eucaryotic cells include, but are not limited to, fungal cells (such as yeast), plant cells, animal cells, mammalian cells and human cells.

A region of interest is any region of cellular chromatin, such as, for example, a gene or a non-coding sequence within or adjacent to a gene, in which it is desirable to, for example, modify chromatin structure and/or bind an exogenous molecule. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region.

The terms "operative linkage" and "operatively linked" are used with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. An operatively linked transcriptional regulatory sequence is generally joined in cis with a coding sequence, but need not be directly adjacent to it. For example, an enhancer can constitute a transcriptional regulatory sequence that is operatively-linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a component of a chromatin remodeling complex (or functional fragment thereof), the ZFP DNA-binding domain and the component of the chromatin remodeling complex (or functional fragment thereof) are in operative linkage if, in the fusion polypeptide, the ZFP DNA-binding domain portion is able to bind its target site and/or its binding site, while the component of the chromatin remodeling complex (or functional fragment thereof) is able to interact with other members of its cognate chromatin remodeling complex.

A functional fragment of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

DNA-Binding Domains

In certain embodiments, the compositions and methods disclosed herein involve fusions between a DNA-binding domain and a component of a chromatin remodeling complex. In additional embodiments, the compositions and methods disclosed herein involve fusions between a DNA-binding domain and a domain which participates in modulation of gene expression such as, for example a transcriptional activation domain or a transcriptional repression domain. A DNA-binding domain can comprise any molecular entity capable of sequence-specific binding to chromosomal DNA. Binding can be mediated by electrostatic interactions, hydrophobic interactions, or any other type of chemical interaction. Examples of moieties which can comprise part of a DNA-binding domain include, but are not limited to, minor groove binders, major groove binders, antibiotics, intercalating agents, peptides, polypeptides, oligonucleotides, and nucleic acids. An example of a DNA-binding nucleic acid is a triplex-forming oligonucleotide.

Minor groove binders include substances which, by virtue of their steric and/or electrostatic properties, interact preferentially with the minor groove of double-stranded nucleic acids. Certain minor groove binders exhibit a preference for particular sequence compositions. For instance, netropsin, distamycin and CC-1065 are examples of minor groove binders which bind specifically to AT-rich sequences, particularly runs of A or T. WO 96/32496.

Many antibiotics are known to exert their effects by binding to DNA. Binding of antibiotics to DNA is often sequence-specific or exhibits sequence preferences. Actinomycin, for instance, is a relatively GC-specific DNA binding agent.

In a preferred embodiment, a DNA-binding domain is a polypeptide. Certain peptide and polypeptide sequences bind to double-stranded DNA in a sequence-specific manner. For example, transcription factors participate in transcription initiation by RNA Polymerase II through sequence-specific interactions with DNA in the promoter and/or enhancer regions of genes. Defined regions within the polypeptide sequence of various transcription factors have been shown to be responsible for sequence-specific binding to DNA. See, for example, Pabo et al. (1992) *Ann. Rev. Biochem.* 61:1053-1095 and references cited therein. These regions include, but are not limited to, motifs known as leucine zippers, helix-loop-helix (HLH) domains, helix-turn-helix domains, zinc fingers, β-sheet motifs, steroid receptor motifs, bZIP domains homeodomains, AT-hooks and others. The amino acid sequences of these motifs are known and, in some cases, amino acids that are critical for sequence specificity have been identified. Polypeptides involved in other process involving DNA, such as replication, recombination and repair, will also have regions involved in specific interactions with DNA. Peptide sequences involved in specific DNA recognition, such as those found in transcription factors, can be obtained through recombinant DNA cloning and expression techniques or by chemical synthesis, and can be attached to other components of a fusion molecule by methods known in the art.

Proteins containing methyl binding domains, or functional fragments thereof, can also be used as DNA-binding domains. Methyl binding domain proteins recognize and bind to CpG dinucleotide sequences in which the C residue is methylated. Proteins containing a methyl-binding domain include, but are not limited to, MBD 1, MBD2, MBD3, MBD4, MeCP1 and MeCP2. See, for example, Bird et al. (1999) Cell 99:451-454.

Additionally, DNA methyl transferases, which methylate the 5-position of C residues in CpG dinucleotides such as, for example, DNMT1, DNMT2, DNMT3a and DNMT3b, or functional fragments thereof, can be used as a DNA-binding domain. Furthermore, enzymes which demethylate methylated CpG, or functional fragments thereof, can be used as a DNA-binding domain. Fremant et al. (1997) *Nucleic Acids Res.* 25:2375-2380; Okano et al (1998) *Nature Genet.* 19:219-220; Bhattacharya et al. (1999) *Nature* 397:579-583; and Robertson et al. (2000) *Carcinogenesis* 21:461-467.

In a more preferred embodiment, a DNA-binding domain comprises a zinc finger DNA-binding domain. See, for example, Miller et al. (1985) *EMBO J.* 4:1609-1614; Rhodes et al. (1993) *Scientific American* February:56-65; and Klug (1999) *J. Mol. Biol.* 293:215-218. In one embodiment, a target site for a zinc finger DNA-binding domain is identified according to site selection rules disclosed in co-owned WO 00/42219. ZFP DNA-binding domains are designed and/or selected to recognize a particular target site as described in co-owned WO 00/42219; WO 00/41566; and U.S. Ser. No. 09/444,241 filed Nov. 19, 1999 and 09/535,088 filed Mar. 23, 2000; as well as U.S. Pat. Nos. 5,189,538; 6,007,408; and 6,013,453; and PCT publications WO 95/19431, WO 98/54311, WO 00/23464 and WO 00/27878.

Certain DNA-binding domains are capable of binding to DNA that is packaged in nucleosomes. See, for example, Cordingley et al. (1987) *Cell* 48:261-270; Pina et al. (1990) *Cell* 60:719-731; and Cirillo et al. (1998) *EMBO J.* 17:244-254. Certain ZFP-containing proteins such as, for example, members of the nuclear hormone receptor superfamily, are capable of binding DNA sequences packaged into chromatin. These include, but are not limited to, the glucocorticoid receptor and the thyroid hormone receptor. Archer et al. (1992) *Science* 255:1573-1576; Wong et al. (1997) *EMBO J.* 16:7130-7145. Other DNA-binding domains, including certain ZFP-containing binding domains, require more accessible DNA for binding. In the latter case, the binding specificity of the DNA-binding domain can be determined by identifying accessible regions in the cellular chromatin. Accessible regions can be determined as described in co-owned U.S. patent application entitled "Databases of Accessible Region Sequences; Methods of Preparation and Use Thereof," reference S15, filed even date herewith, the disclosure of which is hereby incorporated by reference herein. A DNA-binding domain is then designed and/or selected to bind to a target site within the accessible region.

Chromatin Remodeling Complexes

Two major types of chromatin modification have been described. The first is dependent on covalent modification. Covalent modification of histones occurs by processes such as, for example, acetylation and deacetylation. Covalent modification of DNA is exemplified by methylation of cytosine residues in CpG dinucleotides. The second type of modification results in changes in nucleosome location and/or conformation, and relies on the activity of ATP-driven chromatin remodeling machines. Both types of chromatin modification are carried out in vivo by multiprotein complexes. For the purposes of the present disclosure, proteins involved in either of these types of chromatin modification can comprise a component of a chromatin remodeling complex.

Modifications of the first type often comprise histone acetylation, catalyzed by a complex containing a histone acetyl transferase (HAT), or histone deacetylation, catalyzed by a complex containing a histone deacetylase (HDAC). An example of a complex involved in this type of chromatin modification is a histone deacetylase complex, examples of which include the SIN3 and Mi-2 complexes. Knoepfler et al. (1999) *Cell* 99:447-450. These complexes generally comprise one or more enzymatic components (i.e., a HDAC) as well as one or more non-enzymatic components. Thus, a component of a chromatin remodeling complex can be either an enzymatic or a non-enzymatic component (or a functional fragment of an enzymatic or non-enzymatic component) of a complex involved in the covalent modification of histones.

The second type of chromatin modification is mediated by multiprotein chromatin remodeling complexes, exhibits nucleosome-, histone- and/or DNA-dependent ATPase activity and catalyzes various types of modification of chromatin structure (see infra). Generally, a remodeling complex comprises an enzymatic component (an ATPase protein subunit) and one or more non-enzymatic protein subunits. ATPase subunits are grouped into three major families: the SWI/SNF family, the ISWI family, and the Mi-2/CHD family. See Tyler et al. (1999) *Cell* 99:443-446. A component of a chromatin remodeling complex can comprise one of its constituent proteins or a functional fragment thereof. Thus, a component of a chromatin remodeling complex can be an enzymatic component or a non-enzymatic component.

Enzymatic components of chromatin remodeling complexes include, but are not limited to, the following ATPases: SWI2/SNF2, STH1, BRM, hBRM, BRG1, Mi-2/CHD, ISW1, ISW2, ISWI, and hSNF2h. Tyler et al., supra; Armstrong et al. (1998) *Curr. Opin. Genet. Dev.* 8:165-172; Guschin et al. (1999) *Curr. Biol.* 9:R742-746; and Wolffe et al. (2000) *J. Struct. Biol.* 129:102-122.

Modifications in chromatin structure include those which render chromosomal sequences more accessible to regulatory factors (i.e., formation of "open" chromatin) as well as those which make chromosomal sequences less accessible (i.e., formation of "closed" chromatin). Such modifications can include, for example, removal of nucleosomes from DNA, deposition of nucleosomes onto DNA, repositioning of nucleosomes, changes in nucleosome spacing, changes in nucleosome density, changes in the degree and/or nature of the interaction between DNA and histones in the nucleosome, changes in the path of DNA along the surface of the nucleosome, and/or changes in higher-order chromatin structure such as, for example, unwinding of the chromatin solenoid.

In certain embodiments, the compositions and methods disclosed herein involve fusions between a DNA-binding domain and a component of a chromatin remodeling complex, as described supra, or a polynucleotide encoding such a fusion.

Various chromatin remodeling complexes, their components and their activities have been identified and characterized in several organisms and cell types. Complexes known as SWI/SNF, RSC, ISW1 and ISW2 have been isolated and characterized in yeast. In *Drosophila*, the NURF, CHRAC, ACF and brahma (dSWI/SNF or BRM) complexes have been isolated and characterized. Chromatin remodeling complexes from human cells named brm/BRG (hSWI/SNF), NURD and RSF have been isolated and characterized. See, for example, Cairns (1998) *Trends Biochem. Sci.* 23:20-25; Murchardt et al. (1999) *J. Mol. Biol.* 293:185-197; Kingston et al. (1999) *Genes. Devel.* 13:2339-2352 and their cited references. It is likely that, as the field progresses, additional chromatin remodeling complexes, and their components, will be discovered and characterized; the use of such newly-discovered components of chromatin remodeling complexes is contemplated by the present disclosure. Exemplary chromatin remodeling complexes and their components are now described.

A. SWI/SNF

The SWI/SNF chromatin remodeling complex of yeast comprises the SWI2/SNF2 helicase/ATPase and products of the SNF5, SWI3, SWP73, ARP7, ARP9, SWI1, SNF6, SWP82, SWP29 and SNF11 genes. Arp7 and Arp9 are actin-related proteins. (The SWP29 gene product is also known as either TFG-3 or TAF30.) Peterson et al. (2000) *Curr. Opin. Genet. Devel.* 10:187-192.

B. SWI/SNF Homologues

Several chromatin remodeling complexes, have been isolated based on their possession of a subunit with homology to SWI2. These include the Brahma (BRM) complex in *Drosophila*, the brm/BRG complexes in mammals, and others.

1. Brahma

The *Drosophila* brahma (brm) complex (also known as dSWI/SNF) contains an ATPase subunit, homologous to SWI2/SNF2, called brahma (brm), as well as SNR1, BAP155 (moira), BAP60, BAP111, BAP55, BAP74 and BAP47/ACT1/ACT2 subunits.

2. Mammalian brm/BRG Complexes

In humans and mouse, several complexes comprising one of two SWI2I/SNF2-homologous ATPases have been characterized. In mice, chromatin remodeling complexes contain either of the two SWI2/SNF2 homologues mBRM or mBRG-1, along with subunits named mSNF5 and mBAF60a. Similarly, in human cells, either of the two SWI2/SNF2 homologues hBRM (also known as hSNF2α) or BRG-1 (also known as hSNF2β) are present in chromatin remodeling complexes also containing the hSNF5 (also known as INI-1), hBAF170, hBAF155, hBAF60a (or hBAF60b or hBAF60c), hBAF57, β-actin, hBAF53, hBAF250 (also known as p270) and hBAF110 subunits.

3. Chromatin Remodeling Complexes Active in the Regulation of Human Globin Genes Several chromatin remodeling complexes have been discovered by virtue of their participation in the regulation of globin gene expression in human cells. These include E-RC1, comprising BRG-1 and the BAF57 protein, and the PYR complex, comprising hSNF5/INI1, BAF57, BAF60a, and BAF170.

4. RSC

The RSC complex ("remodels the structure of chromatin"), first identified in yeast, is a 15-subunit complex comprising the SWI2/SNF2 homologous ATPase STH1, along with SFH-1, RSC-8, actin-related proteins, RSC-6 and SAS-5. Two recently characterized subunits of RSC, denoted Rsc1 and Rsc2, each contains two bromodomains, a BAH ("bromo adjacent homology") domain and an A/T hook motif, and thus likely participates in the interaction between the RSC complex and chromatin. Cairns et al. (1999) *Mol. Cell.* 4:715-723.

5. ATRX and Related Proteins

A family of helicase/ATPase proteins with homology to SNF2 have been described. These proteins contain seven conserved domains and are involved in a range of cellular functions, including transcription, recombination and repair. The mammalian ATRX protein is an example of this group of proteins. See Picketts et al. (1996) *Hum. Mol. Genet.* 5:1899-1907.

C. ISWI-Containing Complexes

Several chromatin remodeling machines, initially characterized in *Drosophila* cells; contain an ATPase subunit with homology to yeast SWI2, known as ISWI ("imitation SWI").

1. NURF

NURF (Nucleosome Remodeling Factor) is a Complex of Four polypeptides, isolated from *Drosophila*, that is capable of ATP-dependent remodeling of chromatin. Remodeling by NURF is Sarkosyl-sensitive and nucleosome-dependent (in particular, is dependent on histone tails), and can facilitate binding of transcription factors to chromatir. Tsukiyama et al. (1995) *Cell* 83:1011-1020. The components of NURF include ISWI (a SWI2-related DNA-dependent ATPase, also known as NURF-140), NURF-38, NURF-55 and NURF-215. Additional properties of the NURF complex are disclosed in Sandaltzopoulos et al. (1999) *Meth. Enzymology* 304:757-765 and references cited therein.

2. CHRAC

CHRAC (Chomatin Accessibility Complex) possesses ATP-dependent nucleosome spacing activity and mediates ATP-dependent accessibility of chromatin to restriction endonucleases. Varga Weisz et al. (1995) *EMBO J.* 14:2209-2216; Varga Weisz et al. (1997) *Nature* 388:598-602. The CHRAC complex includes the ISWI ATPase and four additional polypeptides: p15, p20, p175 and DNA topoisomerase II.

3. ACF

The ACF complex LATP-utilizing chromatin assembly and remodeling factor), characterized in *Drosophila*, is able to facilitate the binding of transcriptional activators to chromatin and to affect nucleosome spacing. Ito et al. (1997) *Cell* 90:145-155. ACF contains the ISWI ATPase and three additional polypeptides: p17, ACFI (p185) and ACFII (p170).

4. RSF

The RSF complex (remodeling and spacing factor), found in human cells, contains the ISWI homologue hSNF2h and a subunit known as p325. Its activities include ATP-dependent nucleosome remodeling and spacing. LeRoy et al. (1998) *Science* 282:1900-1904.

5. ISW1

Chromatin remodeling complexes in yeast, with ATPase subunits homologous to the *Drosophila* ISWI ATPase, include ISW1 and ISW2. ISW1 contains the ISW1 ATPase subunit, p74, p105 and p110. ISW1 has been characterized as possessing nucleosome-stimulated ATPase activity and ATP-dependent nucleosome disruption and spacing activities. Tsukiyama et al. (1999) *Genes Dev.* 13:686-697.

6. ISW2

The yeast ISW2 complex contains the ISW2 ATPase along with a second subunit having a molecular weight of 140 kD. ISW2 possesses nucleosome-stimulated ATPase activity and ATP-dependent nucleosome disruption activity. Tsukiyama et al. (1999) supra.

7. WCRF

The WCRF chromatin remodeling complex was isolated from human (HeLa) cells and contains an ISWI-homologous ATPase known as WCRF 135 (SNF2h) and a subunit known as WCRF 180. WCRF 180 has several hallmarks of a transcription factor, including a heterochromatin localization domain, a PHD finger (a cysteine-rich zinc-binding domain) and a bromodomain (a domain reported to be involved in interaction with histones). Bochar et al. (2000) *Proc. Natl. Acad. Sci. USA* 97:1038-1043; Jacobson et al. (2000) *Science* 288:1422-1425.

D. Mi-2 Containing Complexes

Chromatin remodeling complexes from human (NRD/NURD complex) and amphibian cells (Mi-2 complex) contain a nucleosome-dependent ATPase activity called Mi-2 (also known as CHD). Additional protein components of the amphibian Mi-2 complex include Mtal-like (a DNA-binding protein homologous to metastasis-associated protein), RPD3

(the amphibian homologue of histone deacetylases HDAC1 and HDAC2), RbAp48 (a protein which interacts with histone H4), and MBD3 (a protein containing a methylated CpG binding domain). The amphibian complex additionally contains a serine- and proline-rich subunit, p66. Activities of the amphibian Mi-2 complex include a nucleosome-dependent ATPase that is not stimulated by free histones or DNA, translational movement of histone octamers relative to DNA, and deacetylation of core histones within a nucleosome. Guschin et al. (2000) *Biochemistry* 39:5238-5245. Inasmuch as RbAp48 appears to comprise a key structural component of the Mi-2 complex, it is particularly suitable for fusion with a DNA-binding domain for use in the methods disclosed herein.

Human NRD/NURD complexes contain, in addition to Mi-2, homologues of amphibian Mtal-like (MTA-2), RPD3 (HDAC1 and HDAC2), RbAp48 and MBD3, as well as additional proteins. See Zhang et al. (1999) *Genes Dev.* 13:1924-1935; and Kornberg et al. (1999) *Curr. Opin. Genet. Dev.* 9:148-151.

E. DNA Methyl Transferases and Methylated DNA Binding Proteins

As mentioned above, the methyl-binding-domain protein MBD3 is a component of Mi-2-containing chromatin remodeling complexes. MBD3 and related methyl binding domain proteins recognize and bind to CpG dinucleotide sequences in which the C residue is methylated. Thus MBD proteins are capable of recruiting histone deacetylases to regions of chromatin rich in methylated CpG. Accordingly, a MBD protein can comprise a component of a chromatin remodeling complex. Proteins containing a methyl-binding domain include, but are not limited to, MBD1, MBD2, MBD3, MBD4, MeCP1 and MeCP2. See, for example, Bird et al. (1999) *Cell* 99:451-454.

Additionally, DNA methyl transferases, which methylate the 5-position of C residues in CpG dinucleotides such as, for example, DNMT1, DNMT2, DNMT3a and DNMT3b, can be used as components of a chromatin remodeling complex.

Not all remodeling complexes have the same activities and the same effects on chromatin structure. It is possible that, as more sensitive assay methods are developed and/or more loosely-bound subunits or accessory factors are identified, the various chromatin remodeling complexes will be found to possess common activities. Accordingly, the activities attributed herein to individual chromatin remodeling complexes should not be construed as limiting.

Nonetheless, it appears, from the information available to date, that each cell type contains a multiplicity of chromatin remodeling complexes which can share certain common subunits, and that the composition of a chromatin remodeling complex can vary with cell type. The number of polypeptide subunits in a chromatin remodeling complex varies over a wide range, from two in the ISW2 and RSF complexes to over 15 in the yeast RSC complex. It also appears to be the case that different chromatin remodeling complexes can have partially overlapping activities (i.e., that a degree of functional redundancy exists among different chromatin remodeling complexes). The present disclosure is therefore intended to embrace any and all polypeptides present in any type of chromatin remodeling complex, currently known or to be discovered.

Histone acetylase and deacetylase complexes

In the process of gene activation, binding of chromatin remodeling complexes to chromatin generally precedes binding of histone acetyl transferase (HAT) and/or histone deacetylase (HDAC) complexes, suggesting that HAT and HDAC complexes are recruited by the chromatin remodeling complex, or that remodeled chromatin is more conducive to binding of HAT and HDAC complexes. See, for example, Cosma et al. (1999) *Cell* 97:299-311; Krebs et al. (1999) *Genes Dev.* 13:1412-1421. Accordingly, in one embodiment of the claimed methods, chromatin modification facilitates binding of a HAT- or HDAC-containing complex. In this way, chromatin modification facilitates covalent modification of nucleosomal histones by acetylation or deacetylation. Histone acetylation is generally correlated with transcriptional activation; while deacetylation of histones is generally associated with transcriptional repression.

Numerous HAT enzymes have been described, including budding yeast Gcn5p, which is required for expression of a subset of the yeast genome, its mammalian orthologue CREB-binding protein (CBP), p300 (both of the latter two used as coactivators by a wide variety of mammalian transcription factors), $TAF_{II}250$ (a component of the basal transcriptional machinery), and steroid receptor coactivator 1 (SRC-1), which potentiates transcriptional activation by a number of nuclear hormone receptors. Kouzarides (1999) supra; Cheung et al. (2000) *Curr. Opin. Cell Biol.* 12:326-333; and Sterner et al. (2000) supra.

Two major classes of functionally distinct HDACs have been identified in higher eukaryotes. Class I includes HDAC1, HDAC2 and HDAC3, which are homologous to the yeast Rpd3 histone deacetylase. Class II includes HDAC4, HDAC5 and HDAC6; and are homologous to the yeast Hda1 histone deacetylase. Ng et al., supra.

In another embodiment, a ZFP DNA-binding domain is fused to a histone acetyl transferase or to a histone deacetylase, to effect chromatin modification in the form of covalent modification (acetylation or deacetylation) of histones. In yet another embodiment, modification of chromatin by a chromatin remodeling complex is followed by binding of a ZFP-HAT fusion or a ZFP-HDAC fusion, to establish an active or inactive chromatin state, respectively.

In additional embodiments, a fusion between a DNA-binding domain and a protein that is a component of a HAT- or HDAC-containing complex is provided. In this way, it is possible to recruit HAT or HDAC activity to a region of interest in cellular chromatin, depending of the sequence specificity of the DNA-binding domain. HAT- and HDAC-containing complexes, and their component polypeptide subunits, have been described. See, for example, Grunstein (1997) *Nature* 389:349-352; Hartzog et al. (1997) *Curr. Opin. Genet. Devel.* 7:192-198; Kadonaga (1998) *Cell* 92:307-313; Kuo et al. (1998) *BioEssays* 20:615-626; Mizzzen et al. (1998) *Cell. Mol. Life. Sci.* 54:6-20; Struhl (1998) *Genes Devel.* 12:599-606; Workman et al. (1998) *Ann. Rev. Biochem.* 67:545-579; Ng et al. (1999) *Trends Biochem. Sci.* 25:121-126; and Knoepfler et al. (1999) *Cell* 99:447-450. Accordingly components of HAT- and HDAC-containing complexes are well-known to those of skill in the art.

For example, there are several HAT-containing complexes in yeast, one of which is the SAGA complex (Spt-Ada-Gcn5-acetyltransferase). Grant et al. (1997) *Genes Devel.* 11:1640-1650; Ikeda et al. (1999) *Mol. Cell. Biol.* 19:855-863.

HDAC-containing complexes include the Sin3 complex, which is conserved in organisms from yeast to mammals. The components of the yeast Sin3 complex include Sin3p, RPD3 (a histone deacetylase), RbAp48, and RbAp46. The components of the mammalian Sin3 complex include mSin3A, mSin3B, HDAC1, HDAC2, RbAp48, RbAp49, SAP30 and SAP18. Zhang et al. (1998) *Mol. Cell.* 1: 1021-1031. Sin3 proteins from yeast, *Drosophila*, and vertebrates contain a PAH (paired amphipathic helices) domain, comprising four conserved repeats which form two amphipathic helices separated by a flexible linker. HDAC1, HDAC2 and RPD3 are histone deacetylases. The RbAp48 and RbAP49 proteins interact with histones. SAP30 and SAP18 are specificity determinants.

Another HDAC-containing complex (which also possess chromatin remodeling activity, see supra) is the Mi-2 complex. Several Mi-2 complexes have been described in humans and amphibians. The mammalian Mi-2 complex (also known as NuRD) comprises the following polypeptides: Mi-2 (also known as CHD), HDAC1, HDAC2, MTA-2 and MBD3. See, for example, Ahringer (2000) *Trends Genet.* 16:351-356. The amphibian Mi-2 complex comprises Mi-2, Mtal-like (homologous to mammalian MTA2), p66, RbAp48, RPD3 and MBD3. Guschin et al. (2000) *Biochemistry* 39:5238-5245. Binding of the methylated DNA binding protein present in this complex (MBD3) to methylated CpG dinucleotides in upstream regulatory regions localizes the complex and its associated HDAC activity to methylated genes. Thus, it is believed that the Mi-2 complex is involved in the repression of genes whose upstream DNA is methylated at CpG dinucleotides Coactivators and corepressors which associate with the Sin3 complex to aid in targeting and in its interaction with receptors and other transcriptional regulatory proteins have been described. Examples include, but are not limited to, the vertebrate N-CoR, Rb and SMRT proteins and their homologues, as well as the *Drosophila* SMRTER and Groucho proteins and their homologues. For the purposes of the present disclosure, such coactivators and corepressors are considered to be components of chromatin remodeling complexes, inasmuch as they are capable of targeting various types of chromatin modification, if fused to a DNA-binding domain.

For additional details and lists of HAT- and HDAC-containing complexes and proteins with which they interact, see Knoepfler et al., supra; Ng et al., supra; and Ahringer, supra.

Hormone Receptor Functional Domains

The thyroid hormone receptor (TR) is a member of the nuclear hormone receptor superfamily and is normally bound constitutively to its target genes. The effect of TR binding (i.e., either repression or activation of gene expression) ordinarily depends upon the presence or absence of its ligand, thyroid hormone (T3). In the absence of T3 the receptor generally represses gene expression to a level below the basal level. A number of proteins have been identified that are recruited by the unliganded receptor and are believed to constitute a repressive complex. Examples of such proteins include SMRT and NCoR, which interact directly with the receptor, as well as Sin3, which interacts with SMRT/NCoR. Sin3 also interacts with a number of histone deacetylases, for example, HDACs 1 through 8 (some of which may also interact directly with TR). Recruitment of histone deacetylases by DNA-bound TR is believed to play a major role in its ability to confer repression; however, it is also possible that repressive factors other than HDACs are recruited by TR.

Binding of ligand to DNA-bound TR results in the decay of the repressive complex associated with the TR and recruitment of activating factors to the DNA-bound, ligand-bound TR. Such activating factors include, but are not limited to, the histone acetyltransferases SRC-1, CBP/p300 and P/CAF. Oligomeric activation complexes can also be recruited by ligand-bound TR, such as, for example, DRIP and ARC. Rachez et al. (1999) *Nature* 398:824-827; and Naar et al. (1999) *Nature* 398:828-832. These have been shown to interact with other nuclear hormone receptors, in response to ligand binding, and facilitate activation of gene expression in the context of a chromatin template. Another member of the nuclear receptor family, the glucocorticoid receptor (GR), recruits the hBRG1/BAF chromatin remodeling complex in response to ligand binding. Fryer et al. (1998) *Nature* 393: 88-91.

TR and related nuclear receptors are modular proteins comprising an amino-terminal region (of undefined function), a central DNA binding domain and a carboxy-terminal ligand binding domain (LBD). The LBD, in addition to binding hormone, is responsible for interactions with both the repressive and activating factors described above. When the LBD is fused to a heterologous DNA binding domain (Gal4), it mediates repression of a target promoter containing a Gal4 binding site. Collingwood et al. (1998) *EMBO J.* 17:4760-4770. In addition, T3-dependent activation of transcription can be achieved using a fusion of the TR LBD with the Gal4 DNA-binding domain Tone et al. (1994) *J. Biol. Chem.* 269: 31,157-31,161.

Knowledge of the structure of the LBD of TR and related nuclear receptors, together with the results of mutagenesis studies, can be used to design mutant receptors whose repression and activation activity are impervious to hormone concentration. For example, single amino acid mutants of TR that are unable to bind physiological levels of T3 (e.g. G344E, Δ430M, and Δ2761) recruit corepressors to their binding site. Collingwood et al. (1994) *Mol. Endocrinol.* 8:1262-1277; Collingwood et al. (1998) supra. Conversely, mutations causing conformational changes in the ligand binding domain that mimic those induced by hormone binding have been identified in the estrogen receptor (e.g. L536P and Y541D/E/A) and generate constitutively activating forms of the receptor. Eng et al. (1997) *Mol. Cell. Biol.* 17:4644-4653; White et al. (1997) *EMBO J.* 16:1427-1435.

Accordingly, a mutant nuclear hormone receptor LBD derived, for example, from TR or GR can be used as a component of a fusion with a DNA-binding domain, to recruit activating or repressing protein complexes to a region of interest in cellular chromatin. Certain naturally-occurring mutant LBDs are available; and new mutants can be constructed by methods well-known to those of skill in the art. The site of action of such complexes is determined by the specificity of the DNA-binding domain; while their activity is determined by the nature of the mutation to the LBD and is independent of ligand concentration. For instance, a fusion comprising a LBD that has been mutated such that it is unable to bind hormone will facilitate formation of repressive complexes; while a fusion molecule comprising a LBD mutation that changes the conformation of the LBD such that it resembles a ligand-bound LBD will stimulate the formation of complexes that facilitate transcriptional activation.

Thus, for the purposes of the present disclosure, a mutant nuclear hormone receptor LBD can be considered a component of a chromatin remodeling complex.

Construction and Delivery of Fusion Molecules

The methods and compositions disclosed herein include fusion molecules comprising a DNA-binding domain and a component of a chromatin remodeling complex. The component of a chromatin remodeling complex can be either an enzymatic component or a non-enzymatic component. Without wishing to be bound by theory, it is believed that a fusion molecule comprising an enzymatic component will result in modification of a more limited region of cellular chromatin, compared to a fusion molecule comprising a non-enzymatic component. This is because, when the enzymatic component is directly fused to a DNA-binding domain, its activity is regionally restricted to the vicinity of the target site of the DNA-binding domain. (A degree of flexibility might be achieved by providing a linker sequence between the enzymatic component and the DNA-binding domain.) By contrast, if the fusion molecule comprises a non-enzymatic component, there are likely to be several proteins intervening between the DNA-binding domain (and, hence, the target site in the chromatin) and the enzymatic component of the reconstituted chromatin remodeling complex. This potentially allows a wider area of action of the enzymatic component, which could result in remodeling of more extensive sections of chromatin.

Fusion molecules are constructed by methods of cloning and biochemical conjugation that are well-known to those of skill in the art. Fusion molecules comprise a DNA-binding domain and a component of a chromatin remodeling complex or a functional fragment thereof. Fusion molecules also optionally comprise nuclear localization signals (such as, for example, that from the SV40 medium T-antigen) and epitope tags (such as, for example, FLAG and hemagglutinin). Fusion proteins (and nucleic acids encoding them) are designed such that the translational reading frame is preserved among the components of the fusion. See Examples 2 and 4, infra for additional details on the construction of fusion molecules.

Fusions between a polypeptide component of a chromatin remodeling complex (or a functional fragment thereof) on the one hand, and a non-protein DNA-binding domain (e.g., antibiotic, intercalator, minor groove binder, nucleic acid) on the other, are constructed by methods of biochemical conjugation known to those of skill in the art. See, for example, the Pierce Chemical Company (Rockford, Ill.) Catalogue. Methods and compositions for making fusions between a minor groove binder and a polypeptide have been described. Mapp et al. (2000) *Proc. Natl. Acad. Sci. USA* 97:3930-3935.

In certain embodiments, a fusion between a polypeptide DNA-binding domain and a component of a chromatin remodeling complex (or functional fragment thereof) is encoded by a fusion nucleic acid. In such cases, the nucleic acid can be cloned into intermediate vectors for transformation into prokaryotic or eukaryotic cells for replication and/or expression. Intermediate vectors for storage or manipulation of the fusion nucleic acid or production of fusion protein can be prokaryotic vectors, (e.g., plasmids), shuttle vectors, insect vectors, or viral vectors for example. A fusion nucleic acid can also cloned into an expression vector, for administration to a bacterial cell, fungal cell, protozoal cell, plant cell, or animal cell, preferably a mammalian cell, more preferably a human cell.

To obtain expression of a cloned fusion nucleic acid, it is typically subcloned into an expression vector that contains a promoter to direct transcription. Suitable bacterial and eukaryotic promoters are well known in the art and described, e.g., in Sambrook et al., supra; Ausubel et al., supra; and Kriegler, *Gene Transfer and Expression: A Laboratory Manual* (1990). Bacterial expression systems are available in, e.g., *E. coli, Bacillus* sp., and *Salmonella*. Palva et al. (1983) *Gene* 22:229-235. Kits for such expression systems are commercially available. Eukaryotic expression systems for mammalian cells, yeast, and insect cells are well known in the art and are also commercially available, for example, from Invitrogen, Carlsbad, Calif. and Clontech, Palo Alto, Calif.

The promoter used to direct expression of a fusion nucleic acid depends on the particular application. For example, a strong constitutive promoter is typically used for expression and purification of a fusion protein. In contrast, when a fusion protein is used in vivo, either a constitutive or an inducible promoter is used, depending on the particular use of the fusion protein. In addition, a weak promoter can be used, such as HSV TK or a promoter having similar activity. The promoter typically can also include elements that are responsive to transactivation, e.g., hypoxia response elements, Gal4 response elements, lac repressor response element, and small molecule control systems such as tet-regulated systems and the RU-486 system. See, e.g., Gossen et al. (1992) *Proc. Natl. Acad. Sci. USA* 89:5547-5551; Oligino et al. (1998) *Gene Ther.* 5:491-496; Wang et al. (1997) *Gene Ther.* 4:432-441; Neering et al. (1996) *Blood* 88:1147-1155; and Rendahl et al. (1998) *Nat. Biotechnol.* 16:757-761.

In addition to a promoter, an expression vector typically contains a transcription unit or expression cassette that contains additional elements required for the expression of the nucleic acid in host cells, either prokaryotic or eukaryotic. A typical expression cassette thus contains a promoter operably linked, e.g., to the fusion nucleic acid sequence, and signals required, e.g., for efficient polyadenylation of the transcript, transcriptional termination, ribosome binding, and/or translation termination. Additional elements of the cassette may include, e.g., enhancers, and heterologous spliced intronic signals.

The particular expression vector used to transport the genetic information into the cell is selected with regard to the intended use of the fusion polypeptide, e.g., expression in plants, animals, bacteria, fungi, protozoa etc. Standard bacterial expression vectors include plasmids such as pBR322, pBR322-based plasmids, pSKF, pET23D, and commercially available fusion expression systems such as GST and LacZ. Epitope tags can also be added to recombinant proteins to provide convenient methods of isolation, for monitoring expression, and for monitoring cellular and subcellular localization, e.g., c-myc or FLAG.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

Some expression systems have markers for selection of stably transfected cell lines such as thymidine kinase, hygromycin B phosphotransferase, and dihydrofolate reductase. High-yield expression systems are also suitable, such as baculovirus vectors in insect cells, with a fusion nucleic acid sequence under the transcriptional control of the polyhedrin promoter or any other strong baculovirus promoter.

Elements that are typically included in expression vectors also include a replicon that functions in *E. coli* (or in the prokaryotic host, if other than *E. coli*), a selective marker, e.g., a gene encoding antibiotic resistance, to permit selection of bacteria that harbor recombinant plasmids, and unique restriction sites in nonessential regions of the vector to allow insertion of recombinant sequences.

Standard transfection methods can be used to produce bacterial, mammalian, yeast, insect, or other cell lines that express large quantities of fusion protein, which can be purified, if desired, using standard techniques. See, e.g., Colley et al. (1989) *J. Biol. Chem.* 264:17619-17622; and *Guide to Protein Purification, in Methods in Enzymology*, vol. 182 (Deutscher, ed.) 1990. Transformation of eukaryotic and prokaryotic cells are performed according to standard techniques. See, e.g., Morrison (1977) *J. Bacteriol.* 132:349-351; Clark-Curtiss et al. (1983) in *Methods in Enzymology* 101: 347-362 (Wu et al., eds).

Any procedure for introducing foreign nucleotide sequences into host cells can be used. These include, but are not limited to, the use of calcium phosphate transfection, DEAE-dextran-mediated transfection, polybrene, protoplast fusion, electroporation, lipid-mediated delivery (e.g., liposomes), microinjection, particle bombardment, introduction of naked DNA, plasmid vectors, viral vectors (both episomal and integrative) and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

Conventional viral and non-viral based gene transfer methods can be used to introduce nucleic acids into mammalian cells or target tissues. Such methods can be used to administer nucleic acids encoding fusion polypeptides to cells in vitro. Preferably, nucleic acids are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For reviews of gene therapy procedures, see, for example, Anderson (1992) *Science* 256:808-813; Nabel et al. (1993) *Trends Biotechnol.* 11:211-217; Mitani et al. (1993) *Trends Biotechnol.* 11:162-166; Dillon (1993) *Trends Biotechnol.* 11:167-175; Miller (1992) *Nature* 357:455-460; Van Brunt (1988) *Biotechnology* 6(10):1149-1154; Vigne (1995) *Restorative Neurology and Neuroscience* 8:35-36; Kremer et al. (1995) *British Medical Bulletin* 51(1):31-44; Haddada et al., in *Current Topics in Microbiology and Immunology*, Doerfler and Böhm (eds), 1995; and Yu et al. (1994) *Gene Therapy* 1:13-26.

Methods of non-viral delivery of nucleic acids include lipofection, microinjection, ballistics, virosomes, liposomes, immunoliposomes, polycation or lipid:nucleic acid conjugates, naked DNA, artificial virions, and agent-enhanced uptake of DNA. Lipofection is described in, e.g., U.S. Pat. Nos. 5,049,386; 4,946,787; and 4,897,355 and lipofection reagents are sold commercially (e.g., Transfectam™ and Lipofectin™). Cationic and neutral lipids that are suitable for efficient receptor-recognition lipofection of polynucleotides include those of Felgner, WO 91/17424 and WO 91/16024. Nucleic acid can be delivered to cells (ex vivo administration) or to target tissues (in vivo administration).

The preparation of lipid:nucleic acid complexes, including targeted liposomes such as immunolipid complexes, is well known to those of skill in the art. See, e.g., Crystal (1995) *Science* 270:404-410; Blaese et al. (1995) *Cancer Gene Ther.* 2:291-297; Behr et al. (1994) *Bioconjugate Chem.* 5:382-389; Remy et al. (1994) *Bioconjugate Chem.* 5:647-654; Gao et al. (1995) *Gene Therapy* 2:710-722; Ahmad et al. (1992) *Cancer Res.* 52:4817-4820; and U.S. Pat. Nos. 4,186,183; 4,217,344; 4,235,871; 4,261,975; 4,485,054; 4,501,728; 4,774,085; 4,837,028 and 4,946,787.

The use of RNA or DNA virus-based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro, wherein the modified cells are administered to patients (ex vivo). Conventional viral based systems for the delivery of ZFPs include retroviral, lentiviral, poxyiral, adenoviral, adeno-associated viral, vesicular stomatitis viral and herpesviral vectors. Integration in the host genome is possible with certain viral vectors, including the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, allowing alteration and/or expansion of the potential target cell population. Lentiviral vectors are retroviral vector that are able to transduce or infect non-dividing cells and typically produce high viral titers. Selection of a retroviral gene transfer system would therefore depend on the target tissue. Retroviral vectors have a packaging capacity of up to 6-10 kb of foreign sequence and are comprised of cis-acting long terminal repeats (LTRs). The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), simian immunodeficiency virus (SIV), human immunodeficiency virus (HIV), and combinations thereof. Buchscher et al. (1992) *J. Virol.* 66:2731-2739; Johann et al. (1992) *J. Virol.* 66:1635-1640; Sommerfelt et al. (1990) *Virol.* 176:58-59; Wilson et al. (1989) *J. Virol.* 63:2374-2378; Miller et al. (1991) *J. Virol.* 65:2220-2224; and PCT/US94/05700).

Adeno-associated virus (AAV) vectors are also used to transduce cells with target nucleic acids, e.g., in the in vitro production of nucleic acids and peptides, and for in vivo and ex vivo gene therapy procedures. See, e.g., West et al. (1987) *Virology* 160:38-47; U.S. Pat. No. 4,797,368; WO 93/24641; Kotin (1994) *Hum. Gene Ther.* 5:793-801; and Muzyczka (1994) *J. Clin. Invest.* 94:1351. Construction of recombinant AAV vectors are described in a number of publications, including U.S. Pat. No. 5,173,414; Tratschin et al. (1985) *Mol. Cell. Biol.* 5:3251-3260; Tratschin, et al. (1984) *Mol. Cell. Biol.* 4:2072-2081; Hermonat et al. (1984) *Proc. Natl. Acad. Sci. USA* 81:6466-6470; and Samulski et al. (1989) *J. Virol.* 63:3822-3828.

Recombinant adeno-associated virus vectors based on the defective and nonpathogenic parvovirus adeno-associated virus type 2 (AAV-2) are a promising gene delivery system. Exemplary AAV vectors are derived from a plasmid containing the AAV 145 bp inverted terminal repeats flanking a transgene expression cassette. Efficient gene transfer and stable transgene delivery due to integration into the genomes of the transduced cell are key features for this vector system. Wagner et al. (1998) *Lancet* 351 ⊛ (9117):1702-3; and Kearns et al. (1996) *Gene Ther.* 9:748-55.

pLASN and MFG-S are examples are retroviral vectors that have been used in clinical trials. Dunbar et al. (1995) *Blood* 85:3048-305; Kohn et al. (1995) *Nature Med.* 1: 1017-102; Malech et al. (1997) *Proc. Natl. Acad. Sci. USA* 94:12133-12138. PA317/pLASN was the first therapeutic vector used in a gene therapy trial. (Blaese et al. (1995) *Science* 270:475-480. Transduction efficiencies of 50% or greater have been observed for MFG-S packaged vectors. Ellem et al. (1997) *Immunol Immunother.* 44(1):10-20; Dranoff et al. (1997) *Hum. Gene Ther.* 1:111-2.

In applications for which transient expression is preferred, adenoviral-based systems are useful. Adenoviral based vectors are capable of very high transduction efficiency in many cell types and are capable of infecting, and hence delivering nucleic acid to, both dividing and non-dividing cells. With such vectors, high titers and levels of expression have been obtained. Adenovirus vectors can be produced in large quantities in a relatively simple system.

Replication-deficient recombinant adenoviral (Ad) can be produced at high titer and they readily infect a number of different cell types. Most adenovirus vectors are engineered such that a transgene replaces the Ad E1a, E1b, and/or E3 genes; the replication defector vector is propagated in human 293 cells that supply the required E1 functions in trans. Ad vectors can transduce multiple types of tissues in vivo, including non-dividing, differentiated cells such as those found in the liver, kidney and muscle. Conventional Ad vectors have a large carrying capacity for inserted DNA. An example of the use of an Ad vector in a clinical trial involved polynucleotide therapy for antitumor immunization with intramuscular injection. Sterman et al. (1998) *Hum. Gene Ther.* 7:1083-1089. Additional examples of the use of adenovirus vectors for gene transfer in clinical trials include Rosenecker et al. (1996) *Infection* 24:5-10; Sterman et al., supra; Welsh et al. (1995) *Hum. Gene Ther.* 2:205-218; Alvarez et al. (1997) *Hum. Gene Ther.* 5:597-613; and Topf et al. (1998) *Gene Ther.* 5:507-513.

Packaging cells are used to form virus particles that are capable of infecting a host cell. Such cells include 293 cells, which package adenovirus, and ψ2 cells or PA317 cells, which package retroviruses. Viral vectors used in gene therapy are usually generated by a producer cell line that packages a nucleic acid vector into a viral particle. The vectors typically contain the minimal viral sequences required for packaging and subsequent integration into a host, other viral sequences being replaced by an expression cassette for the protein to be expressed. Missing viral functions are supplied in trans, if necessary, by the packaging cell line. For example, AAV vectors used in gene therapy typically only possess ITR sequences from the AAV genome, which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment, which preferentially inactivates adenoviruses.

In many gene therapy applications, it is desirable that the gene therapy vector be delivered with a high degree of specificity to a particular tissue type. A viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al. (1995) *Proc. Natl. Acad. Sci. USA* 92:9747-9751 reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., $F_{ab}$ or $F_v$) having specific binding affinity for virtually any chosen cellular receptor. Although the above description applies primarily to viral vectors, the same principles can be applied to non-viral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described infra. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics; research, or for gene therapy (e.g., via re-infusion of the transfected cells into the host organism) is well known to those of skill in the art. In a preferred embodiment, cells are isolated from the subject organism, transfected with a nucleic acid (gene or cDNA), and re-infused back into the subject organism (e.g., patient). Various cell types suitable for ex vivo transfection are well known to those of skill in the art. See, e.g., Freshney et al., *Culture of Animal Cells, A Manual of Basic Technique,* 3rd ed., 1994, and references cited therein, for a discussion of isolation and culture of cells from patients.

In one embodiment, hematopoietic stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ stem cells in vitro into clinically important immune cell types using cytokines such a GM-CSF, IFN-γ and TNF-γ are known. Inaba et al. (1992) *J. Exp. Med.* 176:1693-1702.

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Iad (differentiated antigen presenting cells). See Inaba et al., supra.

Vectors (e.g., retroviruses, adenoviruses, liposomes, etc.) containing therapeutic nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there are a wide variety of suitable formulations of pharmaceutical compositions of the present disclosure, as described below. See, e.g., *Remington's Pharmaceutical Sciences,* 17th ed., 1989.

Delivery Vehicles

In certain embodiments, one or more polypeptides, comprising a fusion between a DNA-binding domain and a component of a chromatin remodeling complex, can be introduced into a cell. An important factor in the administration of polypeptide compounds is ensuring that the polypeptide has the ability to traverse the plasma membrane of a cell, or the membrane of an intra-cellular compartment such as the nucleus. Cellular membranes are composed of lipid-protein bilayers that are freely permeable to small, nonionic lipophilic compounds and are inherently impermeable to polar compounds, macromolecules, and therapeutic or diagnostic agents. However, proteins, lipids and other compounds, which have the ability to translocate polypeptides across a cell membrane, have been described.

For example, "membrane translocation polypeptides" have amphiphilic or hydrophobic amino acid subsequences that have the ability to act as membrane-translocating carriers. In one embodiment, homeodomain proteins have the ability to translocate across cell membranes. The shortest internalizable peptide of a homeodomain protein, Antennapedia, was found to be the third helix of the protein, from amino acid position 43 to 58. Prochiantz (1996) *Curr. Opin. Neurobiol.* 6:629-634. Another subsequence, the h (hydrophobic) domain of signal peptides, was found to have similar cell membrane translocation characteristics. Lin et al. (1995) *J. Biol. Chem.* 270:14255-14258.

Examples of peptide sequences which can be linked to a fusion polypeptide for facilitating its uptake into cells include, but are not limited to: an 11 amino acid peptide of the tat protein of HIV; a 20 residue peptide sequence which corresponds to amino acids 84-103 of the p16 protein (see Fahraeus et al. (1996) *Curr. Biol.* 6:84); the third helix of the 60-amino acid long homeodomain of Antennapedia (Derossi et al. (1994) *J. Biol. Chem.* 269:10444); the h region of a signal peptide, such as the Kaposi fibroblast growth factor (K-FGF) h region (Lin et al., supra); and the VP22 translocation domain from HSV (Elliot et al. (1997) *Cell* 88:223-233). Other suitable chemical moieties that provide enhanced cellular uptake can also be linked, either covalently or non-covalently, to fusion polypeptides.

Toxin molecules also have the ability to transport polypeptides across cell membranes. Often, such molecules (called "binary toxins") are composed of at least two parts: a translocation or binding domain and a separate toxin domain. Typically, the translocation domain, which can optionally be a polypeptide, binds to a cellular receptor, facilitating transport of the toxin into the cell. Several bacterial toxins, including *Clostridium perfringens* iota toxin, diphtheria toxin (DT), *Pseudomonas* exotoxin A (PE), pertussis toxin (PT), *Bacillus anthracis* toxin, and pertussis adenylate cyclase (CYA), have been used to deliver peptides to the cell cytosol as internal or amino-terminal fusions. Arora et al. (1993) *J. Biol. Chem.* 268:3334-3341; Perelle et al. (1993) *Infect. Immun.* 61:5147-5156; Stenmark et al. (1991) *J. Cell Biol.* 113:1025-1032; Donnelly et al. (1993) *Proc. Natl. Acad. Sci. USA* 90:3530-3534; Carbonetti et al. (1995) *Abstr. Annu. Meet. Am. Soc. Microbiol.* 95:295; Sebo et al. (1995) *Infect. Immun.* 63:3851-3857; Klimpel et al. (1992) *Proc. Natl. Acad. Sci. USA.* 89:10277-10281; and Novak et al. (1992) *J. Biol. Chem.* 267:17186-17193.

Such subsequences can be used to translocate polypeptides, including fusion polypeptides as disclosed herein, across a cell membrane. This is accomplished, for example, by derivatizing the fusion polypeptide with one of these translocation sequences, or by forming an additional fusion of the translocation sequence with the fusion polypeptide. Optionally, a linker can be used to link the fusion polypeptide and the translocation sequence. Any suitable linker can be used, e.g., a peptide linker.

A fusion polypeptide can also be introduced into an animal cell, preferably a mammalian cell, via liposomes and liposome derivatives such as immunoliposomes. The term "liposome" refers to vesicles comprised of one or more concentrically ordered lipid bilayers, which encapsulate an aqueous phase. The aqueous phase typically contains the compound to be delivered to the cell.

The liposome fuses with the plasma membrane, thereby releasing the compound into the cytosol. Alternatively, the liposome is phagocytosed or taken up by the cell in a transport vesicle. Once in the endosome or phagosome, the liposome is either degraded or it fuses with the membrane of the transport vesicle and releases its contents.

In current methods of drug delivery via liposomes, the liposome ultimately becomes permeable and releases the encapsulated compound at the target tissue or cell. For systemic or tissue specific delivery, this can be accomplished, for example, in a passive manner wherein the liposome bilayer is degraded over time through the action of various agents in the body. Alternatively, active drug release involves using an agent to induce a permeability change in the liposome vesicle. Liposome membranes can be constructed so that they become destabilized when the environment becomes acidic near the liposome membrane. See, e.g., *Proc. Natl. Acad. Sci. USA* 84:7851 (1987); *Biochemistry* 28:908 (1989). When liposomes are endocytosed by a target cell, for example, they become destabilized and release their contents. This destabilization is termed fusogenesis. Dioleoylphosphatidylethanolamine (DOPE) is the basis of many "fusogenic" systems.

For use with the methods and compositions disclosed herein, liposomes typically comprise a fusion polypeptide as disclosed herein, a lipid component, e.g., a neutral and/or cationic lipid, and optionally include a receptor-recognition molecule such as an antibody that binds to a predetermined cell surface receptor or ligand (e.g., an antigen). A variety of methods are available for preparing liposomes as described in, e.g.; U.S. Pat. Nos. 4,186,183; 4,217,344; 4,235,871; 4,261,975; 4,485,054; 4,501,728; 4,774,085; 4,837,028; 4,235,871; 4,261,975; 4,485,054; 4,501,728; 4,774,085; 4,837,028; 4,946,787; PCT Publication No. WO 91/17424; Szoka et al. (1980) *Ann. Rev. Biophys. Bioeng.* 9:467; Deamer et al. (1976) *Biochim. Biophys. Acta* 443:629-634; Fraley, et al. (1979) *Proc. Natl. Acad. Sci. USA* 76:3348-3352; Hope et al. (1985) *Biochim. Biophys. Acta* 812:55-65; Mayer et al. (1986) *Biochim. Biophys. Acta* 858:161-168; Williams et al. (1988) *Proc. Natl. Acad. Sci. USA* 85:242-246; Liposomes, Ostro (ed.), 1983, Chapter 1); Hope et al. (1986) *Chem. Phys. Lip.* 40:89; Gregoriadis, *Liposome Technology* (1984) and Lasic, Liposomes: from Physics to Applications (1993). Suitable methods include, for example, sonication, extrusion, high pressure/homogenization, microfluidization, detergent dialysis, calcium-induced fusion of small liposome vesicles and ether-fusion methods, all of which are well known in the art.

In certain embodiments, it may be desirable to target a liposome using targeting moieties that are specific to a particular cell type, tissue, and the like. Targeting of liposomes using a variety of targeting moieties (e.g., ligands, receptors, and monoclonal antibodies) has been previously described. See, e.g., U.S. Pat. Nos. 4,957,773 and 4,603,044.

Examples of targeting moieties include monoclonal antibodies specific to antigens associated with neoplasms, such as prostate cancer specific antigen and MAGE. Tumors can also be diagnosed by detecting gene products resulting from the activation or over-expression of oncogenes, such as ras or c-erbB2. In addition, many tumors express antigens normally expressed by fetal tissue, such as the alphafetoprotein (AFP) and carcinoembryonic antigen (CEA). Sites of viral infection can be diagnosed using various viral antigens such as hepatitis B core and surface antigens (HBVc, HBVs) hepatitis C antigens, Epstein-Barr virus antigens, human immunodeficiency type-1 virus (HIV-1) and papilloma virus antigens. Inflammation can be detected using molecules specifically recognized by surface molecules which are expressed at sites of inflammation such as integrins (e.g., VCAM-1), selectin receptors (e.g., ELAM-1) and the like.

Standard methods for coupling targeting agents to liposomes are used. These methods generally involve the incorporation into liposomes of lipid components, e.g., phosphatidylethanolamine, which can be activated for attachment of targeting agents, or incorporation of derivatized lipophilic compounds, such as lipid derivatized bleomycin. Antibody targeted liposomes can be constructed using, for instance, liposomes which incorporate protein A. See Renneisen et al. (1990) *J. Biol. Chem.* 265:16337-16342 and Leonetti et al. (1990) *Proc. Natl. Acad. Sci. USA* 87:2448-2451.

Pharmaceutical Compositions and Administration

Fusion polypeptides as disclosed herein, and expression vectors encoding fusion polypeptides, can be used in conjunction with various methods of gene therapy to facilitate the action of a therapeutic gene product. In such applications, a fusion polypeptide can be administered directly to a patient, e.g., to facilitate the modulation of gene expression and for therapeutic or prophylactic applications, for example, cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, and the like. Examples of microorganisms whose inhibition can be facilitated through use of the methods and compositions disclosed herein include pathogenic bacteria, e.g., *Chlamydia*, Rickettsial bacteria, Mycobacteria, Staphylococci, Streptococci, Pneumococci, Meningococci and Conococci, *Klebsiella, Proteus, Serratia, Pseudomonas, Legionella, Diphtheria, Salmonella, Bacilli* (e.g., anthrax), *Vibrio* (e.g., cholera), *Clostridium* (e.g., tetanus, botulism), *Yersinia* (e.g., plague), *Leptospirosis*, and *Borrellia* (e.g., Lyme disease bacteria); infectious fungus, e.g., *Aspergillus, Candida* species; protozoa such as sporozoa (e.g., *Plasmodia*), rhizopods (e.g., *Entamoeba*) and flagellates (*Trypanosoma, Leishmania, Trichomonas, Giardia*, etc.); viruses, e.g., hepatitis (A, B, or C), herpes viruses (e.g., VZV, HSV-1, HHV-6, HSV-II, CMV, and EBV), HIV, Ebola, Marburg and related hemorrhagic fever-causing viruses, adenoviruses, influenza viruses, flaviviruses, echoviruses, rhinoviruses, coxsackie viruses, cornaviruses, respiratory syncytial viruses, mumps viruses, rotaviruses, measles viruses, rubella viruses, parvoviruses, vaccinia viruses, HTLV viruses, retroviruses, lentiviruses, dengue viruses, papillomaviruses, polioviruses, rabies viruses, and arboviral encephalitis viruses, etc.

Administration of therapeutically effective amounts of a fusion polypeptide or a nucleic acid encoding a fusion polypeptide is by any of the routes normally used for introducing polypeptides or nucleic acids into ultimate contact with the tissue to be treated. The fusion polypeptides or nucleic acids are administered in any suitable manner, preferably with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there are a wide variety of suitable formulations of pharmaceutical compositions. See, e.g., *Remington's Pharmaceutical Sciences*, 17$^{th}$ ed. 1985.

Fusion polypeptides or nucleic acids, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Compositions can be administered, for example, by intravenous infusion, orally, topically, intraperitoneally, intravesically or intrathecally. The formulations of compounds can be presented in unit-dose or multi-dose sealed containers, such as ampoules and vials. Injection solutions and suspensions can be prepared from sterile powders, granules, and tablets of the kind known to those of skill in the art.

Assays for Chromatin Remodeling

Numerous activities of chromatin remodeling complexes have been described, including but not limited to the following. A characteristic activity of all chromatin remodeling complexes is nucleosome- or DNA-dependent ATPase activity. Chromatin remodeling complexes can facilitate binding of transcription factors to genes in a chromatin context and facilitate accessibility of sequences in chromatin to restriction enzymes and other nucleases. Certain remodeling complexes (those containing the ISWI ATPase) also possess the ability to assemble periodic nucleosome arrays (i.e. they are capable of spacing nucleosomes). Changes in DNA topology (i.e., degree of supercoiling) can also result from the action of chromatin remodeling complexes; these are believed to reflect either alterations of the path of DNA along the nucleosome or alterations in the path of linker DNA along the chromatin fiber. Chromatin remodeling complexes are also capable of transferring histones from chromatin to either DNA or protein acceptors. Stimulation of transcription initiation can also result from the action of chromatin remodeling complexes.

Without wishing to be bound by any particular theory, the inventors recognize the possibility that the mechanism underlying all the above-mentioned activities may be the ability of chromatin remodeling complexes to promote nucleosome sliding or, more basically, to destabilize the histone-DNA interaction. Accordingly, any protein or multiprotein complex capable of destabilizing histone-DNA interactions and/or promoting nucleosome movement is suitable for use as a component of a chromatin remodeling complex.

The various activities of chromatin remodeling complexes can be assayed by a number of techniques, as are known to those of skill in the art, and as have been described in publications disclosing the isolation and characterization of the various chromatin remodeling complexes, as set forth supra. See also Imblazano et al. (1994) *Nature* 370:481-485 and Cote et al. (1993) *Science* 265:53-60 for descriptions of assays involving facilitation of transcription factor binding. Assays involving nucleosome repositioning are described by, for example, Hamiche et al. (1999) *Cell* 97:833-842 and Guschin et al. (2000) *Biochemistry* 39:5238-5245. Accordingly, it is possible for one of skill in the art to determine whether a given multiprotein complex is a chromatin remodeling complex and to determine whether a particular polypeptide is a component of a chromatin remodeling complex or functional fragment thereof. Additional examples of assays for chromatin remodeling activity are provided infra and in publications such as *Methods in Enzymology*, Vol. 304, "Chromatin" (P. M. Wassarman and A. P. Wolffe, eds.), Academic Press, San Diego, 1999; and *Methods in Molecular Biology*, Vol. 119, "Chromatin Protocols" (P. B. Becker, ed.) Humana Press, Totowa, 1999. See also U.S. Pat. No. 5,972, 608.

An additional assay for chromatin modification is modulation of gene expression, when the modification is part of a two-step process in which chromatin modification allows binding of a molecule which modulates gene expression (e.g., a polypeptide comprising a fusion between a zinc finger DNA-binding domain and a transcriptional regulatory domain). Assays for gene modulation (e.g., transcriptional activation and/or repression, reporter gene activity, measurement of protein levels) are well-known to those of skill in the art and are described, for example, in co-owned WO 00/41566.

Applications

The compositions and methods disclosed herein can be used to facilitate a number of processes involving cellular chromatin. These processes include, but are not limited to, transcription, replication, recombination, repair, integration, maintenance of telomeres, and processes involved in chromosome stability and disjunction. Accordingly, the methods and compositions disclosed herein can be used to affect any of these processes, as well as any other process which can be influenced by chromatin structure such as, for example, detection of specific sequences or sequence variants in cellular chromatin.

Targeted modification of chromatin structure, as disclosed herein, can be used in processes such as, for example, therapeutic regulation of disease-related genes, engineering of cells for manufacture of protein pharmaceuticals, pharmaceutical discovery (including target discovery, target validation and engineering of cells for high throughput screening methods) and plant agriculture.

For example, in one embodiment, chromatin modification facilitates access of one or more transcriptional regulatory factors to a target site in cellular chromatin, thereby participating in modulation of gene expression. Modulation of gene expression can include either increases or decreases in the level of gene expression. In another exemplary embodiment, chromatin modification increases the efficiency of recombination, thereby facilitating, for example, targeted integration of an exogenous nucleic acid.

For the purposes of the present disclosure, chromatin includes any cellular nucleoprotein structure. This can include, but is not limited to chromosomes (i.e., nuclear genomes), episomes, organellar nucleoproteins, such as mitochondrial and chloroplast genomes, and nucleoproteins associated with infecting bacterial or viral genomes. It is known that non-eukaryotic genomes are organized into nucleoprotein structures. In eukaryotic cells, the genome is enclosed in the nucleus. Accordingly, contact of a molecule with cellular chromatin includes introduction of the molecule into the nucleus of a cell.

Cells include, but are not limited to, prokaryotic, eukaryotic and Archaeal cells. Eukaryotic cells include plant, fungal, protozoal and animal cells, including mammalian cells, primate cells and human cells.

In one embodiment, modification of chromatin is used to facilitate the modulation of gene expression. Modulation can include gene activation and gene repression, as well as more subtle increases or decreases in the level of gene expression. Activation of gene expression can be mediated, for instance, by the activity of a histone acetyl transferase that has been recruited to a region of interest by the methods and compositions disclosed herein. Repression of gene expression can be mediated, for instance, by the activity of a histone deacetylase that has been recruited to a region of interest by the methods and compositions disclosed herein. Without wishing to be bound by any particular theory, it is believed that modification of chromatin in the vicinity of a particular gene will make that gene's regulatory sequences more (or less, in the case of repression) accessible to transcriptional activators. Alternatively, chromatin modification could render regulatory sequences more accessible to transcriptional repressors or less accessible to positive transcriptional regulatory factors.

Accordingly, expression of any gene in any organism can be modulated by chromatin modification as disclosed herein, including therapeutically relevant genes, genes of infecting microorganisms, viral genes, and genes whose expression is modulated in the process of target validation. Such genes include, but are not limited to, vascular endothelial growth factor (VEGF), VEGF receptors flt and flk, CCR-5, low density lipoprotein receptor (LDLR), estrogen receptor, HER-2/neu, BRCA-1, BRCA-2, phosphoenolpyruvate carboxykinase (PEPCK), CYP7, fibrinogen, apolipoprotein A (ApoA), apolipoprotein B (ApoB), renin, phosphoenolpyruvate carboxykinase (PEPCK), CYP7, fibrinogen, nuclear factor κB (NF-κB), inhibitor of NF-κB (1-κB), tumor necrosis factors (e.g., TNF-α, TNF-β), interleukin-1 (IL-1), FAS (CD95), FAS ligand (CD95L), atrial natriuretic factor, platelet-derived factor (PDF), amyloid precursor protein (APP), tyrosinase, tyrosine hydroxylase, β-aspartyl hydroxylase, alkaline phosphatase, calpains (e.g., CAPN10) neuronal pentraxin receptor, adriamycin response protein, apolipoprotein E (apoE), leptin, leptin receptor, UCP-1, IL-1, IL-1 receptor, IL-2, IL-3, IL-4, IL-5, IL-6, IL-12, IL-15, interleukin receptors, G-CSF, GM-CSF, colony stimulating factor, erythropoietin (EPO), platelet-derived growth factor (PDGF), PDGF receptor, fibroblast growth factor (FGF), FGF receptor, PAF, p16, p19, p53, Rb, p21, myc, myb, globin, dystrophin, eutrophin, cystic fibrosis transmembrane conductance regulator (CFTR), GNDF, nerve growth factor (NGF), NGF receptor, epidermal growth factor (EGF), EGF receptor, transforming growth factors (e.g., TGF-α, TGF-β), fibroblast growth factor (FGF), interferons (e.g., IFN-α, IFN-β and IFN-γ), insulin-related growth factor-1 (IGF-1), angiostatin, ICAM-1, signal transducer and activator of transcription (STAT), androgen receptors, e-cadherin, cathepsins (e.g., cathepsin W), topoisomerase, telomerase, bcl, bcl-2, Bax, T Cell-specific tyrosine kinase (Lck), p38 mitogen-activated protein kinase, protein tyrosine phosphatase (hPTP), adenylate cyclase, guanylate cyclase, α7 neuronal nicotinic acetylcholine receptor, 5-hydroxytryptamine (serotonin)-2A receptor, transcription elongation factor-3 (TEF-3), phosphatidylcholine transferase, ftz, PTI-1, polygalacturonase, EPSP synthase, FAD2-1, Δ-9 desaturase, Δ-12 desaturase, Δ-15 desaturase, acetyl-Coenzyme A carboxylase, acyl-ACP thioesterase, ADP-glucose pyrophosphorylase, starch synthase, cellulose synthase, sucrose synthase, fatty acid hydroperoxide lyase, and peroxisome proliferator-activated receptors, such as PPAR-γ2.

Expression of human, mammalian, bacterial, fungal, protozoal, Archaeal, plant and viral genes can be modulated; viral genes include, but are not limited to, hepatitis virus genes such as, for example, HBV-C, HBV-S, HBV-X and HBV-P; and HIV genes such as, for example, tat and rev. Modulation of expression of genes encoding antigens of a pathogenic organism can be achieved using the disclosed methods and compositions.

Additional genes include those encoding cytokines, lymphokines, interleukins, growth factors, mitogenic factors, apoptotic factors, cytochromes, chemotactic factors, chemokine receptors (e.g., CCR-2, CCR-3, CCR-5, CXCR-4), phospholipases (e.g., phospholipase C), nuclear receptors, retinoid receptors, organellar receptors, hormones, hormone receptors, oncogenes, tumor suppressors, cyclins, cell cycle checkpoint proteins (e.g., Chk1, Chk2), senescence-associated genes, immunoglobulins, genes encoding heavy metal chelators, protein tyrosine kinases, protein tyrosine phosphatases, tumor necrosis factor receptor-associated factors (e.g., Traf-3, Traf-6), apolipoproteins, thrombic factors, vasoactive factors, neuroreceptors, cell surface receptors, G-proteins, G-protein-coupled receptors (e.g., substance K receptor, angiotensin receptor, $\alpha$- and $\beta$-adrenergic receptors, serotonin receptors, and PAF receptor), muscarinic receptors, acetylcholine receptors, GABA receptors, glutamate receptors, dopamine receptors, adhesion proteins (e.g., CAMs, selectins, integrins and immunoglobulin superfamily members), ion channels, receptor-associated factors, hematopoietic factors, transcription factors, and molecules involved in signal transduction. Expression of disease-related genes, and/or of one or more genes specific to a particular tissue or cell type such as, for example, brain, muscle, heart, nervous system, circulatory system, reproductive system, genitourinary system, digestive system and respiratory system can also be modulated.

The fusion molecules disclosed herein comprise a DNA-binding domain which binds to a target site. In certain embodiments, the target site is present in an accessible region of cellular chromatin. Accessible regions can be determined as described in co-owned U.S. patent application entitled "Databases of Accessible Region Sequences; Methods of Preparation and Use Thereof," reference S15, filed even date herewith. In additional embodiments, the DNA-binding domain of a fusion molecule is capable of binding to cellular chromatin regardless of whether its target site is in an accessible region or not. For example, such DNA-binding domains are capable of binding to linker DNA and/or nucleosomal DNA. Examples of this type of "pioneer" DNA binding domain are found in certain steroid receptor and in hepatocyte nuclear factor 3 (HNF3). Cordingley et al., supra; Pina et al., supra; and Cirillo et al., supra.

Methods of chromatin modification in a region of interest can be combined with methods involving binding of endogenous or exogenous transcriptional regulators in the region of interest to achieve modulation of gene expression. Modulation of gene expression can be in the form of repression as, for example, when the target gene resides in a pathological infecting microorganism or in an endogenous gene of the subject, such as an oncogene or a viral receptor, that contributes to a disease state. Alternatively, modulation can be in the form of activation, if activation of a gene (e.g., a tumor suppressor gene) can ameliorate a disease state. For such applications, an exogenous molecule can be formulated with a pharmaceutically acceptable carrier, as is known to those of skill in the art. See, for example, Remington's Pharmaceutical Sciences, $17^{th}$ ed., 1985; and co-owned WO 00/42219.

In one embodiment, a method involves the use of a fusion molecule comprising a DNA-binding domain and a component of a chromatin remodeling complex, to modify chromatin structure in a region of interest, in combination with a second molecule having transcriptional regulatory activity which binds in the region of interest only after modification of chromatin structure in the region of interest. In certain embodiments, the second molecule comprises a fusion between a DNA-binding domain and either a transcriptional activation domain or a transcriptional repression domain. Any polypeptide sequence or domain capable of influencing gene expression, which can be fused to a DNA-binding domain, is suitable for use. Activation and repression domains are known to those of skill in the art and are disclosed, for example, in co-owned WO 00/41566.

Exemplary activation domains include, but are not limited to, VP16, VP64, p300, CBP, PCAF, SRC1 PvALF, AtHD2A and ERF-2. See, for example, Robyr et al. (2000) *Mol. Endocrinol.* 14:329-347; Collingwood et al. (1999) *J. Mol. Endocrinol.* 23:255-275; Leo et al. (2000) *Gene* 245:1-11; Manteuffel-Cymborowska (1999) *Acta Biochim. Pol.* 46:77-89; McKenna et al. (1999) *J Steroid Biochem. Mol. Biol.* 69:3-12; Malik et al. (2000) *Trends Biochem. Sci.* 25:277-283; and Lemon et al. (1999) *Curr. Opin. Genet. Dev.* 9:499-504. Additional exemplary activation domains include, but are not limited to, OsGAI, HALF-1, C1, AP1, ARF-5, -6, -7, and -8, CPRF1, CPRF4, MYC-RP/GP, and TRAB1. See, for example, Ogawa et al. (2000) *Gene* 245:21-29; Okanami et al. (1996) *Genes Cells* 1:87-99; Goff et al. (1991) *Genes Dev.* 5:298-309; Cho et al. (1999) *Plant Mol. Biol.* 40:419-429; Ulmason et al. (1999) *Proc. Natl. Acad. Sci. USA* 96:5844-5849; Sprenger-Haussels et al. (2000) *Plant J* 22:1-8; Gong et al. (1999) *Plant Mol. Biol.* 41:33-44; and Hobo et al. (1999) *Proc. Natl. Acad. Sci. USA* 96:15,348-15,353.

Exemplary repression domains include, but are not limited to, KRAB, SID, MBD2, MBD3, members of the DNMT family (e.g., DNMT1, DNMT3A, DNMT3B), Rb, and MeCP2. See, for example, Bird et al. (1999) *Cell* 99:451-454; Tyler et al. (1999) *Cell* 99:443-446; Knoepfler et al. (1999) *Cell* 99:447-450; and Robertson et al. (2000) *Nature Genet.* 25:338-342. Additional exemplary repression domains include, but are not limited to, ROM2 and AtHD2A. See, for example, Chem et al. (1996) *Plant Cell* 8:305-321; and Wu et al. (2000) *Plant J* 22:19-27.

It is likely that many transcriptional regulatory molecules, both endogenous and exogenous, are unable to interact with their target sites (and, hence, unable to exert their regulatory effects) when the target site is present in cellular chromatin. Without wishing to be bound by any particular theory, it is believed that chromatin modification in a region of interest can make such target sites accessible to their binding molecules. Accordingly, the methods and compositions disclosed herein complement methods of in vivo gene regulation using exogenous molecules, in those cases in which the target site for the exogenous molecule is not in an accessible region in cellular chromatin. Methods of gene regulation using exogenous molecules are disclosed, for example, in co-owned WO 00/41566. These include applications in regulation of plant gene expression, functional genomics and transgenic animals.

Significant difficulties currently exist in therapeutic situations which require the reactivation of a developmentally-silenced gene. Developmentally-induced gene inactivation can be mediated by methylation of CpG islands in the upstream region of a gene. Thus, use of a binding domain specific for methylated DNA as the DNA-binding portion of a fusion can facilitate recruitment of a chromatin remodeling complex to the upstream region of a developmentally-silenced gene, making the gene accessible to exogenous regulatory factors, and resulting in therapeutic re-activation of the gene. In another embodiment, a fusion between a methylated DNA-binding domain and a demethylase can be used for reactivation of a gene silenced by methylation.

The compositions and methods disclosed herein are useful in a variety of applications and provide advantages over existing methods. These include therapeutic methods in which an exogenous molecule is administered to a subject and used to modulate expression of a target gene within the subject. See, for example, co-pending WO 00/41566. The disclosed compositions and methods can also facilitate detection of particular sequences by binding of an exogenous molecule to a binding site in cellular chromatin as in, for example, diagnostic applications. Methods for detection of a target sequence using, for example, a ZFP are described in co-owned WO00/42219. For example, an exogenous molecule, such as a sequence-specific DNA binding protein, can be used to detect variant alleles associated with a disease or with a particular phenotype in patient samples and to detect the presence of pathological microorganisms in clinical samples. In one embodiment, a variant allele comprises a single-nucleotide polymorphism (SNP). In a non-mutually exclusive embodiment, the sequence-specific DNA binding protein is a ZFP. Exogenous molecules can also be used to quantify copy number of a gene in a sample. For example, detection of the loss of one copy of a p53 gene in a clinical sample is an indicator of susceptibility to cancer. Additionally, identification of transgenic plants and animals can be accomplished through detection of a transgene using, for example, binding of a sequence-specific exogenous molecule (such as, for example, a ZFP) as an assay. All of these procedures can be enhanced by recruitment of a chromatin remodeling complex to a region of interest in cellular chromatin to facilitate binding of a binding molecule in the region of interest.

The disclosed methods and compositions, when used in conjunction with methods of binding of exogenous molecules to cellular chromatin, can be used in assays to determine gene function and to determine changes in phenotype resulting from specific modulation of gene expression. See, for example, co-owned U.S. patent application Ser. No. 09/395,448, filed Sep. 14, 1999.

EXAMPLES

The following examples are presented as illustrative of, but not limiting, the claimed subject matter.

Example 1

Design, Synthesis and Binding Properties of a Zinc Finger DNA-binding Domain which Recognizes a Target Sequence in the Human VEGF Gene Target Site A zinc finger DNA-binding domain, which recognizes the human vascular endothelial growth factor-A (VEGF) gene, was designed and constructed according to design rules and methods disclosed in co-owned WO 00/42219, WO 00/41566, and co-owned U.S. patent application Ser. Nos. 09/444,241 filed Nov. 19, 1999, and 09/535,088 filed Mar. 23, 2000. The target site, which overlaps the transcription initiation site for the human VEGF-A gene, is shown below as SEQ ID NO: 1, with the arrow indicating the transcription startsite.

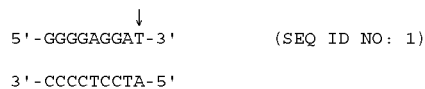
```
      ↓
5'-GGGGAGGAT-3'        (SEQ ID NO: 1)
3'-CCCCTCCTA-5'
```

Backbone Structure

The human SP-1 zinc finger transcription factor was used as backbone for the construction of a designed three-finger DNA binding domain, Veg1, capable of recognizing this sequence. SP-1 has a three finger DNA-binding domain related to the well-studied murine zinc finger protein Zif268. Christy et al. (1988) *Proc. Natl. Acad. Sci. USA* 85:7857-7861. Site-directed mutagenesis experiments using this domain have shown that correlations between the amino acid sequence of a zinc finger and its target nucleotide sequence, derived from analyses of Zif268, are also applicable to SP-1 and hence can be used to adapt the specificity of SP-1 to DNA sequences other than its normal target site. Desjarlais et al. (1994) *Proc. Natl. Acad. Sci. USA* 91:11099-11103. The portion of the SP-1 sequence used for construction of designed zinc finger DNA binding domains corresponds to amino acids 533 to 624.

Amino acid sequences of designed DNA-binding domains are illustrated in Table 1. As can be seen in the Table, the designed Veg1 protein comprises three zinc fingers (F1, F2 and F3) which together recognize a 9-base pair target site. The amino acid sequence of the recognition helix (positions −1 through +6, where +1 is the first amino acid in the α-helix) for each of the DNA-binding fingers is given.

TABLE 1

Target sites and ZFP DNA-binding domains in the human VEGF-A gene

| Name | Target site | Location | AA sequence |
|---|---|---|---|
| Veg 1 | 5'-GGGGAGGAT-3' (SEQ ID NO: 2) | −8 to +1 | F1: TTSNLRR (SEQ ID NO: 3) F2: RSSNLQR (SEQ ID NO: 4) F3: RSDHLSR (SEQ ID NO: 5) |
| Veg 3a | 5'-GCGGAGGCT-3' (SEQ ID NO: 6) | +3 to +11 | F1: QSSDLQR (SEQ ID NO: 7) F2: RSSNLQR (SEQ ID NO: 8) F3: RSDELSR (SEQ ID NO: 9) |

Sequences Encoding the Veg1 DNA-Binding Domain

A polymerase chain reaction (PCR)-based assembly procedure, using six overlapping oligonucleotides, was applied to the synthesis of a synthetic gene encoding the Veg1 DNA-binding domain. See FIG. 1. Three of the oligonucleotides (1, 3, and 5 in FIG. 1) correspond to "universal" sequences that encode portions of the DNA-binding domain between the recognition helices. These oligonucleotides are constant for any given zinc finger construct. The other three "specific" oligonucleotides (2, 4, and 6 in FIG. 1) were designed to encode the recognition helices. These oligonucleotides contained different sequences encoding amino acids at positions −1, +2, +3 and +6 in each recognition helix, depending on its target triplet sequence. Codon bias was chosen to allow expression in both mammalian cells and *E. coli*.

Assembly of Veg1 coding sequences was carried out as follows. First, the six oligonucleotides (three universal and three specific, as described above) were combined and annealed at 25° C. to form a gapped DNA scaffold. Next, gaps were filled by conducting a four-cycle PCR reaction (using Taq and Pfu thermostable DNA polymerases) to generate a double-stranded template. This template was amplified (for thirty cycles) using a pair of external primers containing Kpn I and Hind III restriction sites. PCR products were directly cloned into the Kpn I and Hind III sites of the Tac promoter vector, pMal-c2 (New England Biolabs, Beverly, Mass.). The Veg1 zinc finger DNA-binding domain was expressed from this vector and purified as a fusion with the maltose binding protein according to the manufacturer's instructions (New England Biolabs, Beverly, Mass.).

Accuracy of the Veg1 clone was verified by DNA sequencing. The Veg1 nucleotide and amino acid sequences are as follows.

```
Veg1 nucleotide sequence:
  KpnI
                                              (SEQ ID NO: 10)
GGTACCCATACCTGGCAAGAAGAAGCAGCACATCTGCCACATCCAGGGCT

GTGGTAAAGTTTACGGCACAACCTCAAATCTGCGTCGTCACCTGCGCTGG

CACACCGGCGAGAGGCCTTTCATGTGTACCTGGTCCTACTGTGGTAAACG

CTTCACCCGTTCGTCAAACCTGCAGCGTCACAAGCGTACCCACACCGGTG

AGAAGAAATTTGCTTGCCCGGAGTGTCCGAAGCGCTTCATGCGTAGTGAC

CACCTGTCCCGTCACATCAAGACCCACCAGAATAAGAAGGGTGGATCC
                                                       BamHI

Veg1 amino acid sequence
                                              (SEQ ID NO: 11)
VPIPGKKKQHICHIQGCGKVYGTTSNLRRHLRWHTGERPFMCTWSYCGK

RFTRSSNLQRHKRTHTGEKKFACPECPKRFMRSDHLSRHIKTHQNKKGGS
```

Expression of Veg1

Expression of designed ZFPs was carried out in two different systems. In the first, the DNA-binding peptides were expressed in *E. coli* by inserting them into the commercially available pET15b vector (Novagen). This vector contains a T7 promoter sequence to drive expression of the recombinant protein. Constructs were introduced into *E. coli* BL21/DE3 (lacIq) cells, which contain an IPTG-inducible T7 RNA polymerase. Cultures were supplemented with 50 μM ZnCl2, were grown at 37° C. to an OD at 600 nm of 0.5-0.6, and protein production was induced with IPTG for 2 hrs. These proteins are referred to as "unfused" ZFPs.

Partially pure unfused ZFPs were produced as follows (adapted from Desjarlais et al. (1992) *Proteins: Structure, Function and Genetics* 12:101-104). A frozen cell pellet was resuspended in 1/50th volume of 1 M NaCl, 25 mM Tris-HCl (pH 8.0), 100 μM ZnCl$_2$, 5 mM DTT. Samples were boiled for 10 min and centrifuged for 10 min at ~3,000×g. At this point, ZFP protein in the supernatant was >50% pure (as estimated by staining of SDS-polyacrylamide gels with Coomassie blue), and the product migrated at the predicted molecular weight of around 11 kDa.

The second method for producing ZFPs was to express them as fusions to the *E. coli* Maltose Binding Protein (MBP). N-terminal MBP fusions to ZFPs were constructed by PCR amplification of the pET15b clones and insertion into the vector pMal-c2 (New England Biolabs) under the control of the Tac promoter. The fusion allows simple purification and detection of recombinant protein. It had been reported previously that zinc finger DNA-binding proteins can be expressed from this vector in soluble form to high levels in *E. coli* and can bind efficiently to the appropriate DNA target without refolding. Liu et al. (1997) *Proc. Natl. Acad. Sci. USA* 94:5525-5530. Production of MBP-fused proteins was as described by the manufacturer (New England Biolabs, Beverly, Mass.). Transformants were grown in LB medium supplemented with glucose and ampicillin, and were induced with IPTG for 3 hrs at 37° C. The cells were lysed by French press, then exposed to an agarose-based amylose resin, which specifically binds to the MBP moiety, thus acting as an affinity resin for the MBP fusion protein. The MBP fusion protein was eluted with 10 mM maltose to release ZFP of >50% purity. In some cases, protein was further concentrated using a Centricon 30 filter unit (Amicon).

Determination of Binding Affinity

Partially purified ZFPs (both unfused and MBP fusions) were tested by electrophoretic mobility shift assay (EMSA) to assess their ability to bind to their target DNA sequences. Protein concentrations were measured by Bradford assay (BioRad). Since SDS-polyacrylamide gels demonstrated >50% homogeneity of ZFP produced by either purification method, no adjustment was made for ZFP purity in the calculations. For this reason, the data generated by EMSA (shown below) represent an underestimate of the true affinity of the proteins for their targets (i.e., $K_d$ will be overestimated). In addition, inactive protein in the preparations could also contribute to an underestimate of the binding affinity of the active molecules in the preparation. Two separate preparations of protein were used for determination of $K_d$, to help control for differences in ZFP activity.

A 29-mer duplex oligonucleotide was used as a binding target for electrophoretic mobility shift analysis of Veg1. The sequence of the duplex (with VEGF sequences in bold and target site under/overlined) was as follows:

```
                                              (SEQ ID NO: 12)
5'-CATGCATAGCGGGGAGGATCGCCATCGAT-3'

3'-GTACGTATCGCCCCTCCTAGCGGTAGCTA-5'
```

The top strand was labeled, prior to annealing, with polynucleotide kinase and γ-$^{32}$P ATP. Top and bottom strands were annealed in a reaction containing each oligonucleotide at 0.5 μM, 10 mM Tris-HCl (pH 8.0), 1 mM EDTA, and 50 mM NaCl. The mix was heated to 95° C. for 5 min and slow-cooled to 30° C. over 60 min. Duplex formation was confirmed by polyacrylamide gel electrophoresis. Free label and single stranded DNA remaining in the target preparations did not appear to interfere with the binding reactions.

Assays for binding of Veg1 to the target oligonucleotide (above) were performed by titrating protein against a fixed amount of duplex target. Binding reactions contained 50 μM 5' $^{32}$P labeled double stranded target DNA, 10 mM Tris-HCl (pH 7.5), 100 mM KCl, 1 mM MgCl$_2$, 1 mM dithiothreitol, 10% glycercl, 200 μg/ml bovine serum albumin, 0.02% NP-40, 20 μg/ml poly dI-dC (optionally), and 100 μM ZnCl$_2$, in a final volume of 20 μl. Protein was added to the binding reaction as one-fifth volume from a dilution series made in 200 mM NaCl, 20 mM Tris (pH 7.5), 1 mM DTT. Binding was allowed to proceed for 45 min at room temperature. Polyacrylamide gel electrophoresis was carried out at room temperature using precast 10% or 10-20% Tris-HCl gels (BioRad, Hercules, Calif.) and Tris-Glycine running buffer (25 mM Tris-HCl, 192 mM glycine, pH 8.3) containing 0.1 mM ZnCl$_2$. Radioactive signals were quantitated with a Phosphorimager.

Figure 2:
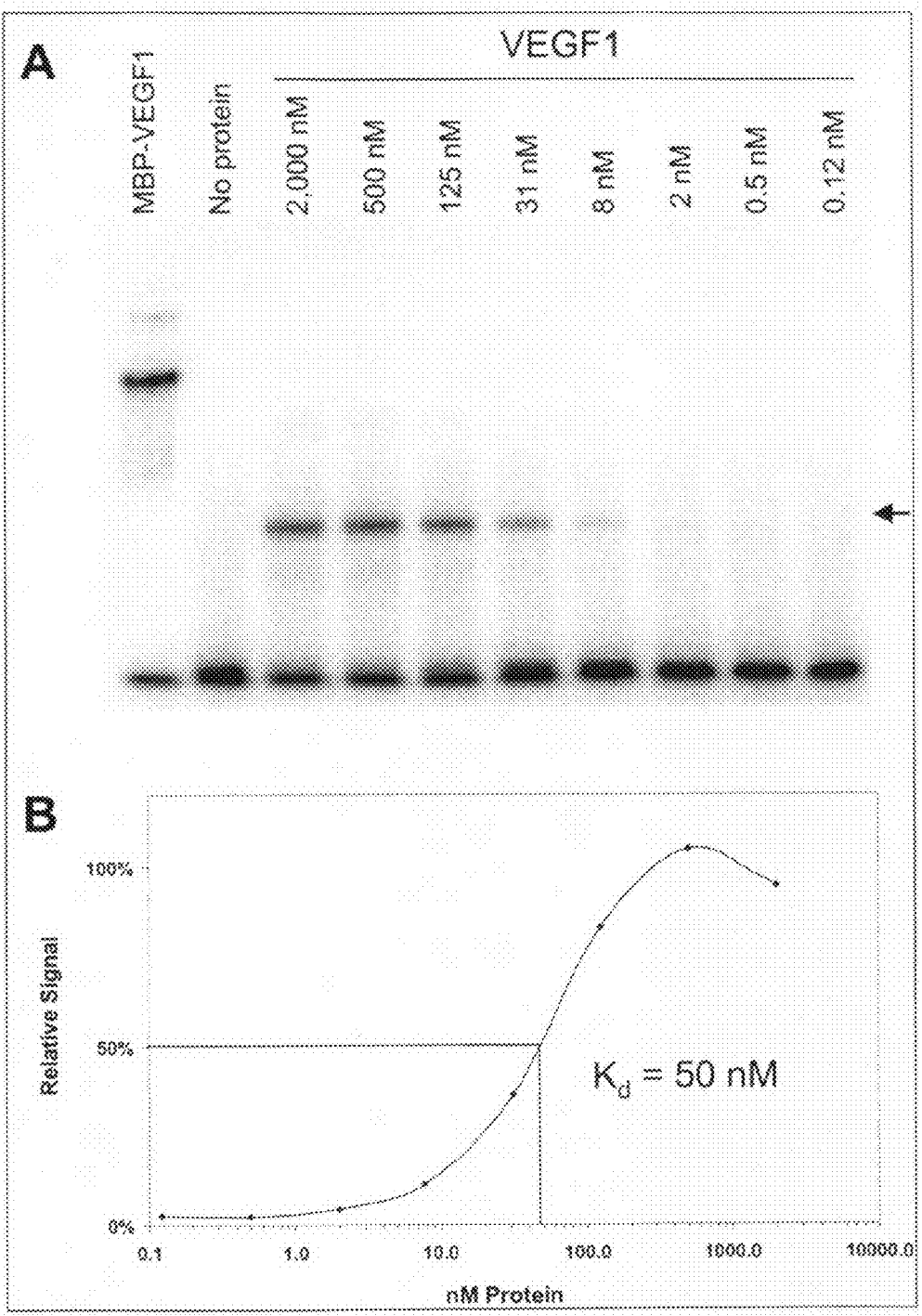
FIG. 2 shows the results of DNA-binding affinity determination for the Veg1 DNA-binding subdomain.

FIG. 2 shows the results of EMSA analysis of Veg1, using a four-fold dilution series of the Veg1 protein. Shifted product, indicative of labeled target with bound protein, is indicated by an arrow in FIG. 2A. The amount of shifted product was determined at each protein concentration and quantitated on a Phosphorimager (Molecular Dynamics). The relative signal (percent of maximal amount of shifted product) was plotted as a function of log$_{10}$ protein concentration. In this case, the protein concentration yielding half-maximal binding of Veg1 to its target site (i.e., the apparent $K_d$) was approximately 50 nM. MBP-fused and unfused versions of Veg1 bound to the target site with similar affinities.

Example 2

Construction of a Gene Encoding a Fusion Between the Veg1 DNA Binding Domain and hBAF 155

The Veg1 DNA, binding domain is subcloned into a eukaryotic expression vector, in such a way that it is fused to the hBAF155 subunit of the brm/BRG chromatin remodeling complex. First, a cDNA sequence encoding a full length BAF155 protein is cloned using long range PCR. Barnes (1994) *Proc. Natl. Acad. Sci. USA* 91:2216-2220; Cheng et al. (1994) *Proc. Natl. Acad. Sci. USA* 91:5695-5699. Reagents and enzymes for performing long-range PCR are available from Roche Molecular Biochemicals (Indianapolis, Ind.) under the name "Expand PCR System." The oligonucleotide primers are homologous to sequences just upstream of the translation initiation codon at nucleotide 55 and just downstream of the final codon (proline at nucleotide 3366). (The BAF155 numbering scheme refers to the Genbank Accession number U66615.) In addition, the primer upstream of nucleotide 55 contains a BamHI site positioned such that, when upstream sequences encoding the Veg1 DNA-binding domain are fused to BAF155 sequences, the translational reading frame is preserved. Furthermore, the primer downstream of nucleotide 3366 contains a HindIII site just downstream of the final codon of BAF155 positioned such that, if BAF155 sequences are fused to downstream sequences encoding a FLAG epitope tag, the translational reading frame is preserved.

PCR is performed using cDNA from HeLa cells as template. Amplified product having a size of approximately 3400 base pairs is gel-purified and cloned directly into a Topo2 cloning vector (Invitrogen, Carlsbad, Calif.). Site-directed mutagenesis is used to eliminate the BamHI site at BAF155 position 2304, without altering the coding capacity or translational reading frame of the gene. A similar approach is used to eliminate the KpnI sites at nucleotides 2235 and 3243, and the HindIII sites at nucleotides 656 and 2365. The cloned and modified BAF155 gene is then removed from the Topo2 vector by digestion with BamHI and HindIII, and gel-purified.

The expression vector is modified from pcDNA3.1(−) (Invitrogen, Carlsbad, Calif.), by digesting it with EcoRI and HindIII, and inserting a double-stranded oligonucleotide encoding an EcoRI site, a translation initiation sequence (Kozak (1991) *J. Biol. Chem.* 266:19,867-19,870), a nuclear localization signal (NLS), a KpnI site, a BamHI site and a HindIII site. The NLS is derived from the SV40 large T-antigen (Kalderon et al. (1984) *Cell* 39:499-509), and has the amino acid sequence MAPKKKRKVGIHGV (SEQ ID NO: 13).

This plasmid is then digested with BamHI and HindIII, and the BamHI-HindIII fragment comprising the BAF155 gene (supra) is inserted. A double-stranded oligonucleotide encoding a FLAG epitope (having the sequence DYKDDDDK, SEQ ID NO: 14), and containing HindIII sites at both ends is inserted concurrently with the BAF155-containing fragment. Alternatively, the FLAG-containing HindIII fragment can be inserted in a separate, subsequent ligation. The resulting construct comprises, in order, CMV immediate early promoter, EcoRI site, translation initiation sequence, SV40 large T-antigen nuclear localization sequence, KpnI site, BamHI site, hBAF155 coding sequence, HindIII site, FLAG epitope, HindIII site, bovine growth hormone (bGH) polyadenylation signal, in a pcDNA3.1 (Invitrogen, Carlsbad, Calif.) plasmid backbone. The CMV promoter and bGH polyadenylation signal are derived from the original pcDNA3.1 vector, as are sequences for replication and selection.

Next, the Veg1 ZFP DNA-binding domain (see Example 1) is inserted, as a KpnI-BamHI fragment, into the vector described in the preceding paragraph to generate a vector encoding a protein having the structure (from N- to C-terminus): Nuclear localization sequence—Veg1 DNA binding domain —HBAF155-FLAG epitope tag. The integrity of these constructs, and the preservation of the reading frame, is confirmed at each step of the procedure by nucleotide sequence analysis. Upon transfection into mammalian cells this vector produces a NLS-Veg1-BAF155-FLAG fusion, whose transcription is controlled by a CMV immediate early promoter and a bovine growth hormone polyadenylation signal.

Similar procedures are used to construct a plasmid encoding a fusion of a DNA-binding domain with any component of a chromatin remodeling complex. In brief, a polynucleotide encoding a component of a chromatin remodeling complex (or a functional fragment thereof) is obtained by PCR from cDNA (or optionally genomic DNA) using primers containing flanking BamHI and HindIII sites. BamHI, KpnI and HindIII sites, if present in the amplified product, are removed by site-directed mutagenesis, preserving the reading frame and coding capacity in the process. The amplified gene is introduced into a BamHI/HindIII-digested expression vector constructed as described above, optionally along with a HindIII fragment containing a FLAG epitope. The resulting construct is digested with KpnI and BamHI and a KpnI/BamHI fragment, encoding a DNA-binding domain, preferably a ZFP DNA-binding domain, is inserted. Sequences encoding nuclear localization sequences and FLAG epitopes, for immunological detection of the fusion protein, are optionally included in the construct.

Plasmids encoding these fusions are propagated in any suitable host strain, preferably *E. coli* strains JM109 or HB101.

Example 3

Design and Synthesis of a Six-finger ZFP DNA-binding Domain which Recognizes Target Sequences in the Human VEGF Gene Target Site A zinc finger DNA-binding domain, which recognizes the human vascular endothelial growth factor-A (VEGF) gene, was designed and constructed according to design rules and methods disclosed in co-owned WO 00/42219, WO 00/41566, and co-owned U.S. patent application Ser. No. 09/444,241 filed Nov. 19, 1999 and 09/535,088 filed Mar. 23, 2000. The target site, which overlaps the transcription initiation site for the human VEGF-A gene, is shown below as SEQ ID NO: 15, with the arrow indicating the transcription start-site.

```
              ↓
5'-GGGGAGGATCGCGGAGGCT-3'    (SEQ ID NO: 15)

3'-CCCCTCCTAGCGCCTCCGA-5'
```

Backbone Structure

Amino acids 533-624 of the human SP-1 zinc finger transcription factor were used as backbone for the construction of a designed six-finger DNA binding domain, Veg3a/1, capable of recognizing this sequence.

Amino acid sequences of the designed DNA-binding domains are illustrated in Table 1. As can be seen in the Table, the designed Veg3a/1 protein comprises two subdomains, Veg1 and Veg3a, each comprising three zinc fingers (F1, F2 and F3) and each recognizing a 9-base pair subsite of the target site, joined by the linker sequence DGGGS (SEQ ID NO: 16). The amino acid sequence of the recognition helix (positions −1 through +6, where +1 is the first amino acid in the α-helix) for each of the DNA-binding fingers is given in Table 1.

Sequences Encoding Veg1 and Veg3a Subdomains

Synthesis of the Veg1 binding domain was described in Example 1. Assembly of the Veg3a coding sequences was carried out as described above for Veg1 (Example 1 and FIG. 1) except that different specific oligonucleotides were used to encode the Veg3a recognition helices.

Accuracy of the Veg3a clone was verified by DNA sequencing. The Veg3a nucleotide and amino acid sequences are as follows.

```
Veg3a nucleotide sequence:
KpnI
                                           (SEQ ID NO: 17)
GGTACCCATACCTGGCAAGAAGAAGCAGCACATCTGCCACATCCAGGGCT

GTGGTAAAGTTTACGGCCAGTCCTCCGACCTGCAGCGTCACCTGCGCTGG

CACACCGGCGAGAGGCCTTTCATGTGTACCTGGTCCTACTGTGGTAAACG

CTTCACCCGTTCGTCAAACCTACAGAGGCACAAGCGTACACACACCGGTG

AGAAGAAATTTGCTTGCCCGGAGTGTCCGAAGCGCTTCATGCGAAGTGAC

GAGCTGTCACGACATATCAAGACCCACCAGAACAAGAAGGGTGGATCC
                                                BamHI
Veg3a amino acid sequence:
                                           (SEQ ID NO: 18)
VPIPGKKKQHICHIQGCGKVYGQSSDLQRHLRWHTGERPFMCTWSYCGK

RFTRSSNLQRHKRTHTGEKKFACPECPKRFMRSDELSRHIKTHQNKKG

GS.
```

The recognition regions of the Veg3a polypeptide (amino acids −1 through +6 of the zinc finger recognition helices) are shown in bold underline.

Determination of Veg3a Binding Affinity

The purified Veg3a zinc finger DNA-binding domain is tested for affinity to its DNA target site by electrophoretic mobility shift analysis. A double-stranded target oligonucleotide was constructed by annealing complementary 29-mers, then end-labeled using polynucleotide kinase and γ-$^{32}$P-ATP. The sequence of the target (with VEGF sequences in bold and target sites under/overlined) was as follows:

```
                                           (SEQ ID NO: 19)
5'-CATGCATATCGCGGAGGCTTGGCATCGAT-3'

3'-GTACGTATAGCGCCTCCGAACCGTAGCTA-5'
```

Fusion of Veg1 and Veg3a Subdomains to form a Veg3a/1 Binding Domain

Veg1 and Veg3a binding subdomains were joined to each other, using the linker sequence DGGGS (SEQ ID NO: 16). This particular linker sequence was chosen because it permits binding of two three-finger ZFP binding subdomains to two 9-bp sites that are separated by a one nucleotide gap, as is the case for the Veg1 and Veg3a sites. See also Liu et al., supra.

The 6-finger Veg3a/1 protein encoding sequence was generated as follows. Sequences encoding Veg3a recognition helices were PCR-amplified from the Veg3a-encoding vector (supra) using the primers SPE7 (5'-GAGCA GAATTCGGCAAGAAGAAGCAGCAC) (SEQ ID NO: 20) and SPEamp12 (5'-GTGG TCTAGACAGCTCGTCACTTCGC) (SEQ ID NO: 21) to generate a double-stranded fragment bounded by EcoRI and XbaI restriction sites (underlined in the sequences of the primers). The amplification product was digested with EcoRI and XbaI. Sequences encoding Veg1 recognition helices were PCR-amplified from the Veg1-encoding vector (Example 1) using the primers SPEamp13 (5'-GGAG CCAAGGCTGTGGTAAAGTTTACGG) (SEQ ID NO: 22) and SPEamp11 (5'-GGAG AAGCTTGGATCCTCATTATCCC) (SEQ ID NO: 23) to generate a double-stranded amplification product bounded by StyI and HindIII restriction sites (underlined in the sequences of the primers). The resulting amplification product was digested with StyI and HindIII. A third double-stranded fragment was constructed, using synthetic oligonucleotides, which encodes the DGGGS linker, flanked by the remainders of the Veg1 and Veg3a DNA-binding domains, and bounded by XbaI and StyI sites. The sequence of this third fragment is as follows, with the XbaI and StyI sites underlined:

```
    XbaI
                                           SEQ ID NO: 24
5'  CTAGACACATCAAAACCCACCAGAACAAGAAAGACGGCGGTGGC

AGCGGCAAAAAGAAACAGCACATATGTCACATC 3'

SEQ ID NO: 25
3'  TGTGTAGTTTTGGGTGGTCTTGTTCTTTCTGCCGCCACCGTCGC

CGTTTTTCTTTGTCGTGTATACAGTGTAGGTTC 5'
                                                StyI
```

These three fragments were ligated to one another, the ligation product was amplified with primers SPE7 and SPEamp11, and the resulting amplification product was digested with EcoRI and HindIII and cloned into the EcoRI and HindIII sites of pUC19.

The linked Veg3a- and Veg1-encoding sequence, in the pUC19 backbone, was then amplified with the primers GB 19 (5'-GCCATGCC GGTACCCATACCTGGCAAGAAGAAGCAGCAC) (SEQ ID NO: 26) and GB10 (5'-CAGATC GGATCCACCCTTCTTATTCTGGTGGGT (SEQ ID NO: 27) to introduce KpnI and BamHI sites at the ends of the amplification products (restriction sites underlined). The amplification products were then digested with KpnI and BamHI, and cloned into the modified pMAL-c2 expression vector described above.

The nucleotide sequence encoding the designed 6-finger ZFP Veg3a/1, from the KpnI site to the BamHI site is:

```
                                           (SEQ ID NO: 28)
GGTACCCATACCTGGCAAGAAGAAGCAGCACATCTGCCACATCCAGGGCT

GTGGTAAAGTTTACGGCCAGTCCTCCGACCTGCAGCGTCACCTGCGCTGG

CACACCGGCGAGAGGCCTTTCATGTGTACCTGGTCCTACTGTGGTAAACG

CTTCACACGTTCGTCAAACCTACAGAGGCACAAGCGTACACACACAGGTG

AGAAGAAATTTGCTTGCCCGGAGTGTCCGAAGCGCTTCATGCGAAGTGAC

GAGCTGTCTAGACACATCAAAACCCACCAGAACAAGAAAGACGGCGGTGG

CAGCGGCAAAAAGAAACAGCACATATGTCACATCCAAGGCTGTGGTAAAG
```

-continued

```
TTTACGGCACAACCTCAAATCTGCGTCGTCACCTGCGCTGGCACACCGGC

GAGAGGCCTTTCATGTGTACCTGGTCCTACTGTGGTAAACGCTTCACCCG

TTCGTCAAACCTGCAGCGTCACAAGCGTACCCACACCGGTGAGAAGAAAT

TTGCTTGCCCGGAGTGTCCGAAGCGCTTCATGCGTAGTGACCACCTGTCC

CGTCACATCAAGACCCACCAGAATAAGAAGGGTGGATCC
```

The VEGF3a/1 amino acid sequence (using single letter code) is:

```
                                            (SEQ ID NO: 29)
VPIPGKKKQHICHIQGCGKVYGQSSDLQRHLRWHTGERPFMCTWSYCGKR

FTRSSNLQRHKRTHTGEKKFACPECPKRFMRSDELSRHIKTHQNKKDGGG

SGKKKQHICHIQGCGKVYGTTSNLRRHLRWHTGERPFMCTWSYCGKRFTR

SSNLQRHKRTHTGEKKFACPECPKRFMRSDHLSRLHIKTHQNKKGGS
```

The Veg3a/1 protein was expressed in *E. coli* as an MBP fusion, purified by affinity chromatography, and tested in EMSA experiments as described supra. A labeled double-stranded oligonucleotide comprising the target site was prepared by synthesis and annealing of two overlapping oligonucleotides, one of which was labeled with $^{32}$P. The oligonucleotides comprised the following sequences (with the target site over/underlined):

```
                                         (SEQ ID NO: 30)
AGCGAGCGGGGAGGATCGCGGAGGCTTGGGGCAGCCGGGTAG (SEQ ID NO: 31)
TCGCCCCTCCTAGCGCCTCCGAACCCCGTCGGCCCATCTCGC
```

Binding analysis was conducted as described in Example 1 for the Veg1 protein. Binding was allowed to proceed for 60 min at either room temperature or 37° C., and polyacrylamide gel electrophoresis was carried out at room temperature or 37° C. using precast 10% or 10-20% Tris-HCl gels (BioRad) and standard Tris-Glycine running buffer. The room temperature assays yielded an apparent $K_d$ (determined as described supra) for this Veg3a/1 protein of approximately 1.5 nM. When binding and electrophoresis were performed at 37° C., the apparent $K_d$ of Veg3a/1 was approximately 9 nM when tested against the 18-bp target. Thus, the six finger Veg3a/1 ZFP bound with high affinity to its target site.

Example 4

Construction of a Gene Encoding a Fusion between a ZFP DNA Binding Domain and a Methyl-binding Domain Protein A plasmid encoding a fusion between the human MBD1 gene and the Veg3a/1 DNA-binding domain is constructed using methods similar to those described above for the BAF155 Veg1 fusion (Example 2). Sequences encoding MBD1 (GenBank accession No. NM015846) are isolated by PCR from genomic DNA or cDNA. Amplification primers are designed such that the primer corresponding to the upstream region of the gene comprises a BamHI Site at or near its upstream terminus, and the primer corresponding to the downstream region of the gene comprises a HindIII site at or near its downstream terminus. The primers are designed to amplify the region between nucleotides 140 (MBD1 initiation codon) and 1,957 (MBD1 termination codon), and to retain the correct reading frame of the MBD1 gene when the amplification product is incorporated as a component of a fusion gene. The amplification product is optionally cloned, a BamHI site at nucleotide 264 of the MBD1 sequence is removed by site-specific mutagenesis, and the BamHI/HindIII fragment is released from the cloning vector and purified. Sequences encoding the Veg3a/1 DNA-binding domain are obtained as a KpnI/BamHI fragment (Example 3). The MBD1-encoding BaHI/HindIII fragment and the Veg3a/1-coding KpnI/BamHI fragment are inserted into pcDNA3.1(−) or a modified derivative (Example 2). A nuclear localization signal and/or a FLAG epitope are optionally included in the fusion construct.

The MBD1 gene can be divided into at least two functional fragments: a methylated DNA binding domain (encoded by nucleotides 158-322) and a functional domain. Accordingly, a MBD/ZFP fusion gene is constructed that lacks sequences encoding the methylated DNA-binding domain, but contains the functional domain of the MBD1 protein. In this case, the BamHI/HindIII-terminated amplification product comprises nucleotides 322 through 1,957 of the MBD1 gene.

A similar fusion gene is constructed, in which the MBD2 gene (GenBank accession No. NM003927), or a functional fragment thereof, is fused to a ZFP DNA-binding domain. In this case, the amplification primers are designed to amplify the region between nucleotides 230 (MBD2 initiation codon) and 1,465 (MBD2 termination codon), and to retain the correct reading frame of the MBD2 gene when the amplification product is incorporated as a component of a fusion gene. The amplification product is optionally cloned, a KpnI site at nucleotide 813 and a HindIII site at nucleotide 1308 of the MBD 1 sequence are removed by site-specific mutagenesis, and the BamHI/HindIII fragment is released from the cloning vector and purified. Sequences encoding the Veg3a/1 DNA-binding domain are obtained as a KpnI/BamHI fragment (Example 3). The MBD2-encoding BamHI/HindIII fragment and the Veg3a/1-coding KpnI/BamHI fragment are inserted into pcDNA3.1 (−) or a modified derivative (Example 2). A nuclear localization signal and/or a FLAG epitope are optionally included in the fusion construct.

The methylated DNA-binding domain of the MBD2 gene is encoded by nucleotides 680-862. Accordingly, a MBD/ZFP fusion gene is constructed that lacks sequences encoding the methylated DNA-binding domain, but contains the functional domain of the MBD2 protein, by designing the amplification primers to amplify the region of the MBD2 gene located between nucleotides 862 and 1,465. As in previous examples, the amplification primers comprise BamHI and HindIII sites at or near their termini, to maintain the MBD2 reading frame and facilitate construction of the fusion protein by the methods described supra. In this case, the HindIII site at nucleotide 1,308 is removed subsequent to amplification and prior to construction of the fusion nucleic acid.

Example 5

Introduction of Fusion Molecules into Cells

Human embryonic kidney cells (HEK 293) are grown in DMEM (Dulbecco's modified Eagle medium) supplemented with 10% fetal calf serum. Cells are plated in 10 cm dishes at a density of $2.5 \times 10^6$ per plate and grown for 24 hours in a $CO_2$ incubator at 37° C. For transfection, 10 µg of plasmid DNA is diluted in 2.5 ml Opti-MEM (Life Technologies), and 50 µl of Lipofectamine 2000 is diluted in 2.5 ml Opti-MEM. The diluted DNA and lipid are mixed and incubated for 20 minutes at room temperature. Medium is then removed from the cells and replaced with the lipid/DNA mixture. Cells are incubated at 37° C. for 3 hours in a $CO_2$ incubator, then 10 ml of DMEM+10% FBS is added. Cells are harvested 40 hours after transfection for analysis of chromatin structure (Example 6) and gene expression (Example 7).

Intercalator-protein fusions, MGB-protein fusions and/or TFO-protein fusions are introduced into cells after encapsulation into liposomes, using standard procedures that are well-known in the art.

Example 6

Assays for Chromatin Remodeling

Recruitment of a chromatin remodeling complex to a region of interest in cellular chromatin, by a fusion molecule comprising a DNA-binding domain and a component of a chromatin remodeling complex, is evidenced by alteration of chromatin structure in the region of interest. Alteration of chromatin structure mediated by the Veg1-BAF155 fusion molecule described supra (Example 2) is assessed by investigating nuclease hypersensitive sites in the vicinity of the Veg1 binding site, as described in this example.

Cell Growth and Isolation of Nuclei for Studies of Nuclease Hypersensitivity

Transformed human embryonic kidney 293 cells are grown in DMEM+10% fetal calf serum, supplemented with penicillin and streptomycin, in a 37° C. incubator at 5% $CO_2$. Typically, two 255 $cm^2$ plates of cells are used in an experiment. When the cells reach greater than 90% confluence (~$2.5 \times 10^7$ cells per plate), medium is removed and the cells are rinsed twice with 5 ml of ice-cold PBS (Gibco/Life Technologies, Gaithersburg, Md.). Cells are then scraped from the plates in 5 ml of ice-cold PBS and combined in a 50 ml conical centrifuge tube. The plates are washed with 10 ml of ice-cold PBS and the washes are added to the tube. Nuclei are pelleted by centrifugation (1400 rpm for 5 min) and the supernatant is removed. The pellet is mixed by vortexing and, while vortexing, 20 ml of lysis buffer (10 mM Tris pH 7.5, 1.5 mM $MgCl_2$, 10 mM KCl, 0.5% IGEPAL CA-630 (Sigma), 1 mM phenylmethylsulfonyl fluoride, 1 mM dithiothreitol) is added. The cell pellet is resuspended in lysis buffer by pipetting and the tube is centrifuged at 1400 rpm for 5 min. The supernatant is removed and the pellet is resuspended in 20 ml of lysis buffer and centrifuged as before. The final pellet is resuspended in 1.5 ml dilution buffer (15 mM Tris pH 7.5, 60 mM KCl, 15 mM NaCl, 5 mM $MgCl_2$, 0.1 mM dithiothreitol, 10% glycerol), nuclei are counted in a microscope and the solution is adjusted so that a concentration of approximately $10^7$ nuclei per ml is obtained.

DNase Treatment of Nuclei

Nuclei, at a concentration of $10^7$ per ml in dilution buffer, are digested with different concentrations of DNase I. DNase I dilutions are prepared by diluting deoxyribonuclease I (Worthington, Freehold, N.J.) in dilution buffer (supra), optionally supplemented with 0.4 mM $CaCl_2$. To 100 μl of resuspended nuclei is added 25 μl of a DNase I dilution to give final DNase I concentrations ranging from 0.07 Units/ml to 486 Units/ml in three-fold concentration increments. Digestions are conducted at room temperature for 5 min. Digestion reactions are then stopped by addition of 125 μl of Buffer AL (Qiagen DNeasy™ Tissue Kit) and 12.5 μl of a 20 mg/ml solution of Proteinase K (Qiagen DNeasy™ Tissue Kit), followed by incubation at 70° C. for 10 min. Digested DNA is purified using the DNeasy™ Tissue Kit (Qiagen, Valencia, Calif.) according to the manufacturer's instructions.

Purified DNase-treated DNA is digested with restriction enzyme at 37° C. overnight with 40 Units of restriction enzyme in the presence of 0.4 mg/ml RNase A. After digestion, DNA is ethanol-precipitated from 0.3 M sodium acetate.

Micrococcal nuclease can be used as an alternative to DNase I for examination of chromatin structure. Treatment of nuclei, obtained as described supra, with micrococcal nuclease is conducted as described by Livingstone-Zatchej et al. in *Methods in Molecular Biology*, Vol. 119, Humana Press, Totowa, N.J., pp. 363-378.

Treatment of Nuclei with a Chemical Probe

Nuclei are treated with MPE using the following procedure adapted from Cartwright et al., supra. A freshly-diluted stock of 0.4 M $H_2O_2$ is prepared by making a 25-fold dilution of a 30% stock solution. A freshly-prepared stock of 0.5 M ferrous ammonium sulfate is diluted 400-fold in water. A solution of methidiumpropyl EDTA (MPE) is prepared by adding 30 μl of 5 mM MPE to 90 μl of water. To this MPE solution is added 120 μl of the ferrous ammonium sulfate dilution and 2.5 μl of 1 M dithiothreitol (DTT, freshly prepared from powder). To a suspension of nuclei, obtained as described supra, are added, in sequence: 3.5 μl of 0.4 M $H_2O_2$ and 37.5 μl of the MPE/ferrous ammonium sulfate/DTT mixture. The reaction is terminated after an appropriate time period (determined empirically) by addition of 40 μl of 50 mM bathophenanthroline disulfonate, 0.1 ml of 2.5% sodium dodecyl sulfate/50 mM EDTA/50 mM Tris-Cl, pH 7.5 and 10 μl of Proteinase K (10-14 mg/ml). Proteinase digestion is conducted at 37° C. for at least 8 hours and the mixture is then extracted twice with phenol/chloroform and once with chloroform. Nucleic acids are precipitated from the aqueous phase by addition of sodium acetate to 0.3 M and 0.7 volume of isopropyl alcohol, incubation on ice for at least 2 hr, and centrifugation. The pellet is washed with 70% ethanol, dried, resuspended in 10 mM Tris-Cl, pH 8 and treated with RNase A (approximately 0.1 mg/ml) for 15 min at 37° C.

Blotting and Hybridization

Pellets of precipitated, digested DNA, obtained after treatment with enzymatic or chemical probes as described supra, are resuspended in 22 μl of loading buffer containing glycerol and tracking dyes ("Gel loading solution," Sigma Chemical Corp., St. Louis, Mo.) and incubated at 55° C. for 3-4 hours. Twenty microliters of resuspended sample is loaded onto a 1% agarose gel containing 1×TAE buffer and 0.5 μg/ml ethidium bromide, and electrophoresis is conducted at 22 Volts for 16 hours in Tris-acetate-EDTA buffer. After electrophoresis, the gel is treated with alkali, neutralized, blotted onto a Nytran membrane (Schleicher & Schuell, Keene, N.H.), and the blotted DNA is crosslinked to the membrane by ultraviolet irradiation.

Probes are labeled by random priming, using the Prime-It Random Primer Labeling Kit (Stratagene, La Jolla, Calif.) according to the manufacturer's instructions. In a typical labeling reaction, 25-50 ng of DNA template is used in a final volume of 50 μl. A specific activity of $10^9$ cpm/μg is typically obtained. Labeled probes are purified on a NucTrap probe column (Stratagene #400702, La Jolla, Calif.). The membrane is placed in a hybridization bottle and pre-hybridized in Rapid Hybridization Buffer (Amersham, Arlington Heights, Ill.) at 65° C. for 15 min. Probe (a 0.1 kb XbaI-KpnI fragment, see FIG. 1A) is added (approximately 0.03 μg containing approximately $3.3 \times 10^7$ cpm) and hybridization is conducted at 65° C. for 2 hours. Following hybridization, the membrane is washed once at 65° C. for 10 min. with 2×SSC+0.1% SDS, and twice at 65° C. for 10 min. with 0.1×SSC+0.1% SDS. The membrane is then dried and analyzed either by autoradiography or with a phosphorimager.

Figure 3:
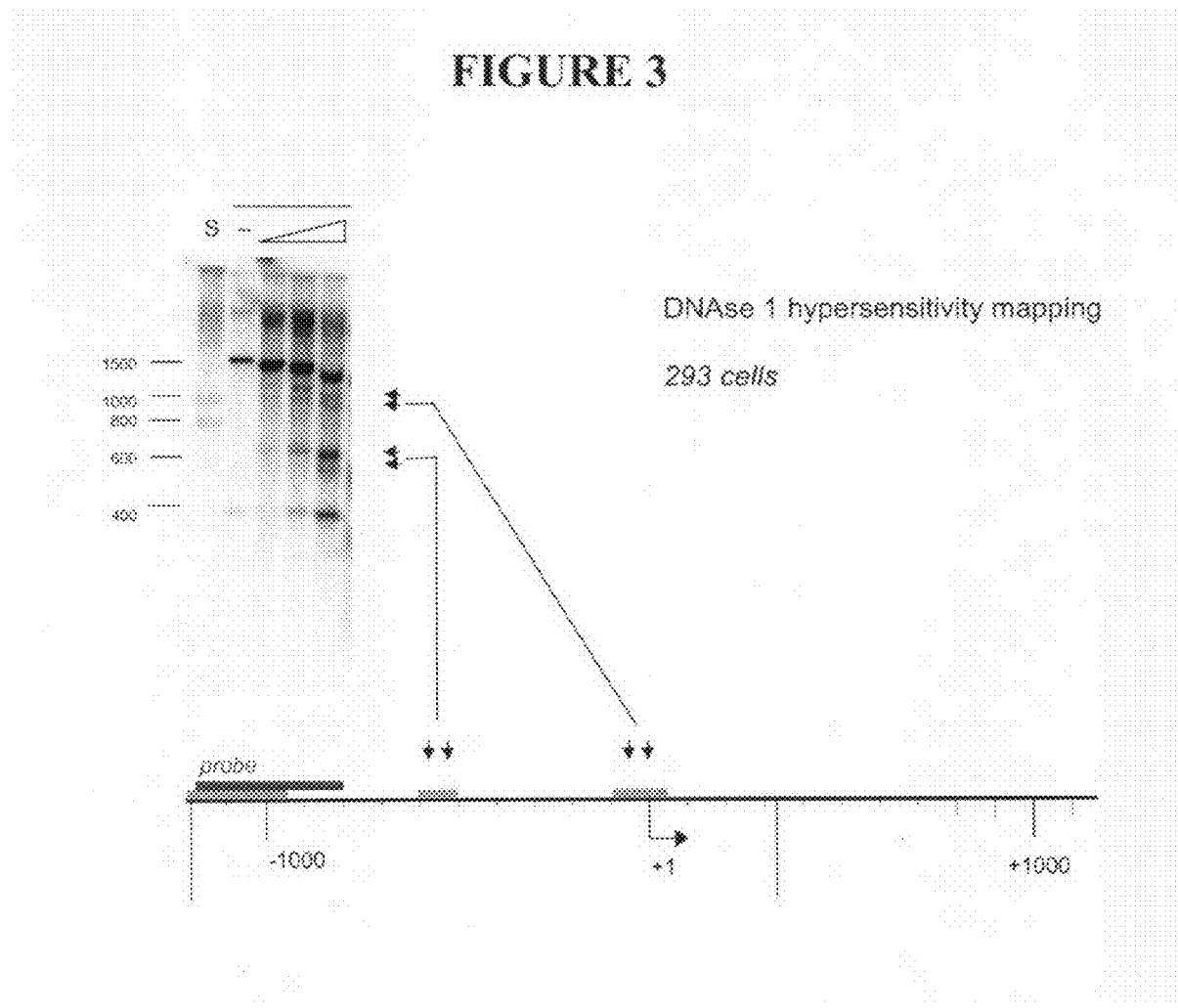
FIG. 3 shows an autoradiogram of a DNA gel, indicating the existence and location of DNaseI-hypersensitive sites in the human VEGF-A gene.

Results are shown in FIG. 3 for analysis of DNase hypersensitivity, in HEK293 cells, within an approximately 1,000 base-pair region upstream of the human VEGF-A gene transcriptional startsite. Increasing DNase concentration resulted in the generation of two new sets of DNA fragment doublets, centered at approximately 500 and 1,000 nucleotides, indicating the presence of two DNase hypersensitive regions. One of these regions is centered approximately 500 base pairs upstream of the transcriptional startsite; the other is centered on the transcriptional startsite.

Remodeling of VEGF chromatin can involve, among other things, loss of one or both of these hypersensitive regions, or the generation of one or more additional hypersensitive regions, either upstream or downstream of the transcriptional startsite.

Example 7

Assays for Modulation of Gene Expression

General. Activation or repression of transcription resulting from localized chromatin remodeling is determined by measurement of RNA and/or protein gene products. These methods are well-known to those of skill in the art.

For example, Mizuguchi et al (1999) in *Methods in Molecular Biology*, Vol. 119, "Chromatin Protocols" (P. B. Becker, ed.) Humana Press, Totowa, 1999, pp. 333-342 describe a procedure for in vitro transcription of chromatin that has been remodeled by the *Drosophila* NURF complex. This assay can be used to detect changes in transcriptional properties of chromatin (either activation or repression) following chromatin remodeling.

Production and specificity of RNA can also be measured by RNA blots, nuclease protection and/or quantitative real-time PCR (colloquially known as the "Taqman" assay), as is known to those of skill in the art. See, for example, Ausubel et al., supra.

Protein production can be measured by immunoassay (e.g., ELISA, immunoprecipitation), gel electrophoresis, and/or immunological detection of protein blots ("Western" blots), as is known to those of skill in the art. See, for example, Ausubel et al., supra.

Reporter genes, either chromosomal or extrachromosomal, can also be used to assay activation and/or repression of specific promoters. Accordingly, effect of chromatin remodeling on a promoter that is operatively linked to a reporter gene (such as, for example, alkaline phosphatase, β-galactosidase, β-glucuronidase, chloramphenicol acetyl transferase, horseradish peroxidase, luciferase, or green fluorescent protein) can be assayed by measuring the levels and/or activity of the reporter. Methods for fusion of a promoter to a reporter gene, and methods for assay of reporter gene products, are known to those of skill in the art. See, for example, Ausubel et al., supra.

RNA analysis. Transient transfection of HEK293 cells, seeded in 6-well plates, is carried out as described in Example 6, supra. Cell lysates are harvested 40 hours post-transfection. To assay the activation of the endogenous chromosomal VEGF gene, RNA blotting ("Northern" blotting) is used to measure VEGF mRNA levels. Briefly, PolyA+ RNA is isolated from HEK 293 cells transfected with a fusion plasmid or from mock-transfected HEK293 cells, using the Oligotex kit (Qiagen, Valencia, Calif.), according to the manufacturer's instructions. The fusion plasmid encodes a fusion protein comprising a nuclear localization sequence, the Veg1 DNA-binding domain, BAF155 and a FLAG epitope (see Example 2, supra). 71 g of RNA are resolved on a 2.4% agarose gel containing 2.4 M formaldehyde, and the gel is blotted onto Nytran SuPerCharge membrane (Schliecher & Schuell, Keene, N.H.) using 20×SSC. The membrane is hybridized at 65° C. for 1 hour in Rapid-Hyb Buffer (Amersham-Pharmacia Biotech, Piscataway, N.J.) containing a $^{32}$P-labeled VEGF cDNA probe. The VEGF cDNA construct is generated by inserting a human VEGF cDNA fragment, obtained by PCR amplification, into the pcDNA3.1 vector (Invitrogen, Carlsbad Calif.) at the XbaI and EcoRI sites. Structure of the clone is confirmed by sequencing. After hybridization, the VEGF probe is stripped from the membrane, and the blot is re-hybridized with a $^{32}$P labeled GAPDH DNA probe. VEGF mRNA levels, as determined by RNA blotting, are normalized to GAPDH mRNA levels.

For real-time quantitative PCR ("Taqman") analysis of mRNA abundance, total cellular RNA from transfected HEK 293 cells is isolated using the Rneasy Kit (Qiagen, Valencia, Calif.). RNA samples (25 ng) are mixed with 0.3 μM of each primer, 0.1 μM of probe, 5.5 mM $MgCl_2$, 0.3 mM of each dNTP, 0.625 unit of AmpliTaq Gold RNA Polymerase, 6.25 units of Multiscribe Reverse Transcriptase, and 5 units of RNase inhibitor, in Taqman buffer A from Perkin Elmer. Reverse transcription is performed at 48° C. for 30 min. After denaturing at 95° C. for 10 minutes, PCR is conducted for 40 cycles at 95° C. for 15 seconds and 60° C. for one minute. Analysis is conducted, during the amplification reaction, in a 96-well format on an ABI 7700 SDS machine (PE BioSystems, Foster City, Calif.) and data is analyzed with SDS version 1.6.3 software. Exemplary probes and primers for analysis of VEGF and GAPDH genes are presented in Table 2.

TABLE 2

| | Primer and Probe sequences for hydrolyzable probe analysis | | |
|---|---|---|---|
| Gene | Forward primer | Reverse primer | Probe |
| VEGF | 5'-CTGGTAGCGGG GAGGATCG-3' (SEQ ID NO: 32) | 5'-GCCACGACCTC CGAGCTAC-3' (SEQ ID NO: 33) | 5'-CTACCCGGCTG CCCCAAGCCTC-3' (SEQ ID NO: 34) |
| GAPDH | 5'-CCTTTTGCAGA CCACAGTCCA-3' (SEQ ID NO: 35) | 5'-GCAGGGATGAT GTTCTGGAGA-3' (SEQ ID NO: 36) | 5'-CACTGCCACCC AGAAGACTGTGG-3' (SEQ ID NO: 37) |

Protein analysis. Analysis of protein levels is performed by resolving 10 μg of whole cell lysate on a 10-20% polyacrylamide gel run in Tris/glycine/SDS buffer (BioRad, Hercules, Calif.). Proteins separated in the gel are transferred onto a nitrocellulose membrane using Tris/glycine/SDS buffer supplemented with 20% methanol, and the filter is blocked with 5% non-fat dry milk for 1 hour at room temperature. The blot is probed for 1 hour at room temperature with anti-Flag M2 monoclonal antibody (Sigma, St. Louis, Mo.) diluted 1:1000 in 5% (w/v) non-fat dry milk/0.1% PBS-Tween, then washed twice for 5 sec and once for 15 min with 0.1% PBS-Tween. All washes are performed at room temperature. The blot is then incubated for one hour at room temperature with a horseradish peroxidase-conjugated anti-mouse antibody (Amersham-Pharmacia Biotech, Piscataway, N.J.), used at a 1:3000 dilution in 5% (w/v) non fat dry milk/0.1% PBS Tween. This is followed by two 5 sec washes and one 15 min wash with 0.1% PBS-Tween. Protein bands are detected using the ECL system (Amersham-Pharmacia Biotech, Piscataway, N.J.).

For analysis of protein level by ELISA, cell lysates are prepared (as described above) or culture medium is harvested and analyzed using a commercially available ELISA kit. For example, levels of secreted VEGF protein are determined by assay of culture medium using a human VEGF ELISA kit (R & D systems, Minneapolis, Minn.).

Results. Transfection of the Veg1/hBAF155 fusion construct (Example 2) into cultured HEK 293 cells results in activation of VEGF gene expression, compared to untransfected cells, as evidenced by increases in VEGF mRNA and protein levels. Vectors lacking the ZFP and/or BAF155 portions of the fusion are used as controls. Transfection efficiency is measured by co-transfection of a green fluorescent protein expression vector. A mock transfection control is also carried out.

Introduction of the Veg3a/1-MBD1 or Veg3a/1-MBD2 fusion construct into cultured HEK 293 cells by transfection results in repression of VEGF gene expression, compared to untransfected cells, as evidenced by decreases in VEGF mRNA and protein levels. Controls similar to those described above are also conducted.

Example 8

Assays for Chromatin Remodeling Complexes

Methods for the purification, assay and characterization of various chromatin remodeling complexes are well-known to those of skill in the art. See, for example, Methods in Enzymology, Vol. 304, "Chromatin" (P. M. Wassarman and A. P. Wolffe, eds.), Academic Press, San Diego, 1999; and Methods in Molecular Biology, Vol. 119, "Chromatin Protocols" (P. B. Becker, ed.) Humana Press, Totowa, 1999.

Chromatin remodeling can take the form of, for example, deposition, removal or repositioning of nucleosomes within chromatin. Means for detecting chromatin remodeling include, but are not limited to, detecting changes in accessibility of specific sites in chromatin to sequence-specific nucleases such as restriction enzymes, determination of the appearance or disappearance of a regularly repeating pattern of chromatin digestion by non-sequence specific endonucleases such as micrococcal nuclease and DNase I, determination of nucleosome spacing, and nucleosome-binding assays. Also, as mentioned supra, chromatin remodeling complexes possess ATPase activity; therefore ATP hydrolysis assays can be used in the identification and/or characterization of chromatin remodeling complexes.

Restriction endonuclease accessibility assays are described by Logie et al., supra and Varga-Weisz et al. (1999) Meth. Enzymology 304:742-757. Assays for nucleosome spacing, DNase I accessibility, ATPase activity and nucleosome binding are disclosed by Varga-Weisz et al., supra. Assays to detect facilitation of transcription factor binding are described by Cote et al. (1994) Science 265:53-60 and Kwon et al. (1994) Nature 370:477-481. Assays for nucleosome repositioning (i.e., "sliding") are disclosed by Hamiche et al. (1999) Cell 97:833-842.

These assays, and others, can be used for the purification and characterization of chromatin remodeling complexes from various species, for example, the yeast SWI/SNF complex (Logie et al., supra), the *Drosophila* CHRAC complex (Varga-Weisz et al., supra) and the *Drosophila* NURF complex (Sandaltzopoulos et al., supra).

Example 9

ATPase Assay

Chromatin remodeling complexes utilize the energy of ATP hydrolysis to modify chromatin structure. Consequently, nucleosome- or DNA-dependent ATPase activity can be used to assay for a chromatin remodeling complex.

Methods and compositions for conducting ATPase assays are well-known to those of skill in the art. One measure of ATPase activity is the release of labeled pyrophosphate from $\gamma$-$^{32}$P-labeled ATP. Release is measured as the amount of radioactivity that does not bind to activated charcoal in 20 mM phosphoric acid.

An alternative method for measuring pyrophosphate release is to measure labeled pyrophosphate directly by thin layer chromatography. The reaction mixture contains 0.02 μg/ml DNA (or reconstituted nucleosomal array, see Example 11 infra), 5 nM SWI/SNF complex (or any other known or putative chromatin remodeling complex), 20 mM Tris, pH 8.0, 5 mM MgCl$_2$, 0.2 mM dithiothreitol, 0.1% Tween, 5% glycerol, 100 μg/ml bovine serum albumin, 100 μM ATP, and 0.2 μCi ($\gamma$-$^{32}$P)ATP (3 Ci/mmol) in a final volume of 20 μl and is incubated at 37° C. At the conclusion of the assay (under these conditions the reaction rate is linear for 5-10 minutes), 1 μl is pipetted onto a polyethyleneimine cellulose sheet and the sheet is developed in a solution of 0.75 M potassium phosphate, pH 3.5. In this system, ATP and pyrophosphate are clearly resolved from each other and from the origin. Quantitation is carried out either by autoradiography followed by excision and scintillation counting of labeled spots, or by phosphorimaging.

The preceding methods are adapted from those described by Logie et al. (1999) Meth. Enzymology 304:726-741.

An alternative solvent for thin-layer chromatography is 0.5 M LiCl/1 M formic acid. In this system, pyrophosphate is separated from unhydrolyzed ATP, which remains at the origin. Varga-Weisz et al. (1999) Meth. Enzymol. 304:742-757.

Example 10

Preparation of Reconstituted Nucleosome Arrays

Deposition of purified histone octamers onto a specific template under defined conditions can generate a nucleosomal array in which the positions of one or more individual nucleosomes, with respect to the nucleotide sequence of the template, are known. Such an array can be used as a substrate in an assay for chromatin remodeling activity, by testing for changes in nucleosome position with respect to nucleotide sequence. One such test is restriction endonuclease accessibility. See infra.

Preparation of reconstituted nucleosome arrays can be conducted according to Logie et al., supra and Varga-Weisz et al., supra. Additional methods can be found in *Methods in Enzymology*, Vol. 304, "Chromatin" (P. M. Wassarman and A. P. Wolffe, eds.), Academic Press, San Diego, 1999; and *Methods in Molecular Biology*, Vol. 119, "Chromatin Protocols" (P. B. Becker, ed.) Humana Press, Totowa, 1999.

Example 11

Construction of a Gene Encoding a Fusion Between a ZFP Binding Domain and the ISWI Chromatin Remodeling ATPase ISWI-encoding sequences were amplified from a recombinant plasmid encoding *Drosophila* ISWI. Corona et al.

(1999) *Mol. Cell.* 3:239-245. One of the primers contained, outside of the ISWI-complementary region, sequences encoding a FLAG epitope and, at the 5' terminus, a 5' extension encoding Hind III and Xba I sites. The other primer contained a 5' extension encoding a Bam HI site. The sequences of the primers were as follows:

```
                                           (SEQ ID NO: 38)
cgatcGGATCCTCCAAAACAGATACAGCTGCC
     BamHI    ISWI seq (SEQ ID NO: 39)
gatcgccTCTAGACTCGAGAAGCTTACTTGTCATCGTCGTCCTTGTAGTC
       XbaI      HindIII     FLAG sequence GCTGCCCTTCTTCTTCTTTTTCGAGTT
       ISWI seq
```

Amplification was conducted at 95° C. for 2 min, followed by 30 cycles of 95° C. for 30 sec, 55° C. for 30 sec, 72° C. for 5 min, and a final step of 72° C. for 5 min. This resulted in the generation of an amplification product comprising ISWI- and FLAG-encoding sequences flanked by Bam HI and Hind III sites. The amplification product was purified using a PCR Cleanup Kit (Qiagen, Valencia, Calif.) according to the manufacturer's instructions, then digested with Bam HI and Hind III.

A vector encoding a nuclear localization signal (NLS), a ZFP binding domain targeted to the human erythropoietin gene (Epo 2C), a VP 16 activation domain and a FLAG epitope was digested with Bam HI and Hind III to release VP16- and FLAG-encoding sequences. The Ban HI/Hind III fragment described in the preceding paragraph was ligated to the vector backbone to generate a vector encoding a fusion protein comprising a NLS, the Epo 2C binding domain, ISWI and FLAG. A vector encoding a protein that is identical, except for the presence of an Epo3B binding domain in place of Epo2C, was constructed by similar methods for use as a control. The nucleotide sequences of the target sites, and the amino acid sequences of the recognition helices (−1 through +6) for the Epo2C and Epo3B binding domains are provided in Table 3.

96:9485-9490; Sheppard et al. (2001) *Mol. Cell. Biol.* 21:39-50 and references cited therein). A construct encoding a portion of SRC 1 common to the a and e isoforms (amino acids 781 through 1385, Kalkhoven et al. (1998) *EMBO J.* 17:232-243), fused to a zinc finger binding domain targeted to the human erythropoietin (EPO) gene, was constructed as follows.

A plasmid encoding SRC1 was used as a template for PCR amplification using the following primers, and the amplification product was digested with Not I.

```
                                           (SEQ ID NO: 48)
5'-GGATCCGGCCACCGCGGCCGCATGGATCCATGTAATACAAACCCAA
CC (SEQ ID NO: 49)
5'-ATGAATTCGCGGCCGCCCTGGGTTCCATCTGCTTCTGTTTTGAG
```

Figure 4:
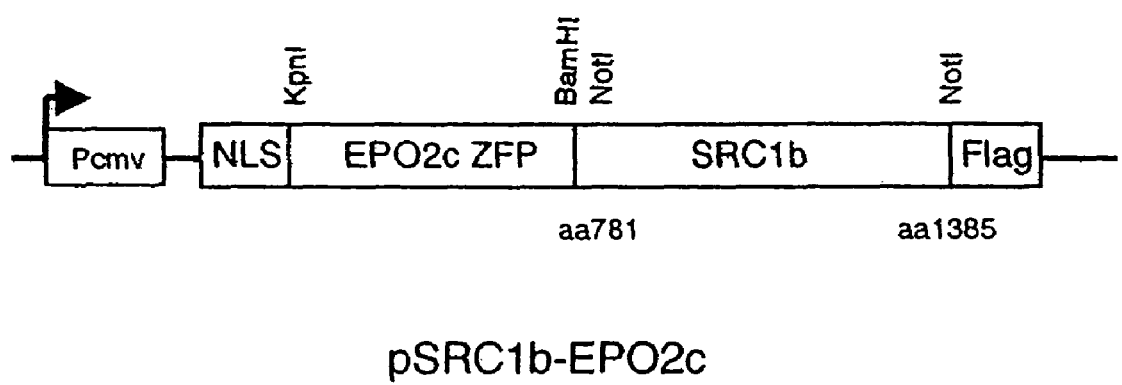
FIG. 4 is a schematic diagram of the plasmid pSRC1b-EPO2C. The rightward-pointing arrow represents the start site of a transcription unit encoding a fusion protein that includes a nuclear localization signal (NLS), a ZFP binding domain targeted to nucleotide-862 of the human erythropoietin gene (EPO2c ZFP), a portion of the SRC1 protein from amino acids 781-1385 (SRC1b), and a FLAG epitope (Flag). pCMV represents a CMV promoter. Selected restriction enzyme recognition sites are also indicated.

The pVP16-EPOZFP-862c vector, containing a transcription unit encoding a nuclear localization signal (NLS), the EPO ZFP-862 zinc finger binding domain, a VP 16 transcriptional activation domain and a FLAG epitope, under transcriptional control of a CMV promoter and a bovine growth hormone polyadenylation signal, was digested with Not I to release VP16-encoding sequences. See Zhang et al. (2000) *J. Biol. Chem.* 275:33,850-33,860 for the design and properties of EPOZFP-862, which binds to a site 862 nucleotides upstream of the EPO transcriptional startsite. The Not I-digested amplification product described in the previous paragraph was inserted into the ZFP-862c vector backbone by ligation, to generate a plasmid encoding a NLS, the EPO ZFP-862 binding domain, amino acids 781-1385 of SRC1 and a FLAG epitope. The structure of the resulting construct, pSRC1b-EPO$_2$c, is illustrated schematically in FIG. 4.

This construct was introduced into human HEK 293 cells by transfection (200 ug of plasmid plus 5 ug of Lipofectamine; Lipofectamine obtained from Gibco/Life Technologies, Gaithersburg, Md.). Approximately 12 hours after exposure of cells to plasmid, the medium was removed and replaced with fresh DMEM supplemented with 10% fetal bovine serum. Twenty-four hours later, the medium was harvested and assayed for secreted EPO, using an erythropoietin ELISA from R&D Systems (Minneapolis, Minn.).

Figure 5:
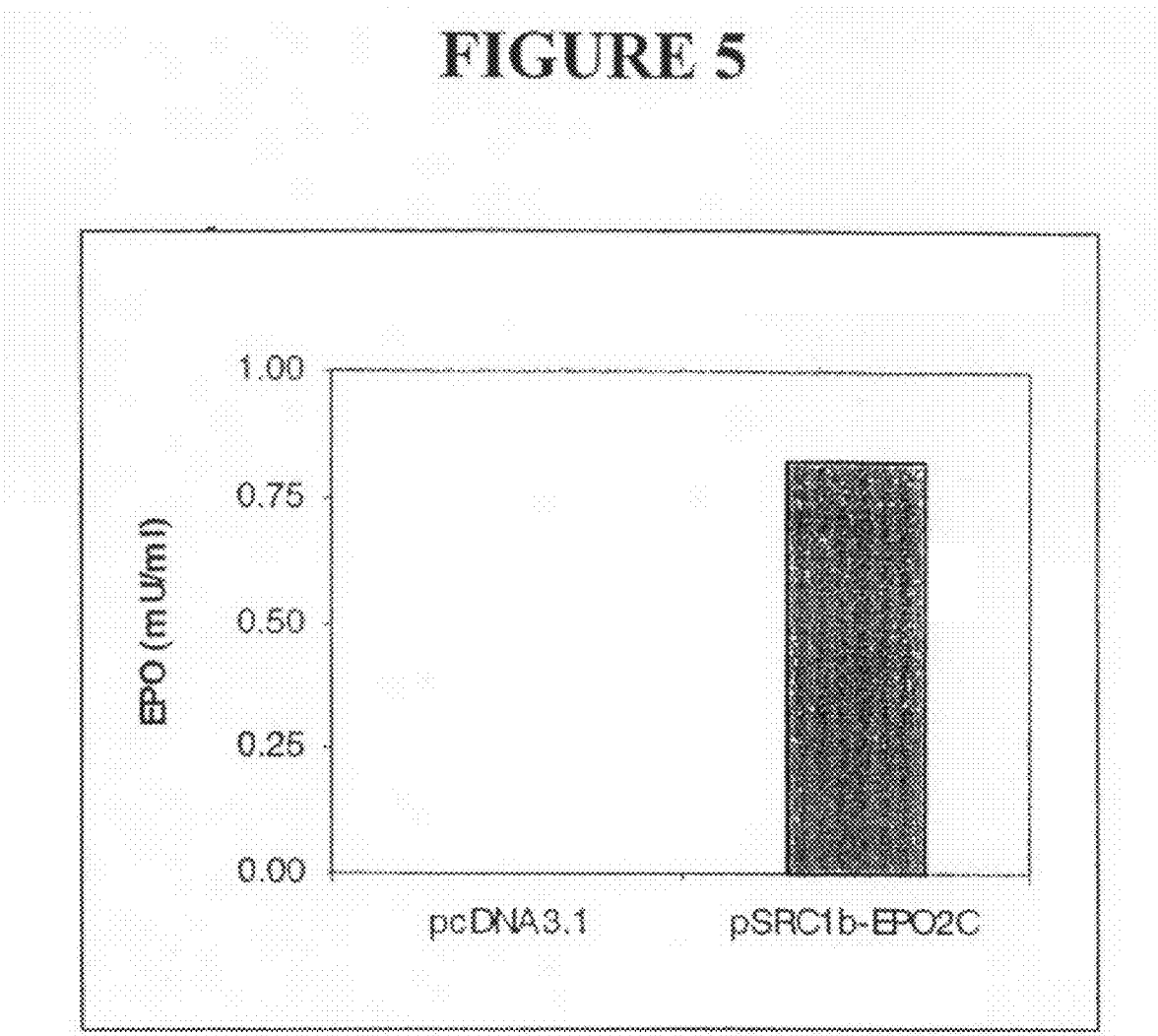
FIG. 5 shows erythropoietin (EPO) levels in transfected and control cells, as determined by ELISA. The bar labeled pSRC1b-EPO2C represents levels of EPO secreted into the medium by cells transfected with a plasmid encoding a fusion between an EPO-targeted ZFP and a portion of the SRC1 protein. pcDNA3.1 represents secreted EPO levels in cells transfected with a control plasmid that does not encode a ZFP-SRC 1 fusion.

Results of the assay, shown in FIG. 5, indicated that transfection of 293 cells with the pSRC1b-EPO2c fusion plasmid activated expression of EPO, compared to cells transfected with a control plasmid (pcDNA3.1) not encoding such a fusion. Thus, ZFP-targeted binding, to the EPO gene, of a protein which is capable of chromatin remodeling (by virtue

TABLE 3

Target sites and recognition helix sequences for Epo2C and Epo3B

| ZFP | Target | F1 (−1 to +=6) | F2 (−1 to +=6) | F3 (−1 to +=6) |
|---|---|---|---|---|
| Epo2c | GGTGAGGAGT | RSDNALR | RSDNLAR | DSSKLSR |
|  | (SEQ ID NO: 40) | (SEQ ID NO: 41) | (SEQ ID NO: 42) | (SEQ ID NO: 43) |
| Epo3b | GCGGTGGCTC | QSSDLTR | RSDALSR | RSDERKR |
|  | (SEQ ID NO: 44) | (SEQ ID NO: 45) | (SEQ ID NO: 46) | (SEQ ID NO: 47) |

Example 12

Activation of EPO Expression by Fusion of SRC-1 to a Zinc Finger Binding Domain

The steroid receptor coactivator 1 (SRC1) protein is a histone acetyltransferase which is capable of recruiting the p300 and CBP proteins (both of which are also histone acetyltransferases). Liu et al. (1999) *Proc. Natl. Acad. Sci. USA* of its histone acetyltransferase activity) and can serve as a component of chromatin remodeling complexes (by virtue of its ability to bind p300 and CBP) resulted in activation of gene expression.

Example 13

Repression of VEGF Expression by ZFP-MBD and ZFP-DNMT Fusions

Methyl binding domain proteins (MBDs) participate in repression of the expression of certain genes by binding to methylated cytosine residues present in CpG dinucleotides and recruiting chromatin remodeling complexes to the site of binding. MBDs are also present as a component of certain chromatin remodeling complexes.

DNA N-methyl transferases (DNMTs) methylate cytosine residues present in certain CpG dinucleotide sequences in cellular DNA. Such methylation can lead to chromatin remodeling at or in the vicinity of the methylated sequence(s) by, for example, binding of one or more MBDs and concomitant or subsequent recruitment of chromatin remodeling complexes. The DNMT1 protein can also associate with histone deacetylases (HDACs), which themselves are involved in chromatin remodeling.

A series of ZFP-MBD and ZFP-DNMT fusions were tested for their ability to regulate expression of the human VEGF-A gene. Accordingly, a series of plasmids was constructed, in which the VEGF3a/1 ZFP binding domain (see Example 3, supra) was fused to MBD2b, MBD3, MBD3S, MBD3L, DNMT1, DNMT3a or DNMT3b. See, for example, GenBank accession numbers AF072243, AF170347, AW872007, and NM013595. The fusion genes also comprised a nuclear localization signal and a FLAG epitope, similar to the constructs described in Examples 11 and 12. FIG. 6 shows a schematic diagram of these constructs.

Figure 7:
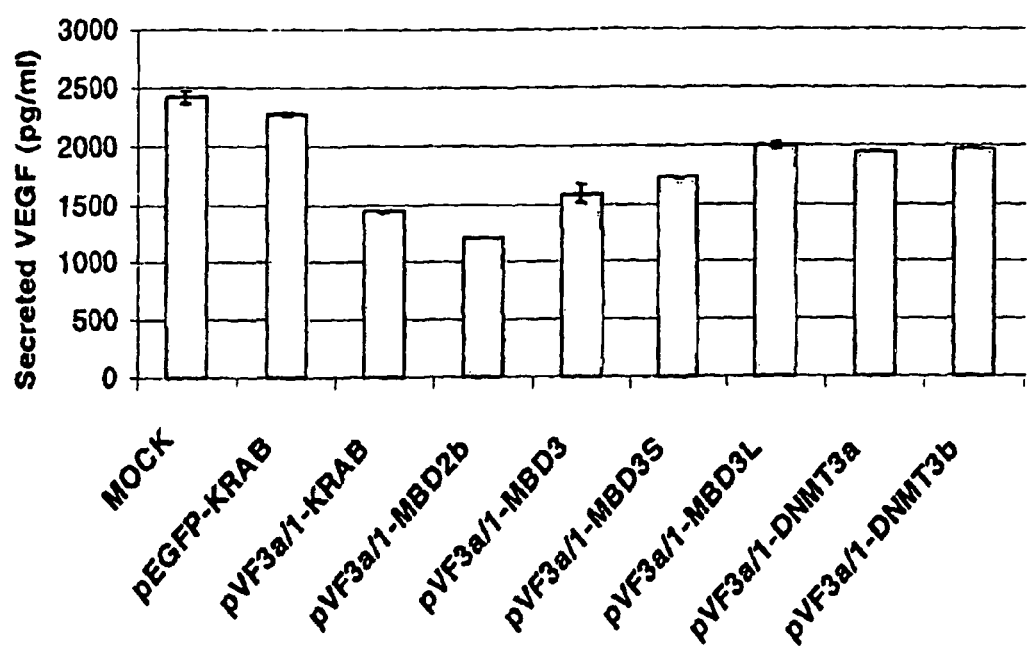
FIG. 7 shows VEGF levels in transfected and control cells, as determined by ELISA. MOCK refers to cells transfected with a vector that does not contain a ZFP-MBD or ZFP-DNMT fusion. pEGFP-KRAB refers to cells transfected with a green fluorescent protein-encoding plasmid. PVF3a/1 refers to the VEGF3a/1 DNA binding domain described in Examples 3 and 13. MBD refers to various methyl binding domain proteins. DNMT refers to various DNA N-methyl transferases.

HeLa cells were transfected with the constructs shown in FIG. 6. Seventy-two hours after transfection, secreted VEGF levels were measured using a VEGF ELISA (R&D Systems, Minneapolis, Minn.) according to the manufacturer's instructions. Cells were co-transfected with a green fluorescent protein-encoding plasmid to allow measurement of transfection efficiency. The results, presented in FIG. 7, show that transfection of HeLa cells with all of the MBD and DNMT fusions tested resulted in repression of VEGF expression. When corrected for transfection efficiency (approximately 50% in this experiment), intracellular expression of the MBD2b-VEGF3a/1 fusion resulted in essentially 100% repression of VEGF expression. Thus, fusions between a targeted ZFP binding domain and proteins whose mechanism of modulating gene expression involves chromatin remodeling are able to repress gene expression.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A method of screening for a compound that modulates the activity of a chromatin modifying enzyme, the method comprising the steps of:
   (a) contacting an isolated cell with the compound, wherein the cell comprises a polynucleotide encoding fusion protein comprising a zinc finger protein and a functional chromatin modifying enzyme and wherein the ZFP binds to a gene within the cell; and
   (b) determining the level of expression of the gene, wherein a difference in gene expression between the contacted cells as compared to control cells is indicative that the compound modulates activity of the chromatin modifying enzyme.

2. The method of claim 1, wherein the modifying enzyme modifies a chromosomal protein.

3. The method of claim 1, wherein the gene is an endogenous cellular gene.

4. The method of claim 1, wherein the level of expression of the gene is determined by mRNA analysis.

5. The method of claim 1, wherein the gene is extrachromosomal.

* * * * *

SEQUENCE LISTING

```
<160> NUMBER OF SEQ ID NOS: 49

<210> SEQ ID NO 1
<211> LENGTH: 9
<212> TYPE: DNA
<213> ORGANISM: Artificial Sequence
<220> FEATURE:
<223> OTHER INFORMATION: Description of Artificial Sequence:  Veg 1
      target site 3' to 5'

<400> SEQUENCE: 1 cccctccta                                                                9

<210> SEQ ID NO 2
<211> LENGTH: 9
<212> TYPE: DNA
<213> ORGANISM: Artificial Sequence
<220> FEATURE:
<223> OTHER INFORMATION: Description of Artificial Sequence:  Veg 1
      target site 5' to 3'

<400> SEQUENCE: 2 ggggaggat                                                                9

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence:  Veg 1 AA
      sequence F1
```

```
<400> SEQUENCE: 3

Thr Thr Ser Asn Leu Arg Arg
 1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Veg 1 AA
      sequence F2

<400> SEQUENCE: 4

Arg Ser Ser Asn Leu Gln Arg
 1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Veg 1 AA
      sequence F3

<400> SEQUENCE: 5

Arg Ser Asp His Leu Ser Arg
 1               5

<210> SEQ ID NO 6
<211> LENGTH: 9
<212> TYPE: DNA
<213> ORGANISM: Artificial Sequence
<220> FEATURE:
<223> OTHER INFORMATION: Description of Artificial Sequence: Veg 3a
      target site

<400> SEQUENCE: 6 gcggaggct                                                                 9

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Veg 3a AA
      sequence F1

<400> SEQUENCE: 7

Gln Ser Ser Asp Leu Gln Arg
 1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Veg 3a AA
      sequence F2

<400> SEQUENCE: 8

Arg Ser Ser Asn Leu Gln Arg
 1               5

<210> SEQ ID NO 9
<211> LENGTH: 7
<212> TYPE: PRT
<213> ORGANISM: Artificial Sequence
```

-continued

```
<220> FEATURE:
<223> OTHER INFORMATION: Description of Artificial Sequence: Veg 3a AA
      sequence F3

<400> SEQUENCE: 9

Arg Ser Asp Glu Leu Ser Arg
 1               5

<210> SEQ ID NO 10
<211> LENGTH: 298
<212> TYPE: DNA
<213> ORGANISM: Artificial Sequence
<220> FEATURE:
<223> OTHER INFORMATION: Description of Artificial Sequence: Veg1
      nucleotide sequence

<400> SEQUENCE: 10
ggtacccata cctggcaaga agaagcagca catctgccac atccagggct gtggtaaagt      60
ttacggcaca acctcaaatc tgcgtcgtca cctgcgctgg cacaccggcg agaggccttt    120
catgtgtacc tggtcctact gtggtaaacg cttcacccgt tcgtcaaacc tgcagcgtca    180
caagcgtacc cacaccggtg agaagaaatt tgcttgcccg gagtgtccga agcgcttcat    240
gcgtagtgac cacctgtccc gtcacatcaa gacccaccag aataagaagg gtggatcc      298

<210> SEQ ID NO 11
<211> LENGTH: 99
<212> TYPE: PRT
<213> ORGANISM: Artificial Sequence
<220> FEATURE:
<223> OTHER INFORMATION: Description of Artificial Sequence: Veg1 amino
      acid sequence

<400> SEQUENCE: 11

Val Pro Ile Pro Gly Lys Lys Gln His Ile Cys His Ile Gln Gly
 1               5                  10                  15

Cys Gly Lys Val Tyr Gly Thr Thr Ser Asn Leu Arg Arg His Leu Arg
                20                  25                  30

Trp His Thr Gly Glu Arg Pro Phe Met Cys Thr Trp Ser Tyr Cys Gly
            35                  40                  45

Lys Arg Phe Thr Arg Ser Ser Asn Leu Gln Arg His Lys Arg Thr His
        50                  55                  60

Thr Gly Glu Lys Lys Phe Ala Cys Pro Glu Cys Pro Lys Arg Phe Met
 65                  70                  75                  80

Arg Ser Asp His Leu Ser Arg His Ile Lys Thr His Gln Asn Lys Lys
                85                  90                  95

Gly Gly Ser

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: duplex
      oligonucleotide binding target 5'-3'

<400> SEQUENCE: 12
catgcatagc ggggaggatc gccatcgat                                        29

<210> SEQ ID NO 13
<211> LENGTH: 14
<212> TYPE: PRT
<213> ORGANISM: Artificial Sequence
```

<220> FEATURE:
<223> OTHER INFORMATION: Description of Artificial Sequence: NLS
derived SV40 large T-antigen

<400> SEQUENCE: 13

Met Ala Pro Lys Lys Lys Arg Lys Val Gly Ile His Gly Val
1               5                   10

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence:
double-stranded oligonucleotide encoding a FLAG
epitope

<400> SEQUENCE: 14

Asp Tyr Lys Asp Asp Asp Asp Lys
1               5

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: target
site for human VEGF-A

<400> SEQUENCE: 15
ggggaggatc gcggaggct                                              19

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: linker
sequence

<400> SEQUENCE: 16

Asp Gly Gly Gly Ser
1               5

<210> SEQ ID NO 17
<211> LENGTH: 298
<212> TYPE: DNA
<213> ORGANISM: Artificial Sequence
<220> FEATURE:
<223> OTHER INFORMATION: Description of Artificial Sequence: Veg3a
nucleotide sequence

<400> SEQUENCE: 17
ggtacccata cctggcaaga agaagcagca catctgccac atccagggct gtggtaaagt      60
ttacggccag tcctccgacc tgcagcgtca cctgcgctgg cacaccggcg agaggccttt     120
catgtgtacc tggtcctact gtggtaaacg cttcacccgt tcgtcaaacc tacagaggca     180
caagcgtaca cacaccggtg agaagaaatt tgcttgcccg gagtgtccga agcgcttcat     240
gcgaagtgac gagctgtcac gacatatcaa gacccaccag aacaagaagg gtggatcc      298

<210> SEQ ID NO 18
<211> LENGTH: 99
<212> TYPE: PRT
<213> ORGANISM: Artificial Sequence
<220> FEATURE:
<223> OTHER INFORMATION: Description of Artificial Sequence: Veg3a amino acid sequence

<400> SEQUENCE: 18

Val Pro Ile Pro Gly Lys Lys Gln His Ile Cys His Ile Gln Gly
1               5                   10                  15

Cys Gly Lys Val Tyr Gly Gln Ser Ser Asp Leu Gln Arg His Leu Arg
                20                  25                  30

Trp His Thr Gly Glu Arg Pro Phe Met Cys Trp Ser Tyr Cys Gly
        35                  40                  45

Lys Arg Phe Thr Arg Ser Ser Asn Leu Gln Arg His Lys Arg Thr His
    50                  55                  60

Thr Gly Glu Lys Lys Phe Ala Cys Pro Glu Cys Pro Lys Arg Phe Met
65                  70                  75                  80

Arg Ser Asp Glu Leu Ser Arg His Ile Lys Thr His Gln Asn Lys Lys
                85                  90                  95

Gly Gly Ser

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: Veg3a DNA
      target site

<400> SEQUENCE: 19
catgcatatc gcggaggctt ggcatcgat                                      29

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: primer
      SPE7

<400> SEQUENCE: 20
gagcagaatt cggcaagaag aagcagcac                                      29

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: primer
      SPEamp12

<400> SEQUENCE: 21
gtggtctaga cagctcgtca cttcgc                                         26

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: primer
      SPEamp13

<400> SEQUENCE: 22
ggagccaagg ctgtggtaaa gtttacgg                                       28

<210> SEQ ID NO 23
<211> LENGTH: 26

```
<212> TYPE: DNA
<213> ORGANISM: Artificial Sequence
<220> FEATURE:
<223> OTHER INFORMATION: Description of Artificial Sequence: primer
      SPEamp11

<400> SEQUENCE: 23
ggagaagctt ggatcctcat tatccc                                          26

<210> SEQ ID NO 24
<211> LENGTH: 77
<212> TYPE: DNA
<213> ORGANISM: Artificial Sequence
<220> FEATURE:
<223> OTHER INFORMATION: Description of Artificial Sequence: fragment
      encoding DGGGS linker, 5' to 3'

<400> SEQUENCE: 24
ctagacacat caaaacccac cagaacaaga aagacggcgg tggcagcggc aaaaagaaac     60
agcacatatg tcacatc                                                    77

<210> SEQ ID NO 25
<211> LENGTH: 77
<212> TYPE: DNA
<213> ORGANISM: Artificial Sequence
<220> FEATURE:
<223> OTHER INFORMATION: Description of Artificial Sequence: fragment
      encoding DGGGS linker, 3' to 5'

<400> SEQUENCE: 25
tgtgtagttt tgggtggtct tgttctttct gccgccaccg tcgccgtttt tctttgtcgt     60
gtatacagtg taggttc                                                    77

<210> SEQ ID NO 26
<211> LENGTH: 39
<212> TYPE: DNA
<213> ORGANISM: Artificial Sequence
<220> FEATURE:
<223> OTHER INFORMATION: Description of Artificial Sequence: primer
      GB19

<400> SEQUENCE: 26
gccatgccgg tacccatacc tggcaagaag aagcagcac                            39

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: primer
      GB10

<400> SEQUENCE: 27
cagatcggat ccacccttct tattctggtg ggt                                  33

<210> SEQ ID NO 28
<211> LENGTH: 589
<212> TYPE: DNA
<213> ORGANISM: Artificial Sequence
<220> FEATURE:
<223> OTHER INFORMATION: Description of Artificial Sequence: Veg3a/1
      nucleotide sequence

<400> SEQUENCE: 28
ggtacccata cctggcaaga agaagcagca catctgccac atccagggct gtggtaaagt     60
```

```
ttacggccag tcctccgacc tgcagcgtca cctgcgctgg cacaccggcg agaggccttt    120
catgtgtacc tggtcctact gtggtaaacg cttcacacgt tcgtcaaacc tacagaggca    180
caagcgtaca cacacaggtg agaagaaatt tgcttgcccg gagtgtccga agcgcttcat    240
gcgaagtgac gagctgtcta gacacatcaa aacccaccag aacaagaaag acggcggtgg    300
cagcggcaaa aagaaacagc acatatgtca catccaaggc tgtggtaaag tttacggcac    360
aacctcaaat ctgcgtcgtc acctgcgctg gcacaccggc gagaggcctt tcatgtgtac    420
ctggtcctac tgtggtaaac gcttcacccg ttcgtcaaac ctgcagcgtc acaagcgtac    480
ccacaccggt gagaagaaat ttgcttgccc ggagtgtccg aagcgcttca tgcgtagtga    540
ccacctgtcc cgtcacatca agacccacca gaataagaag ggtggatcc                589
```

<210> SEQ ID NO 29
<211> LENGTH: 196
<212> TYPE: PRT
<213> ORGANISM: Artificial Sequence
<220> FEATURE:
<223> OTHER INFORMATION: Description of Artificial Sequence: Veg3a/1
    amino acid sequence

<400> SEQUENCE: 29

Val Pro Ile Pro Gly Lys Lys Lys Gln His Ile Cys His Ile Gln Gly
 1               5                  10                  15

Cys Gly Lys Val Tyr Gly Gln Ser Ser Asp Leu Gln Arg His Leu Arg
            20                  25                  30

Trp His Thr Gly Glu Arg Pro Phe Met Cys Thr Trp Ser Tyr Cys Gly
        35                  40                  45

Lys Arg Phe Thr Arg Ser Ser Asn Leu Gln Arg His Lys Arg Thr His
    50                  55                  60

Thr Gly Glu Lys Lys Phe Ala Cys Pro Glu Cys Pro Lys Arg Phe Met
65                  70                  75                  80

Arg Ser Asp Glu Leu Ser Arg His Ile Lys Thr His Gln Asn Lys Lys
                85                  90                  95

Asp Gly Gly Gly Ser Gly Lys Lys Lys Gln His Ile Cys His Ile Gln
           100                 105                 110

Gly Cys Gly Lys Val Tyr Gly Thr Thr Ser Asn Leu Arg Arg His Leu
       115                 120                 125

Arg Trp His Thr Gly Glu Arg Pro Phe Met Cys Thr Trp Ser Tyr Cys
   130                 135                 140

Gly Lys Arg Phe Thr Arg Ser Ser Asn Leu Gln Arg His Lys Arg Thr
145                 150                 155                 160

His Thr Gly Glu Lys Lys Phe Ala Cys Pro Glu Cys Pro Lys Arg Phe
                165                 170                 175

Met Arg Ser Asp His Leu Ser Arg His Ile Lys Thr His Gln Asn Lys
            180                 185                 190

Lys Gly Gly Ser
        195

<210> SEQ ID NO 30
<211> LENGTH: 42
<212> TYPE: DNA
<213> ORGANISM: Artificial Sequence
<220> FEATURE:
<223> OTHER INFORMATION: Description of Artificial Sequence: Veg3a/1
    target site 1

<400> SEQUENCE: 30

-continued agcgagcggg gaggatcgcg gaggcttggg gcagccgggt ag                42

<210> SEQ ID NO 31
<211> LENGTH: 42
<212> TYPE: DNA
<213> ORGANISM: Artificial Sequence
<220> FEATURE:
<223> OTHER INFORMATION: Description of Artificial Sequence: Veg3a/1
      target site 2

<400> SEQUENCE: 31
tcgcccctcc tagcgcctcc gaacccgtc ggcccatctc gc                42

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: VEGF
      forward primer

<400> SEQUENCE: 32
ctggtagcgg ggaggatcg                                         19

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: VEGF
      reverse primer

<400> SEQUENCE: 33
gccacgacct ccgagctac                                         19

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: VEGF probe

<400> SEQUENCE: 34
ctacccggct gccccaagcc tc                                     22

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: GAPDH
      forward primer

<400> SEQUENCE: 35
ccttttgcag accacagtcc a                                      21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: GAPDH
      reverse primer

<400> SEQUENCE: 36
gcagggatga tgttctggag a                                      21

```
<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: GAPDH
      probe

<400> SEQUENCE: 37
cactgccacc cagaagactg tgg                                              23

<210> SEQ ID NO 38
<211> LENGTH: 32
<212> TYPE: DNA
<213> ORGANISM: Artificial Sequence
<220> FEATURE:
<223> OTHER INFORMATION: Description of Artificial Sequence: ISWI
      primer 1

<400> SEQUENCE: 38
cgatcggatc ctccaaaaca gatacagctg cc                                    32

<210> SEQ ID NO 39
<211> LENGTH: 77
<212> TYPE: DNA
<213> ORGANISM: Artificial Sequence
<220> FEATURE:
<223> OTHER INFORMATION: Description of Artificial Sequence: ISWI
      primer 2

<400> SEQUENCE: 39
gatcgcctct agactcgaga agcttacttg tcatcgtcgt ccttgtagtc gctgcccttc      60
ttcttctttt tcgagtt                                                     77

<210> SEQ ID NO 40
<211> LENGTH: 10
<212> TYPE: DNA
<213> ORGANISM: Artificial Sequence
<220> FEATURE:
<223> OTHER INFORMATION: Description of Artificial Sequence: Epo2c
      target site

<400> SEQUENCE: 40
ggtgaggagt                                                             10

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Epo2c
      recognition helix F1

<400> SEQUENCE: 41

Arg Ser Asp Asn Ala Leu Arg
 1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Epo2c
      recognition helix F2

<400> SEQUENCE: 42
```

-continued

Arg Ser Asp Asn Leu Ala Arg
 1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Epo2c
      recognition helix F3

<400> SEQUENCE: 43

Asp Ser Ser Lys Leu Ser Arg
 1               5

<210> SEQ ID NO 44
<211> LENGTH: 10
<212> TYPE: DNA
<213> ORGANISM: Artificial Sequence
<220> FEATURE:
<223> OTHER INFORMATION: Description of Artificial Sequence: Epo3b
      target site

<400> SEQUENCE: 44
gcggtggctc                                                          10

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Epo3b
      recognition helix F1

<400> SEQUENCE: 45

Gln Ser Ser Asp Leu Thr Arg
 1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Epo3b
      recognition helix F2

<400> SEQUENCE: 46

Arg Ser Asp Ala Leu Ser Arg
 1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Epo3b
      recognition helix F3

<400> SEQUENCE: 47

Arg Ser Asp Glu Arg Lys Arg
 1               5

<210> SEQ ID NO 48
<211> LENGTH: 48
<212> TYPE: DNA
<213> ORGANISM: Artificial Sequence
<220> FEATURE:
<223> OTHER INFORMATION: Description of Artificial Sequence: SRC1

-continued

```
      primer 1

<400> SEQUENCE: 48
ggatccggcc accgcggccg catggatcca tgtaatacaa acccaacc              48

<210> SEQ ID NO 49
<211> LENGTH: 44
<212> TYPE: DNA
<213> ORGANISM: Artificial Sequence
<220> FEATURE:
<223> OTHER INFORMATION: Description of Artificial Sequence:  SRC1
      primer 2

<400> SEQUENCE: 49
atgaattcgc ggccgccctg ggttccatct gcttctgttt tgag                  44
```